(12) United States Patent
Arndt et al.

(10) Patent No.: US 6,664,439 B1
(45) Date of Patent: Dec. 16, 2003

(54) ABSORBENT ARTICLES WITH DISTRIBUTION MATERIALS POSITIONED UNDERNEATH STORAGE MATERIAL

(75) Inventors: Silke Arndt, Darmstadt (DE); Bruno Johannes Ehrnsperger, Frankfurt (DE); Mattias Schmidt, Idstein (DE); Gary Dean Lavon, Oberursel (DE); Frank Neumann, Cincinnati, OH (US); Andrea Lieselotte Link, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,225

(22) PCT Filed: Apr. 23, 1999

(86) PCT No.: PCT/IB99/00751
§ 371 (c)(1),
(2), (4) Date: Oct. 27, 2000

(87) PCT Pub. No.: WO99/55265
PCT Pub. Date: Nov. 4, 1999

(51) Int. Cl.[7] .................................................. A61F 13/15
(52) U.S. Cl. ....................... 604/378; 604/385.101; 604/368; 604/369; 604/374; 604/375
(58) Field of Search ................................ 604/365, 367, 604/368, 369, 374, 375, 378, 385.101, 366, 383, 370, 381, 384, 389, 386; 428/131–137, 219; 442/199, 352, 359, 362, 363, 364, 370, 385, 415, 416

(56) References Cited

U.S. PATENT DOCUMENTS

| | | | |
|---|---|---|---|
| 3,156,242 A | 11/1964 | Crowe, Jr. ................... | 128/296 |
| 3,224,926 A | 12/1965 | Bernardin ................... | 162/146 |
| 3,440,135 A | 4/1969 | Chung ........................ | 162/157 |

(List continued on next page.)

FOREIGN PATENT DOCUMENTS

| | | | | |
|---|---|---|---|---|
| AU | 199728385 B2 | 6/1997 | ......... | C07D/417/12 |
| EP | 0 312 118 B1 | 4/1989 | ........... | A61F/13/15 |
| EP | 0 343 940 B2 | 11/1989 | ........... | A61F/13/46 |
| EP | 0 397 110 B1 | 11/1990 | ........... | A61F/13/15 |
| EP | 0 512 010 B1 | 11/1992 | ........... | A61F/13/15 |
| EP | 0 565 606 B1 | 10/1993 | ........... | A61F/13/46 |
| EP | 0 710 471 B1 | 5/1996 | ........... | A61F/13/15 |
| EP | 0 809 991 A1 | 12/1997 | ........... | A61F/13/15 |
| EP | 0 820 746 A1 | 1/1998 | ........... | A61F/13/15 |
| EP | 0 963 747 A1 | 12/1999 | ........... | A61F/13/15 |
| EP | 0 976 373 A1 | 2/2000 | ........... | A61F/13/15 |
| GB | 2 024 100 A | 1/1980 | ............ | B32B/5/02 |
| WO | WO 93/25172 | 12/1993 | ........... | A61F/13/15 |
| WO | WO 95/16562 | 6/1995 | ............ | B32B/5/24 |
| WO | WO 95/16746 | 6/1995 | ........... | C08L/67/02 |
| WO | WO 94/14395 | 7/1995 | ........... | A61F/13/15 |
| WO | WO 96/39031 | 12/1996 | .......... | A01N/25/34 |
| WO | WO 97/05046 | 2/1997 | ........... | B65G/17/42 |
| WO | WO 97/20701 | 6/1997 | ............ | B44B/5/00 |
| WO | WO 97/20842 | 6/1997 | ........ | C07D/473/16 |
| WO | WO 98/19861 | 5/1998 | ........... | B32B/27/12 |

*Primary Examiner*—Weilun Lo
*Assistant Examiner*—Jacqueline Stephens
(74) *Attorney, Agent, or Firm*—Edward J. Milbrada; Eileen L. Hughett; Ken K. Patel

(57) ABSTRACT

An absorbent article having an ultimate fluid storage region and a fluid distribution region, positioned between the ultimate storage region and the garment oriented surface of the article, in fluid communication with the ultimate fluid storage region, the ultimate fluid storage region includes a material which has: (1) a Capillary Sorption Desorption Capacity at 100 cm (CSDC 100) of at least 10 g/g; (2) a Capillary Sorption Desorption Capacity at 0 cm (CSDC 0) higher than the CSDC 100; (3) a Loosely Bound Liquid Capacity (LBLC); and (4) a Capillary Sorption Desorption Release Height when 50% of the LBLC are released (CSDRH 50) less than 60 cm. Further, the liquid distribution layer material has a Capillary Sorption Absorption Height at 30% of its maximum capacity (CSAH 30) of at least 35 cm. Disuibution material can be foam materials, particularly those derived from high internal phase water-in-oil emulsions.

54 Claims, 11 Drawing Sheets

U.S. PATENT DOCUMENTS

| | | | |
|---|---|---|---|
| 3,699,103 A | 10/1972 | Kiss | 260/210 |
| 3,770,731 A | 11/1973 | Jaeger | 260/248 |
| 3,881,489 A | 5/1975 | Hartwell | 128/287 |
| 3,932,309 A | 1/1976 | Graham et al. | 252/439 |
| 3,989,867 A | 11/1976 | Sisson | 428/132 |
| 4,035,147 A | 7/1977 | Sangenis et al. | 8/116.4 |
| 4,493,870 A | 1/1985 | Vrouenraets et al. | 428/245 |
| 4,673,402 A | 6/1987 | Weisman et al. | 604/368 |
| 4,725,481 A | 2/1988 | Ostapchenko | 428/213 |
| 4,935,022 A | 6/1990 | Lash et al. | 604/368 |
| 4,968,312 A | 11/1990 | Khan | 604/388.1 |
| 4,976,819 A | 12/1990 | Minton | 162/9 |
| 4,990,147 A | 2/1991 | Freeland | 604/385.2 |
| 5,171,236 A | 12/1992 | Dreier et al. | 604/369 |
| 5,244,541 A | 9/1993 | Minton | 162/27 |
| 5,260,345 A | 11/1993 | DesMarais et al. | 521/148 |
| 5,269,755 A | 12/1993 | Bodicky | 604/53 |
| 5,306,266 A | 4/1994 | Freeland | 604/385.1 |
| 5,387,207 A | 2/1995 | Dyer et al. | 604/369 |
| 5,397,318 A | 3/1995 | Dreier | 604/385.2 |
| 5,445,874 A | 8/1995 | Shehata | 428/252 |
| 5,454,800 A | 10/1995 | Hirt et al. | 604/378 |
| 5,514,121 A | 5/1996 | Roe et al. | 604/385.1 |
| 5,540,671 A | 7/1996 | Dreier | 604/385.2 |
| 5,554,142 A | 9/1996 | Dreier et al. | 604/385.1 |
| 5,560,222 A | 10/1996 | Perron | 62/435 |
| 5,562,646 A | 10/1996 | Goldman et al. | 604/368 |
| 5,563,179 A | 10/1996 | Stone et al. | 521/64 |
| 5,563,703 A | 10/1996 | Lebeau et al. | 356/237 |
| 5,599,335 A | 2/1997 | Goldman et al. | 604/368 |

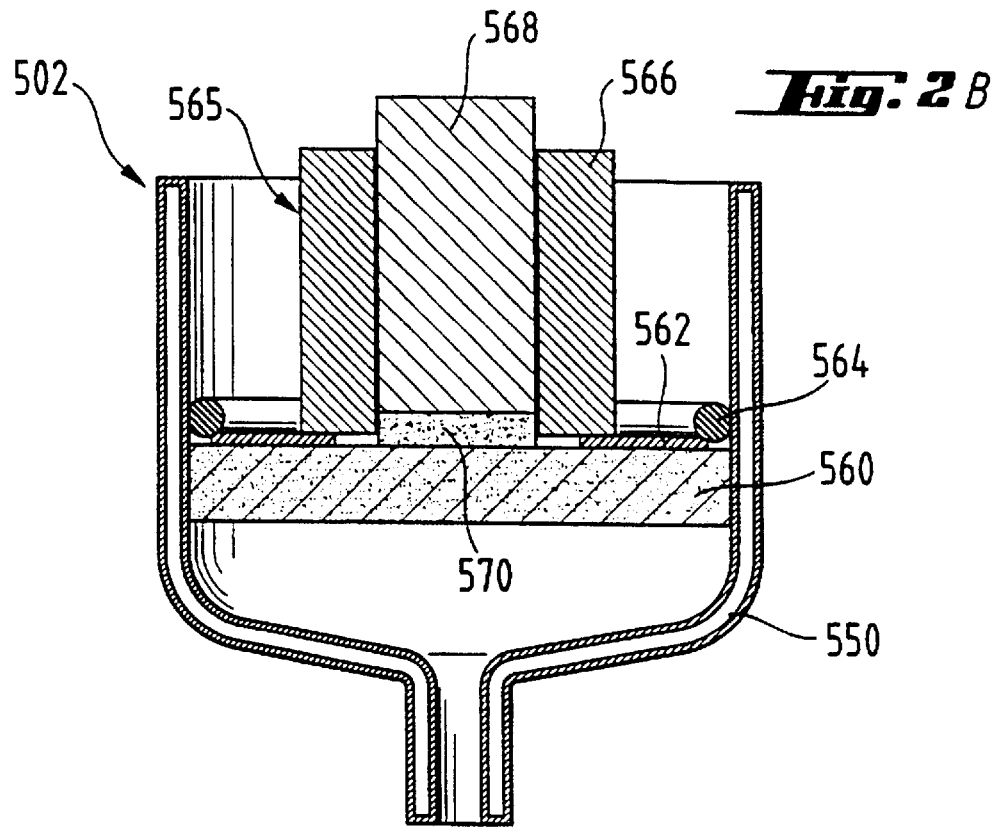
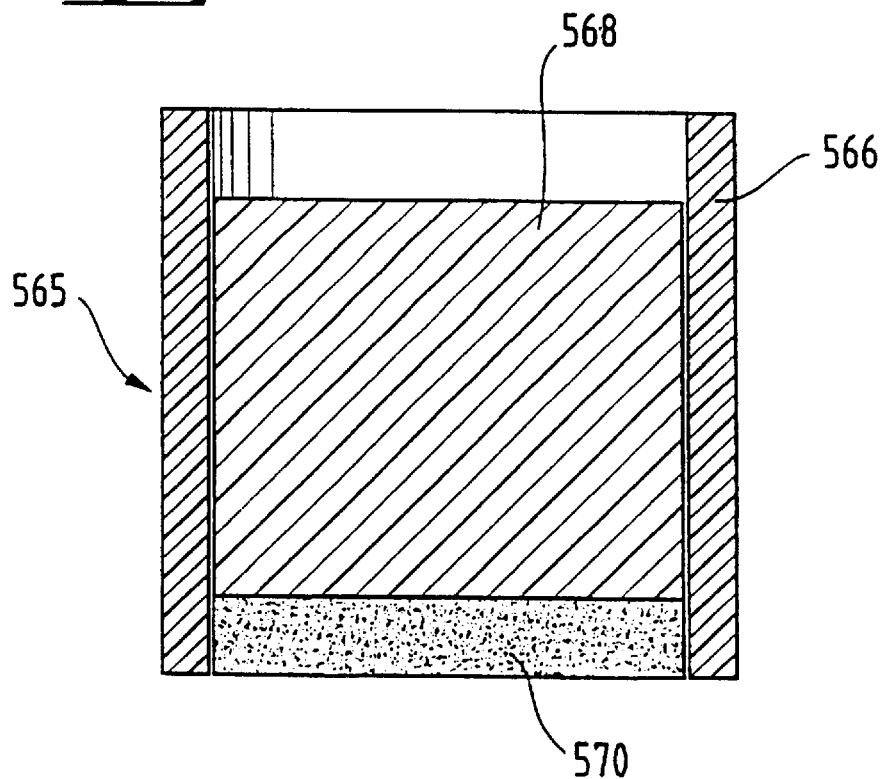

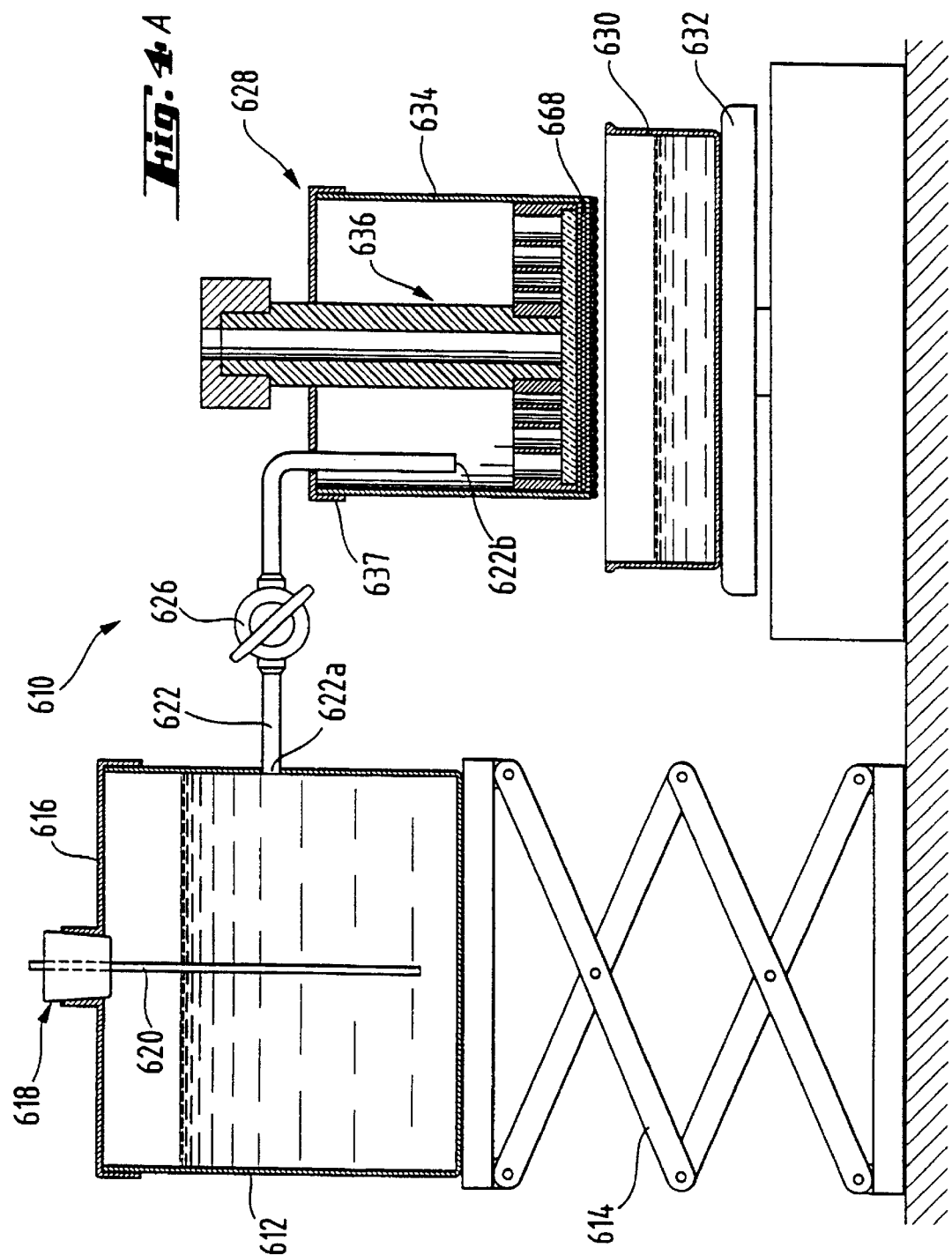

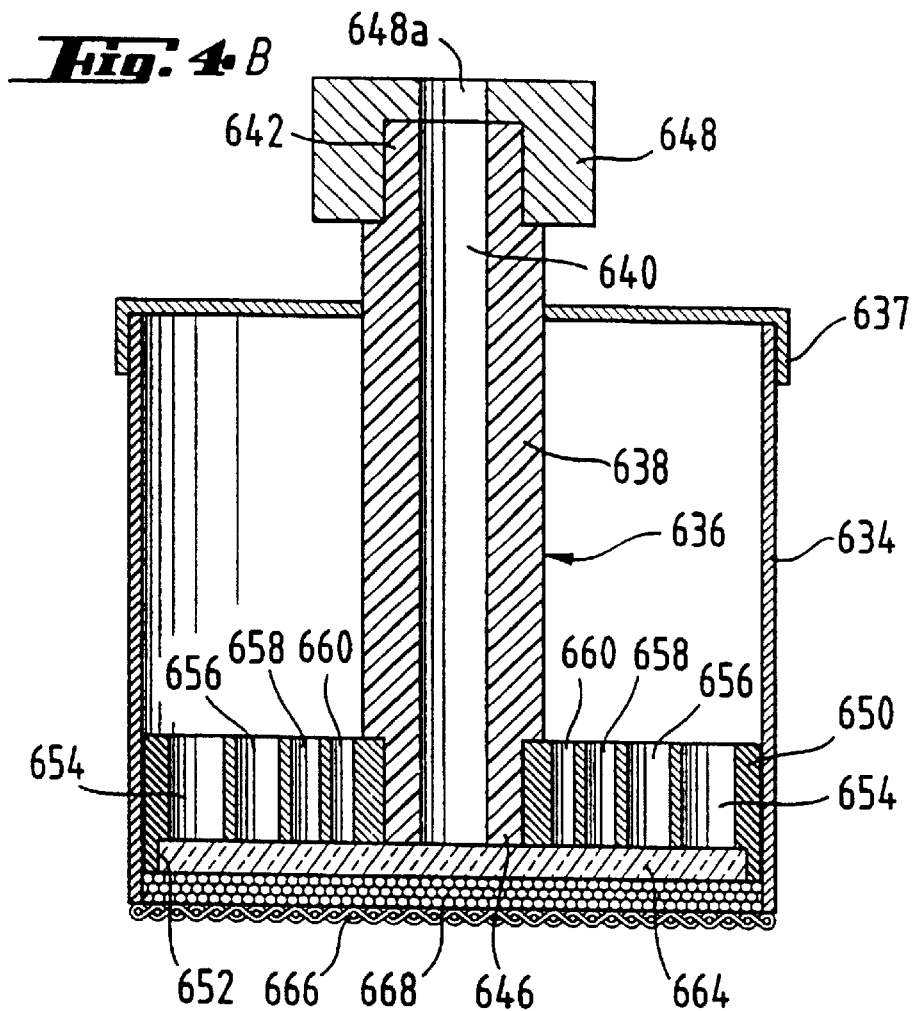
*Fig. 4.B*
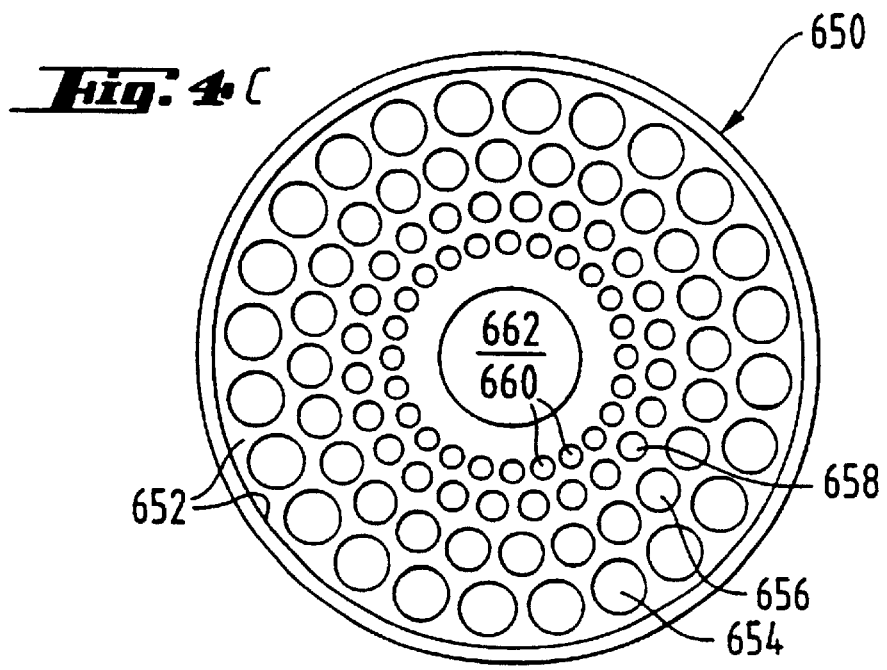
*Fig. 4.C*

ABSORBENT ARTICLES WITH DISTRIBUTION MATERIALS POSITIONED UNDERNEATH STORAGE MATERIAL

GENERAL FIELD OF THE INVENTION

The present invention relates to absorbent articles which are primarily designed to receive and retain bodily discharges such as urine. Such articles are disposable hygiene articles like baby diapers, training pants, adult incontinence articles and the like.

BACKGROUND/PRIOR ART

Absorbent Articles for receiving and retaining bodily discharges such as urine or feces such as disposable diapers, training pants, adult incontinence articles are well known in the art, and significant effort has been spent against improving their performance. The ability to provide better performing absorbent articles such as diapers has been contingent on the ability to develop relatively thin absorbent cores or structures that can acquire and store large quantities of discharged body fluids, in particular urine.

In this regard, the use of certain absorbent polymers often referred to as "hydrogels", "superabsorbents" or "hydrocolloid" or "hydrogel forming" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers. See also, U.S. Pat. No. 5,562,646 (Goldman et al.), issued Oct. 8, 1996 and U.S. Pat. No. 5,599,335 (Goldman et al.), issued Feb. 4, 1997, both of which relate to absorbent cores comprising regions of high concentrations of hydrogel-forming polymer, where the polymer forms a gel-continuous fluid transportation zone upon swelling.

In addition or alternatively to the use of hydrogel-forming absorbent polymers as the primary component in absorbent article storage structures, the use of polymeric foam materials derived from high internal phase water-in-oil emulsions ("HIPEs") has been identified. See, e.g., U.S. Pat. No. 5,260,345 (DesMarais et al.), issued Nov. 9, 1993, U.S. Pat. No. 5,387,207 (Dyer et al.) issued Feb. 7, 1995, and U.S. Pat. No. 5,560,222 (DesMarais et al.), issued Jul. 22, 1997.

Further disclosure is made of structures having a low capacity in the regions between the legs of the wearer such as in PCT application U.S. Ser. No. 97/050,46, filed on Mar. 27, 1997, relating to the movement of fluid through certain regions of the article comprising materials having good acquisition and distribution properties to other regions comprising materials having specific liquid storage capabilities.

Further prior art aimed at providing material with improved fluid acquisition/distribution performance, such as by providing "surge management means" between the absorbent core and the topsheet, see for example EP-A-0.397.110 or EP-A-0.312.118.

Other documents disclose Absorbent articles with distribution layers underlying a storage layer which has a "fluid passage way" allowing fluid to pass from the surface to the underlying distribution layer without penetrating the absorbent materials in a microscopic view (see for example EP-A-0.565.606 or EP-A-0.343.940). Alternative designs were described, where the fluid was enabled to penetrate through the overlaying storage layer because this layer has a relatively low ultimate storage capacity, such as by having only small amounts of superabsorbent material, see for example EP-A-0.512.010.

In U.S. Pat. No. 5,454,800 (Hirt et al.), absorbent articles are disclosed, comprising at least a first and a second absorbent member in a layered arrangement, such that lower layer—for example a paper tissue—has better wicking properties than the first layer, which can be made from large pore materials such as co-form or air-laid tissue webs, or which can have gaps or apertures to allow fluid penetration into the under-laying layer.

Yet other articles describe the use of superabsorbent materials for being used in absorbent structures, whereby the materials exhibit a liquid permeability, expressed in "Saline Flow Conductivity", end as described in U.S. Pat. No. 5,599,335.

A further class of documents describe materials having improved fluid distribution properties, such as having high flux as disclosed in EP-A-0.809.991 or high wicking capability as disclosed in copending U.S. patent application Ser. No. 09/042,418, filed Mar. 13, 1998 by T. DesMarais et al. titled "Absorbent materials for distributing aqueous liquids", now U.S. Pat. No. 6,013,589.

However, a problem with using distribution materials as described in such art is that a relatively high capillary absorbent pressure is required for the storage materials to drain the distribution materials.

Thus, there is still a need to improve towards well performing articles, which provide good acquisition, good distribution without detrimentally affecting comfort of the wearer, such as providing low thickness, prevent a hard feel especially on the outer side of the article (often referred to as "poly-pockmarking"), which even might cause liquid to penetrate through. In particular, the combination of low thickness with small core sizes resulted in the need for overall "basis capacities", i.e. high amounts of fluid storage capacity per unit area.

OBJECTS OF THE INVENTION

Henceforth, it is an object of the present invention to provide an absorbent article with improvements in the above mentioned areas, in particular to provide an absorbent article which is easy to manufacture, even on conventional production lines.

It is a further object of the present invention to provide an absorbent article, which exploits the benefits of particularly suitable distribution materials with fluid storage materials or members of conventional type.

SUMMARY

The present invention is an absorbent article, such as for use in hygienic applications, which has an ultimate fluid storage region, and a fluid distribution region positioned between the ultimate storage region and the garment oriented surface of the article, which is in fluid communication with the ultimate fluid storage region, whereby the ultimate fluid storage region comprises material which has (1) a Capillary Sorption Desorption Capacity at 100 cm (CSDC 100) of at least 10 g/g; which further has (2) a Capillary Sorption Desorption Capacity at 0 cm (CSDC 0) higher than said CSDC 100 and which thereby has (3) a Loosely Bound Liquid Capacity (LBLC) as the difference between (CSDC 0 and CSDC 100); and which has (4) a Capillary Sorption Desorption Release Height when 50% of said LBLC are released (CSDRH 50) of less than 60 cm. Further, the liquid distribution layer comprises material having a Capillary Sorption Absorption Height at 30% of its maximum capacity (CSAH 30) of at least 25 cm.

The present invention also relates to an absorbent article, having a fluid receiving surface oriented towards the wearer during use, and a garment oriented surface opposite said fluid receiving surface, further having an ultimate fluid storage region, and a fluid distribution region positioned between said ultimate storage region and said garment oriented surface, and in fluid communication with said ultimate fluid storage region, wherein said distribution region comprises fluid distribution material having a Capillary Sorption Absorption Height at 30% of its maximum capacity (CSAH 30) of at least 35 cm, and wherein the ultimate fluid storage region comprises ultimate fluid storage material which has a Capillary Sorption Desorption Capacity at 100 cm (CSDC 100); and which further has a Capillary Sorption Desorption Capacity at 0 cm (CSDC 0) higher than said CSDC 100, thereby having a Loosely Bound Liquid Capacity (LBLC) as the difference between (CSDC 0 and CSDC 100); and having a Capillary Sorption Desorption Release Height when 50% of said LBLC are released (CSDRH 50), which is less than said Capillary Sorption Absorption height at 30% of its maximum capacity (CSAH 30) of the distribution material.

Additionally, the ultimate fluid storage region can have a SFC value of more than $25 \times 10^{-7}$ $cm^3sec/g$., preferably more than $70 \times 10^{-7}$ $cm^3sec/g$, more preferably more than $100 \times 10^{-7}$ $cm^3sec/g$, even more preferably more than $200 \times 10^{-7}$ $cm^3sec/g$, most preferably more than $400 \times 10^{-7}$ $cm^3sec/g$ or even more than $1000 \times 10^{-7}$ $cm^3sec/g$.

In a further aspect, the present invention can have a fluid distribution region material having a CSAH 30 of at least 50 cm.

In yet another aspect, the fluid distribution region material has a CSDH 50 of less than 150 cm. Alternatively, the benefits of the fluid distribution material can be described by having a fluid permeability value at 50% saturation (k(50)), which is at least 15% of the permeability value at 100% saturation (k(100)), preferably more than 18%, even more preferably more than 25% and most preferably more than 35% of the permeability value at 100% saturation (k(100)).

In yet another aspect, the fluid distribution region material has a permeability at 100% saturation (k(100)) of at least 1 Darcy, preferably of at least 8 Darcy.

In a preferred embodiment of the present invention, the distribution region material has a expansion factor of at least 4, preferably of at least 5, more preferably of at least 8, and most preferably of at least 15.

Another preferred execution of the present invention has distribution region material having a Cumulative Flux value at 15 cm in the Vertical Wicking test of at least 0.02 $g/cm^2/min$, preferably more than 0.04, even more preferably of more than 0.07 $g/cm^2/min$, and most preferably more than 0.14 $g/cm^2/min$.

Suitable materials for being useful for the present invention as fluid distribution and/or storage component can be foam materials, preferably polymeric foam material, and even more preferably polymeric foam material which is derived from high internal phase water-in-oil emulsions.

Alternatively, the distribution region can comprise fibrous material, preferably chemically stiffened cellulose, and/or synthetic fibers. Optionally, the distribution material can be mechanically treated after formation.

The distribution region according to the present invention can be a single layer material or is comprised of several layers, can be of essentially homogeneous composition and/or density and/or basis weight.

The ultimate fluid storage region can comprise fibrous material, preferably, this region comprises superabsorbent materials. Preferably, these materials have a SFC of at least $50 \times 10^{-7}$ $cm^3sec/g$, preferably of at least $80 \times 10^{-7}$ $cm^3sec/g$ more preferably of at least 100 $cm^3sec/g$, and even more preferably of at least 150 $cm^3sec/g$.

The ultimate fluid storage region can be essentially homogeneous in composition, and can be a single or multi-layered structure. Preferably, the storage region is essentially free of void, apertures, or gaps having an individual void, aperture or gap volume of more than 10 $mm^3$.

When the absorbent article of the present invention is sectioned into a crotch and one or more waist regions, the crotch region can have a lower ultimate fluid storage capability than one or more waist region together, preferably less than 49%, more preferably less than 41% and even more preferably less than 23% of the total core ultimate fluid storage capacity.

In yet another aspect, the present invention is an absorbent article which has a relatively low basis weight of the liquid storage member of less than 450 $g/m^2$, and for which the basis weight of the liquid storage member is essentially constant throughout it, such as by having the basis weight of the ultimate storage material in the crotch region differing by less than 20% (dry weight basis) throughout the article.

In yet another aspect the absorbent article according to the present invention has a length of the crotch region which is half of the length of the total absorbent core. In a preferred embodiment the ultimate fluid storage region covers a surface area of at least 1.2 times the surface area of said fluid distribution region.

In an even further aspect, the absorbent article according to the present invention comprises a breathable backsheet having an MVTR value of at least 200 $g/m^2/24$ hrs, in a preferable execution of the microporous or monolithic type, which can be in liquid communication with the distribution layer of the present invention.

BRIEF DESCRIPTION OF DRAWINGS

FIG. 2B—Cross-sectional view of glass frit

FIG. 2C—Enlarged view of cylinder/piston assembly

FIG. 4A—Saline Flow Conductivity Test stand schematic view

FIG. 4B—Sectional view of piston/cylinder assembly

FIG. 4C—Plan view of piston head

DETAILED DESCRIPTION

Definitions

Figure 1:
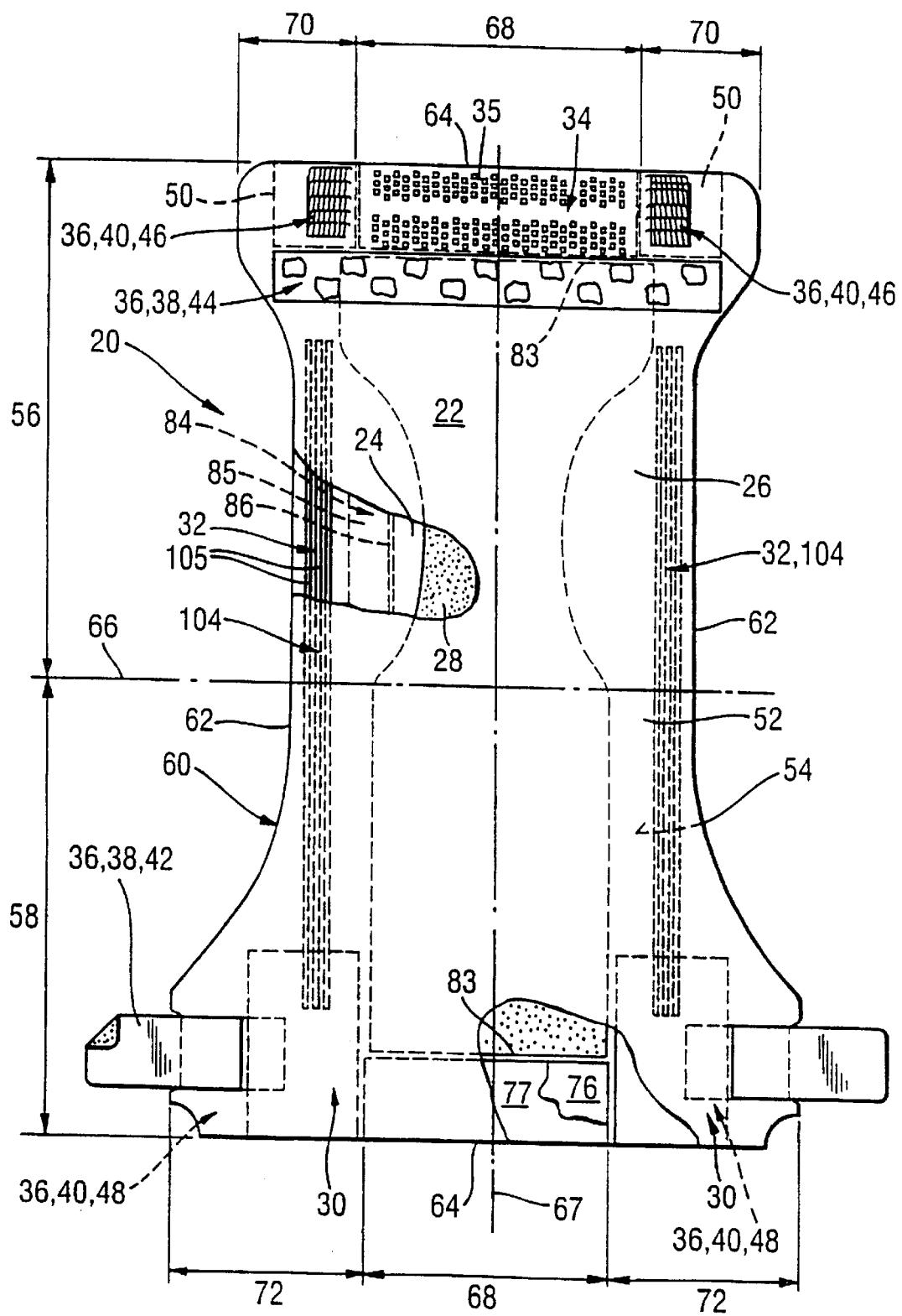
FIG. 1—Diaper as example for an absorbent article

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes, but is not limited to, urine, menses and vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling functionality, e.g., fluid acquisition, fluid distribution, fluid transportation, fluid storage, etc. The absorbent member can comprise the entire absorbent core or only a portion of the absorbent core, i.e., the absorbent core can comprise one or more absorbent members. The "storage absorbent member" is the absorbent member component(s) of the absorbent core that function primarily to ultimately store absorbed fluids. As discussed above, the storage absorbent member may also distribute fluid as a result of its vertical wicking capability.

As used herein, the terms "region(s)" or "zone(s)" refer to portions or sections of the absorbent member.

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, it should also be understood that the term "upper" refers to absorbent members, such as layers, that are nearest to the wearer of the absorbent article during use, and typically face the topsheet of an absorbent article; conversely, the term "lower" refers to absorbent members that are furthermost away from the wearer of the absorbent article and typically face the backsheet.

All percentages, ratios and proportions used herein are calculated by weight unless otherwise specified.

Absorbent Articles—General Description (FIG. 1)

An absorbent article generally comprises:
- an absorbent core (which may consist of sub-structures or absorbent members);
- a fluid pervious topsheet;
- a substantially fluid impervious backsheet;
- optionally further features like closure elements or elastification.

FIG. 1 is a plan view of an exemplary embodiment of an absorbent article of the invention which is a diaper.

The diaper 20 is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a liquid pervious topsheet 24, a substantially liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. Particularly useful executions of backsheets 26 are described in more detail hereinafter. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The topsheet is preferably compliant, soft feeling, and non-irritating to the user's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. The topsheet can comprise further materials, such as lotions or emmolients, such as described in EP-A-0.794.804.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20).

FIG. 1 shows a specific execution of the diaper 20 in which the topsheet 24 and the backsheet 26 are unitary across the core and the chassis region and have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and ,the end edges 64.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region.

The elasticized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

Regions of Absorbent Articles and Their Relative Arrangement

Generally, absorbent hygienic articles are intended for being worn around the lower end of the body torso. It is an essential design feature of these articles to cover the regions of the body where the discharges occur ("discharge regions"), which extend around the respective body openings. The respective zones of the absorbent article covering the discharge regions are correspondingly referred to as "loading zones". Thus during use, the articles are generally arranged on the wearer such that they extend (for a standing position of the wearer) from the crotch between the legs upwards, both in the front and the back of the wearer.

Generally, such articles have a length dimension exceeding their width dimension, whereby the article is worn such that the axis of the length dimension is aligned with the height direction of the wearer when standing, whilst the width direction of the article is aligned with a line extending from left to right of the wearer.

Because of the anatomy of the human wearer, the space between the legs of the wearer generally confines the space available for the article in this region. For good fit, an absorbent article should be designed such that it fits well in the crotch region. If the width of the article is excessively wide relative to the crotch width of the wearer, the article may be deformed, which might results in deteriorated performance, and reduced wearers comfort.

The point, where the article has its smallest width to fit best between the legs of the wearer then coincides with the point on the wearer, where the distance between the legs is the narrowest, and is—for the scope of the present invention—referred to as the "crotch point".

If the crotch point of an article is not obvious from its shape, it can be determined by placing the article on a wearer of the intended user group (e.g. a toddler) then positioning the wearer in a standing position, and then placing an extensible filament around the legs in a figure eight configuration. The point in the article corresponding to the point of intersection of the filament is deemed to be the crotch point of the article and consequently also of the absorbent core being affixed within this article.

Whilst this crotch point of the article is often in the middle of the article (in longitudinal direction) this is not necessarily the case. It can very well be, that the part of the article which is intended to be worn in the front is smaller than the back (or rear) part—either in its length dimension, or width, or both, or surface area. Also, the crotch point does not need to be positioned in the middle of the absorbent core, in particular when the absorbent core is not placed longitudinally centered within the article.

The crotch region is the area surrounding the crotch point, so as to cover the respective body openings, respectively discharge regions. Unless otherwise mentioned, this region extends over a length of 50% of the total core length (which, in turn is defined as the distance between the front and rear waist edges of the core, which might be approximated by straight lines perpendicular to the longitudinal center line). If the crotch point is positioned in the middle of the article, then the crotch region starts (when counting from the front core edge) at 25% of total length and extends up to 75% of the total core length. Or, the front and the rear quarter of the length of the absorbent core do not belong to the crotch region.

The crotch region length being 50% of the total absorbent core length has been derived for baby diapers, where it has been confirmed that this is a suitable means to describe the fluid handling phenomena. If the present invention is applied in articles having drastically different dimensions, it might become necessary to reduce these 50% (as in the case for Severe Incontinence articles) or to increase this ratio (as in the case for Ultra Light or Light Incontinence articles). In more general terms, this crotch region of the article should not extend much beyond the discharge region of the wearer.

If the crotch point is positioned offset from the mid-point of the article, the crotch region still covers 50% of the total article length (in longitudinal direction), however, not evenly distributed between front and back, but proportionally adjusted to this off-set.

As an example for an article having a total core length of 500 mm, and having a crotch point which is positioned centered, the crotch region will extend from 125 mm away from the front edge up to 375 mm away from front edge. Or, if the crotch point lies 50 mm offset towards the front core edge, (i.e. being 200 mm away from front core edge), the crotch region extends from 75 to 325 mm.

In general terms, for an article having a total core length of $L_c$, a crotch point being at a distance $L_{cp}$ away from the front core edge, and a crotch zone length of $L_{cz}$, the front edge of said crotch zone will be positioned at a distance $$L_{fecz}=L_{cp}*(1-0.5L_{cz}/L_{cp}).$$

For example the absorbent article can be a baby diaper, for being worn by toddlers (i.e. of about 12 to 18 kg baby weight) whereby the size of the article in the trade is generally referred to as MAXI size. Then the article has to be able to receive and retain both fecal materials and urine, whereas for the context of the present invention the crotch region has to be capable to primarily receive urine loading.

The total area and size of the crotch region is—of course—also depending on the respective width of the absorbent core, i.e. if the core is narrower in the crotch region than outside the crotch region, the crotch region can have a smaller area (surface) than the remaining area of the absorbent core.

Whilst it can be contemplated, that the boundaries between crotch region and the rest of the article can also be curvilinear, they are approximated within the present description to be straight lines, perpendicular to the longitudinal axis of the article.

The "crotch region" is further confined by the width of the core in this respective region, and the "crotch region area" by the surface as being defined by the crotch region length and the respective absorbent core width.

As a complementary element to the crotch region, the absorbent core also comprises at least one but mostly two waist region(s), extending towards the front and/or the rear of the absorbent core outside the crotch region.

The various elements of the absorbent article and especially of the absorbent core can further be distinguished by their functionality.

Thereby, the region being closest to the loading point of the articles needs generally to ensure that the body exudates which are to be absorbed by the article are sufficiently quickly acquired so as to not remain on the surface of the article, where it might have too much undesired contact with the wearers skin. This region is often referred to as the acquisition region.

Another region can be considered where the received body exudates are to be ultimately stored. This can be done in one region, which might be directly adjacent to the acquisition region, or this might be done primarily in a region somewhat distant from the acquisition region. Also, there can be more than one storage region, either in direct contact with each other (such as when placing two storage material layers on top of each other), or which can have no direct contact with each other (such as when placing each one storage region in the front and back parts of the article).

In any of the above cases, it can be desirable to have a further region, which has a primary functionality of fluid distribution, i.e. transporting the fluid primarily in x.y. direction of the article, such as from the acquisition region to the storage region or regions.

In an absorbent article, the regions can be combined in one unitary and homogeneous structure or material. More preferably, however, at least some of the regions have different fluid handling properties different so as to be better adapted for their specific functionality. Often it is preferred to design the regions from materials having different properties.

For the particularly preferred designs according to the present invention, there must be at least one fluid storage region, and at least one other fluid acquisition/distribution region.

Each of the regions can have various shapes, such as being flat, (i.e. having essentially an x,y extension with essentially constant thickness dimension), or three-dimensionally shaped. Further, these regions can be arranged in various relative positions to each other, such as being layered, or circumscribing in x.y-direction each other.

Preferred executions of the article comprising the various region have these arranged such that they have only little negative impact on the comfort of the wearer, and ideally no negative impact at all. This has to be considered for the article in its unloaded ("dry") state, as well as in its loaded state. For the latter a particularly preferred execution has a small width dimension in the crotch region, and also has relatively lower fluid storage capability in this region, so as to not increase the bulk between the legs even for a loaded article.

The various regions must be in fluid communicating contact with each other, i.e., there must be the possibility of the body exudates to move from the acquisition zone to the storage zone, and doing so by moving through the distribution region, if present.

Whilst the respective regions are referred to by their primary functionality, they generally also have at least to a certain degree other functionality. Thus, a fluid absorbent storage region may also have a fluid distribution functionality, and a fluid acquisition/distribution region may have some fluid retention capability.

Design Capacity and Ultimate Storage Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual babies.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loading of up to 75 ml per voiding, with on an average of four voidings per wearing period resulting in a total loading of 300 ml, and voiding rates of 15 ml/sec have been found to be sufficiently representative.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the processes under consideration have asymptotic kinetic behavior, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

As discussed in the above for varying the dimensions of the article, one skilled in the art will be able to readily adopt the appropriate design capacities for other intended user groups.

Absorbent Members

Apart from looking at the various regions of the absorbent core from a functionality point of view, it is often desirable to consider an absorbent core to be composed of one or more absorbent members or structures, which might consist of sub-structures, such than an absorbent core can be considered to be composed of one or—as in most cases of modern absorbent article designs—several different "materials". Within the context of the present invention, a material forming an absorbent member is an element which can be tested for its "material properties", independent of whether the material is a "pure" material (e.g. a particle of superabsorbent material), an accumulation of homogeneous material (e.g. a mass of cellulose fibers, or a foam structure, or a mass of superabsorbent particles), a mixture of two or more pure materials or material accumulations (e.g. a mixture of superabsorbent particles having different properties, or a blend of superabsorbent particles and cellulosic fibers); or a further arrangement of several materials forming a distinctable absorbent member (such as a two layer composite).

Hence, it will be possible to assess the fluid handling properties of a "fluid handling member", and for certain members it will also be possible to assess the properties of the substructures or materials comprised therein.

The functional regions as described above can be formed out of the same material (for example cellulose web, or a mixture of cellulose and superabsorbent material), whereby the different regions are defined for example by varying densities. More preferably, such different properties can be achieved by using different members and/or materials, allowing a wider range of design flexibility by allowing hydrophilicity, or pore size or other properties relevant for fluid handling to be varied over a much wider range.

The article according to the present invention is characterized in that the fluid distribution region is positioned underneath the fluid storage region. This means, that—when viewing the relative positioning of these two regions during the intended use of the article—the storage region is positioned closer towards the wearer during use. Or, if the absorbent article has a topsheet, which is intended to form the wearer oriented surface of the article, and a backsheet, which forms the garment oriented surface of the article, the storage region is positioned underneath the topsheet, the distribution is positioned underneath the storage region, and the backsheet is positioned underneath the distribution region. This also means, that the liquid as released by the wearer, will follow a z-directionally oriented flow path through the storage region, before it will reach the distribution region. There, the fluid will be transported through the distribution member to other regions of the article, namely to regions which are laterally and/or longitudinally spaced away from the loading point of the article.

Often, but not necessarily, the regions are in the form of layers, such a storage layer overlaying a layer of distribution material. These layers can be, but not necessarily have to be of the same x- and/or y-dimensions, however, the upper storage layer or regions has to cover the distribution region at least in the loading region, i.e. the region where the body exudates contact the absorbent article.

Often, but not necessarily, the article will have a designs such that the width is narrower at least in parts of the crotch region, which results in combination with uniform basis weights of layered material in a lower capacity in the crotch region.

A preferred arrangement of the distribution and the storage regions is such that the storage region has a non-uniform basis capacity distribution, such that the crotch region of the wearer has a lower capacity than the end regions. Such basis capacity can be achieved by a change in overall basis weight profile, i.e. by putting more absorbent material towards the end regions. Or, it could be achieved by positioning material (or material mixture) with a higher absorbency per weight unit towards the end regions.

Capillary Sorption

The fluid handling properties of the various members or materials useful for the present invention are heavily depending on the fluid absorption and desorption properties. The so called Capillary Sorption test is a very useful tool to determine various parameters relating to these properties. Therefore, the test is described in more detail in the following, and the respective parameters are explained thereafter:

Capillary Sorption Test

Purpose

The purpose of this test is to measure the capillary sorption absorbent capacity, as a function of height, of storage absorbent members of the present invention. (The test is also used to measure the capillary sorption absorbent capacity, as a function of height, of the materials—i.e., without osmotic absorbent, such as hydrogel-forming absorbent polymer, or other optional materials utilized in the absorbent member. Nonetheless, the discussion that follows discusses the Capillary Sorption method as it pertains to measuring an entire storage absorbent member.) Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B.V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs/releases fluid upon demand, the weight loss/gain in the balance fluid reservoir is recorded as fluid uptake, adjusted for uptake of the glass frit as a function of height and evaporation. The uptake or capacity at various capillary suctions (hydrostatic tensions or heights) is measured. Incremental absorption/desorption occurs due to the incremental lowering/raising of the frit (i.e., decreasing/increasing capillary suction).

Time is also monitored during the experiment to enable calculation of initial effective uptake rate (g/g/h) at a given height, such as 200 cm.

The test liquid used in this test is the synthetic urine as described in the separate test section.

General Description of Apparatus Set Up

Figure 2A:
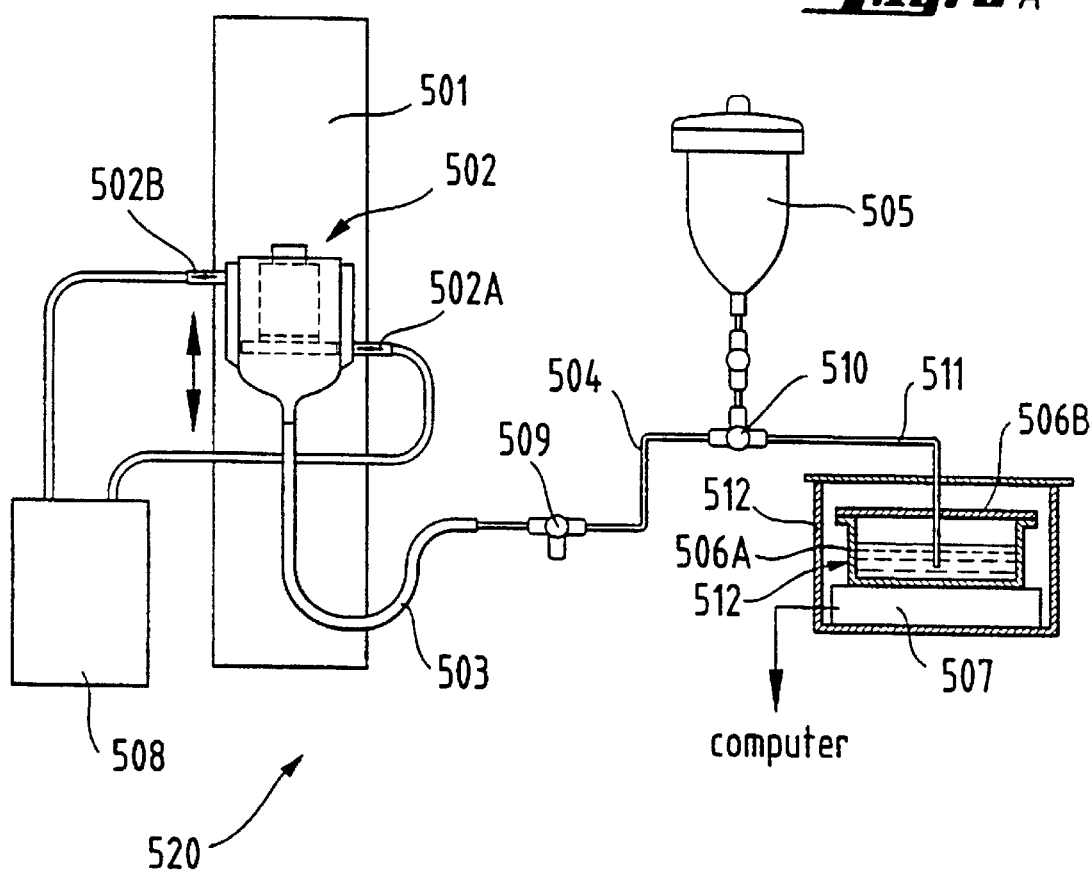
FIG. 2A—General Description of Capillary Sorption equipment

The Capillary Sorption equipment, depicted generally as 520 in FIG. 2A, used for this test is operated under TAPPI conditions (50% RH, 25° C.). A test sample is placed on a glass frit shown in FIG. 2A as 502 that is connected via a continuous column of test liquid (synthetic urine) to a balance liquid reservoir, shown as 506, containing test liquid. This reservoir 506 is placed on a balance 507 that is interfaced with a computer (not shown). The balance should be capable of reading to 0.001 g; such a balance is available from Mettler Toledo as PR1203 (Hightstown, N.J.). The glass frit 502 is placed on a vertical slide, shown generally in FIG. 2A as 501, to allow vertical movement of the test sample to expose the test sample to varying suction heights. The vertical slide may be a rodless actuator which is attached to a computer to record suction heights and corresponding times for measuring liquid uptake by the test sample. A preferred rodless actuator is available from Industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 501 and balance 507, capillary sorption absorbent capacity data may be readily generated for each test sample. Also, computer interface to actuator 501 may allow for controlled vertical movement of the glass frit 502. For example, the actuator may be directed to move the glass frit 502 vertically only after "equilibrium" (as defined below) is reached at each suction height.

The bottom of the funnel with the glass frit 502 is connected to Tygon® tubing 503 that connects the frit 505 to three-way drain stopcock 509. Drain stopcock 509 is connected to liquid reservoir 505 via glass tubing 504 and stopcock 510. (The stopcock 509 is open to the drain only during cleaning of the apparatus or air bubble removal.) Glass tubing 511 connects fluid reservoir 505 with balance fluid reservoir 506, via stopcock 510. Balance liquid reservoir 506 consists of a lightweight 12 cm diameter glass dish 506A and cover 506B. The cover 506B has a hole through which glass tubing 511 contacts the liquid in the reservoir 506. The glass tubing 511 must not contact the cover 506B or an unstable balance reading will result and the test sample measurement cannot be used.

The glass frit diameter must be sufficient to accommodate the piston/cylinder apparatus, discussed below, for holding the test sample. The funnel of the glass frit 502 is jacketed to allow for a constant temperature control from a heating bath. The frit is a 350 ml fritted disc funnel specified as having 4 to 5.5 μm pores, available from Corning Glass Co. (Corning, N.Y.) as #36060-350F. The pores are fine enough to keep the frit surface wetted at capillary suction heights specified (the glass frit does not allow air to enter the continuous column of test liquid below the glass frit).

As indicated, the frit 502 is connected via tubing to fluid reservoir 505 or balance liquid reservoir 506, depending on the position of three-way stopcock 510.

Glass frit 502 is jacketed to accept water from a constant temperature bath. This will ensure that the temperature of the glass frit is kept at a constant temperature of 88° F. (31° C.) during the testing procedure. As is depicted in FIG. 2A, the glass frit 502 is equipped with an inlet port 502A and outlet port 502B, which make a closed loop with a circulating heat bath shown generally as 508. (The glass jacketing is not depicted in FIG. 2A. However, the water introduced to the jacketed glass frit 502 from bath 508 does not contact the test liquid and the test liquid is not circulated through the constant temperature bath. The water in the constant temperature bath circulates through the jacketed walls of the glass frit 502.)

Reservoir 506 and balance 507 are enclosed in a box to minimize evaporation of test liquid from the balance reservoir and to enhance balance stability during performance of the experiment. This box, shown generally as 512, has a top and walls, where the top has a hole through which tubing 511 is inserted.

The glass frit 502 is shown in more detail in FIG. 2B. FIG. 2B is a cross-sectional view of the glass frit, shown without inlet port 502A and outlet port 502B. As indicated, the glass frit is a 350 ml fritted disc funnel having specified 4 to 5.5 μm pores. Referring to FIG. 2B, the glass frit 502 comprises a cylindrical jacketed funnel designated as 550 and a glass frit disc shown as 560. The glass frit 502 further comprises a cylinder/piston assembly shown generally as 565 (which comprises cylinder 566 and piston 568), which confines the test sample, shown as 570, and provides a small confining pressure to the test sample. To prevent excessive evaporation of test liquid from the glass frit disc 560, a Teflon ring shown as 562 is placed on top of the glass frit disc 560. The Teflon® ring 562 is 0.0127 cm thick (available as sheet stock from McMasterCarr as #8569K16 and is cut to size) and is used to cover the frit disc surface outside of the cylinder 566, and thus minimizes evaporation from the glass frit. The ring outer diameter and inner diameter is 7.6 and 6.3 cm, respectively. The inner diameter of the Teflon® ring 562 is about 2 mm less than the outer diameter of cylinder 566. A Viton® O-ring (available from McMasterCarr as #AS568A-

150 and AS568A-151) 564 is placed on top of Teflon® ring 562 to seal the space between the inner wall of cylindrical jacketed funnel 550 and Teflon® ring 562, to further assist in prevention of evaporation. If the O-ring outer diameter exceeds the inner diameter of the cylindrical jacketed funnel 550, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 550 all around its periphery.

Figure 2D:
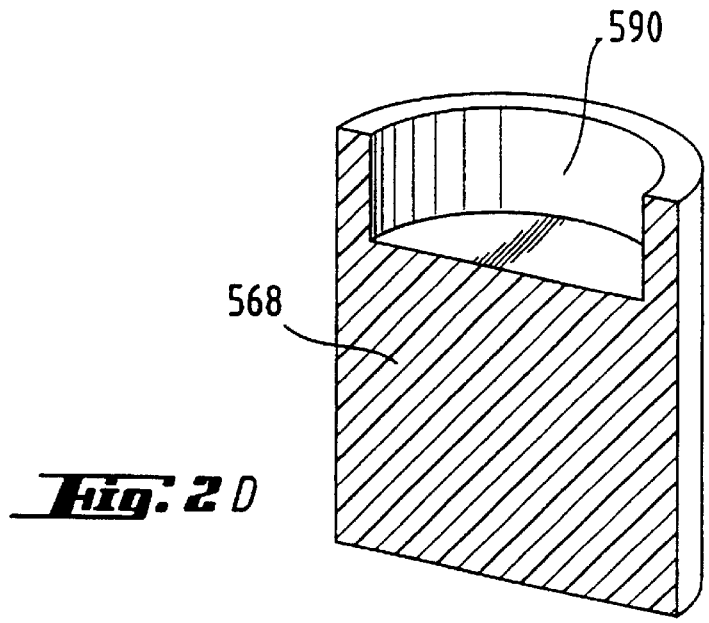
FIG. 2D—Piston detail view

As indicated, a cylinder/piston assembly shown generally in FIG. 2B as 565 confines the test sample and provides a small confining pressure to the test sample 570. Referring to FIG. 2C, assembly 565 consists of a cylinder 566, a cup-like Teflon® piston indicated by 568 and, when necessary, a weight or weights (not shown) that fits inside piston 568. (Optional weight will be used when necessary to adjust the combined weight of the piston and the optional weight so a confining pressure of 0.2 psi (1.4 KPa) is attained depending on the test sample's dry diameter. This is discussed below.) The cylinder 566 is Lexan® bar stock and has the following dimensions: an outer diameter of 7.0 cm, an inner diameter of 6.0 cm and a height of 6.0 cm. The Teflon® piston 568 has the following dimensions: an outer diameter that is 0.02 cm less than the inner diameter of cylinder 566. As shown in FIG. 2D, the end of the piston 568 that does not contact the test sample is bored to provide a 5.0 cm diameter by about 1.8 cm deep chamber 590 to receive optional weights (dictated by the test sample's actual dry diameter) required to attain a test sample confining pressure of 0.2 psi (1.4 kPa). In other words, the total weight of the piston 568 and any optional weights (not shown in figures) divided by the test sample's actual diameter (when dry) should be such that a confining pressure of 0.2 psi (1.4 KPa) is attained. Cylinder 566 and piston 568 (and optional weights) are equilibrated at 31° C. for at least 30 minutes prior to conducting the capillary sorption absorbent capacity measurement.

A non-surfactant treated or incorporated apertured film (14 cm×14 cm) (not shown) is used to cover the glass frit 502 during Capillary Sorption experiments to minimize air destablization around the sample. Apertures are large enough to prevent condensation from forming on the underside of the film during the experiment.

Test Sample Preparation

The test sample can be obtained by punching out a 5.4 cm diameter circular-shaped structure from a storage absorbent member or a liquid distribution member. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component of an absorbent article, the test sample is prepared by combining all the materials that constitute the member such that the combination is representative of the member in question. The test sample is a 5.4 cm diameter circle and is obtained by cutting with an arch punch.

The dry weight of the test sample (used below to calculate capillary sorption absorbent capacity) is the weight of the test sample prepared as above under ambient conditions.

Experimental Set UP

1. Place a clean, dry glass frit 502 in a funnel holder attached to the vertical slide 501. Move the funnel holder of the vertical slide such that the glass frit is at the 0 cm height.
2. Set up the apparatus components as shown in FIG. 2A, as discussed above.
3. Place 12 cm diameter balance liquid reservoir 506 on the balance 507. Place plastic lid 506B over this balance liquid reservoir 506 and a plastic lid over the balance box 512 each with small holes to allow the glass tubing 511 to fit through. Do not allow the glass tubing to touch the lid 506B of the balance liquid reservoir or an unstable balance reading will result and the measurement cannot be used.
4. Stopcock 510 is closed to tubing 504 and opened to glass tubing 511. Fluid reservoir 505, previously filled with test fluid, is opened to allow test fluid to enter tubing 511, to fill balance fluid reservoir 506.
5. The glass frit 502 is leveled and secured in place. Also, ensure that the glass frit is dry.
6. Attach the Tygon® tubing 503 to stopcock 509. (The tubing should be long enough to reach the glass frit 502 at its highest point of 200 cm with no kinks.) Fill this Tygon® tubing with test liquid from liquid reservoir 505.
7. Attach the Tygon® tubing 503 to the level glass frit 502 and then open stopcock 509 and stopcock 510 leading from fluid reservoir 505 to the glass frit 502. (Stopcock 510 should be closed to glass tubing 511.) The test liquid fills the glass frit 502 and removes all trapped air during filling of the level glass frit. Continue to fill until the fluid level exceeds the top of the glass frit disc 560. Empty the funnel and remove all air bubbles in the tubing and inside the funnel. Air bubbles may be removed by inverting glass frit 502 and allowing air bubbles to rise and escape through the drain of stopcock 509. (Air bubbles typically collect on the bottom of the glass frit disc 560.) Relevel the frit using a small enough level that it will fit inside the jacketed funnel 550 and onto the surface of glass frit disc 560.
8. Zero the glass frit with the balance liquid reservoir 506. To do this, take a piece of Tygon® tubing of sufficient length and fill it with the test liquid. Place one end in the balance liquid reservoir 506 and use the other end to position the glass frit 502. The test liquid level indicated by the tubing (which is equivalent to the balance liquid reservoir level) is 10 mm below the top of the glass frit disc 560. If this is not the case, either adjust the amount of liquid in the reservoir or reset the zero position on the vertical slide 501.
9. Attach the outlet and inlet ports from the temperature bath 508 via tubing to the inlet and outlet ports 502A and 502B, respectively, of the glass frit. Allow the temperature of the glass frit disc 560 to come to 31° C. This can be measured by partially filling the glass frit with test liquid and measuring its temperature after it has reached equilibrium temperature. The bath will need to be set a bit higher than 31° C. to allow for the dissipation of heat during the travel of water from the bath to the glass frit.
10. The glass frit is equilibrated for 30 minutes.

Capillary Sorption Parameters

The following describes a computer program that will determine how long the glass frit remains at each height.

In the capillary sorption software program, a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at equilibrium when the flow rate is less than a specified flow rate for a specified number of consecutive time intervals. It is recognized, that for certain material, actual equilibrium may not be reached when the specified "EQUILIBRIUM CONSTANT" is reached. The time interval between readings is 5 seconds.

The number of readings in the delta table is specified in the capillary sorption menu as "EQUILIBRIUM SAMPLES". The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.
Equilibrium Samples=3
Equilibrium Constant=0.0015

| Time Interval | Balance Value (g) | Delta Flow (g/sec) |
|---|---|---|
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

Delta Table:

| Time | 0 | 1 | 2 | 3 | 4 | 5 | 6 | 7 | 8 | 9 |
|---|---|---|---|---|---|---|---|---|---|---|
| Delta1 | 9999 | 0.0180 | 0.0180 | 0.0180 | 0.0090 | 0.0090 | 0.0090 | 0.0014 | 0.0014 | 0.0014 |
| Delta2 | 9999 | 9999 | 0.0150 | 0.0150 | 0.0150 | 0.0050 | 0.0050 | 0.0050 | 0.0008 | 0.0008 |
| Delta3 | 9999 | 9999 | 9999 | 0.0120 | 0.0120 | 0.0120 | 0.0020 | 0.0020 | 0.0020 | 0.0004 |

The following uptake for the above simplified example is 0.318 gram.

The following is the code in C language used to determine equilibrium uptake:

```
/*                          takedata.c                          */
int take_data(int equil_samples,double equilibrium_constant)
{
double   delta;
static   double deltas[500];   /* table to store up to 500 deltas */
double   value;
double   prev_value;
clock_t  next_time;
int      i;
for (i=0; i<equil_samples; i++)      /* initialize all values in the delta
     deltas[i]= 9999.;                   table to 9999. gms/sec */
delta_table_index = 0;               /* initialize where in the table to store
                                        the next delta */
equilibrium_reached = 0;             /* initialize flag to indicate equilibrium
                                        has not been reached */
next_time = clock( );                /* initialize when to take the next
                                        reading */
prev_reading = 0.;                   /* initialize the value of the previous
                                        reading from the balance */
while (!equilibrium_reached) {       /* start of loop for checking for
                                        equilibrium */
     next_time += 5000L;             /* calculate when to take next reading
*/
     while (clock( ) < next_time);   /* wait until 5 seconds has elapsed
                                        from prev reading */
     value = get_balance_reading( ); /* read the balance in grams */
     delta = fabs(prev_value - value) / 5.0;  /* calculate absolute value of flow in
                                        last 5 seconds */
     prev_value = value;             /* store current value for next loop
*/
     deltas[delta_table_index] = delta;  /* store current delta value in the
                                        table of deltas */
     delta_table_index++;            /* increment pointer to next position
                                        in table */
     if (delta_table_index == equil_samples)  /* when the number of deltas = the
                                        number of */
          delta_table_index = 0;     /* equilibrium samples specified, /*
                                     /* reset the pointer to the start of /* the table always contains the last the table. This way */ xx current samples. */
     equilibrium_reached = 1;        /* set the flag to indicate
                                        equilibrium is reached */
     for (i=0; i < equil_samples; i++)  /* check all the values in the delta
                                        table */
          if (deltas[i] >= equilibrium_constant)  /* if any value is > or = to the
```

```
-continued equilibrium constant */
            equilibrium_reached = 0;      /* set the equilibrium flag to 0 (not
at equilibrium) */
        }                                 /* go back to the start of the loop */
}
```

Capillary Sorption Parameters

Load Description (Confining Pressure): 0.2 psi (1.4 KPa) load

Equilibrium Samples (n): 50

Equilibrium Constant: 0.0005 g/sec

Setup Height Value: 100 cm

Finish Height Value: 0 cm (For a full cycle, i.e. also desorption, this value might be different, 200 cm?)

Hydrostatic Head Parameters: 200, 180, 160, 140, 120, 100, 90, 80, 70, 60, 50, 45, 40, 35, 30, 25, 20, 15, 10, 5, 0, 5, 10, 15, 20, 25, 30, 35, 40, 45, 50, 60, 70, 80, 90, 100, 120, 140, 160, 180, and 200 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Capillary Sorption Procedure

1) Follow the experimental setup procedure.
2) Make sure the temperature bath 508 is on and water is circulating through the glass frit 502 and that the glass frit disc 560 temperature is 31° C.
3) Position glass frit 502 at 200 cm suction height. Open stopcocks 509 and 510 to connect glass frit 502 with the balance liquid reservoir 506. (Stopcock 510 is closed to liquid reservoir 505.) Glass frit 502 is equilibrated for 30 minutes.
4) Input the above capillary sorption parameters into the computer.
5) Close stopcocks 509 and 510.
6) Move glass frit 502 to the set up height, 100 cm.
7) Place Teflon® ring 562 on surface of glass frit disc 560. Put O-ring 564 on Teflon® ring. Place pre-heated cylinder 566 concentrically on the Teflon® ring. Place test sample 570 concentrically in cylinder 566 on glass frit disc 560. Place piston 568 into cylinder 566. Additional confining weights are placed into piston chamber 590, if required.
8) Cover the glass frit 502 with apertured film.
9) The balance reading at this point establishes the zero or tare reading.
10) Move the glass frit 502 to 200 cm.
11) Open stopcocks 509 and 510 (stopcock 510 is closed to fluid reservoir 505) and begin balance and time readings.

Glass Frit Correction (blank correct uptake)

Since the glass frit disc 560 is a porous structure, the glass frit (502) capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake (g). The elapsed time at each specified height equals the Blank Time (s).

Evaporation Loss Correction

1) Move the glass frit 502 to 2 cm above zero and let it equilibrate at this height for 30 minutes with open stopcocks 509 and 510 (closed to reservoir 505).
2) Close stopcocks 509 and 510.
3) Place Teflon® ring 562 on surface of glass frit disc 560. Put O-ring 564 on Teflon® ring. Place pre-heated cylinder 566 concentrically on the Teflon® ring. Place piston 568 into cylinder 566. Place apertured film on glass frit 502.
4) Open stopcocks 509 and 510 (closed to reservoir 505) and record balance reading and time for 3.5 hours. Calculate Sample Evaporation (g/hr) as follows:

[balance reading at 1 hr—balance reading at 3.5 hr]/2.5 hr

Even after taking all the above precautions, some evaporative loss will occur, typically around 0.10 gm/hr for both the test sample and the frit correction. Ideally, the sample evaporation is measured for each newly installed glass frit 502.

Cleaning the Equipment

New Tygon® tubing 503 is used when a glass frit 502 is newly installed. Glass tubing 504 and 511, fluid reservoir 505, and balance liquid reservoir 506 are cleaned with 50% Clorox Bleach® in distilled water, followed by distilled water rinse, if microbial contamination is visible.

a. Cleaning After Each Experiment

At the end of each experiment (after the test sample has been removed), the glass frit is forward flushed (i.e., test liquid is introduced into the bottom of the glass frit) with 250 ml test liquid from liquid reservoir 505 to remove residual test sample from the glass frit disc pores. With stopcocks 509 and 510 open to liquid reservoir 505 and closed to balance liquid reservoir 506, the glass frit is removed from its holder, turned upside down and is rinsed out first with test liquid, followed by rinses with acetone and test liquid (synthetic urine). During rinsing, the glass frit must be tilted upside down and rinse fluid is squirted onto the test sample contacting surface of the glass frit disc. After rinsing, the glass frit is forward flushed a second time with 250 ml test liquid (synthetic urine). Finally, the glass frit is reinstalled in its holder and the frit surface is leveled.

b. Monitoring Glass Frit Performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic Cleaning

Periodically, (see monitoring frit performance, above) the glass frits are cleaned thoroughly to prevent clogging. Rinsing fluids are distilled water, acetone, 50% Clorox Bleach) in distilled water (to remove bacterial growth) and test liquid. Cleaning involves removing the glass frit from the holder and disconnecting all tubing. The glass frit is forward flushed (i.e., rinse liquid is introduced into the bottom of the glass frit) with the frit upside down with the appropriate fluids and amounts in the following order:

1. 250 ml distilled water.
2. 100 ml acetone.
3. 250 ml distilled water.
4. 100 ml 50:50 Clorox®/distilled water solution.
5. 250 ml distilled water.
6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm, the capillary absorption efficiency can be calculated at the specified heights. In addition, the initial effective uptake rate at 200 cm is calculated.

Blank Correct Uptake $$\text{Blank Correct Uptake(g)} = \text{Blank Uptake(g)} - \frac{\text{Blank Time(s)} * \text{Sample Evap.(g/hr)}}{3600 (s/hr)}$$

Capillary Suction Absorbent Capacity ("CSAC")

$$CSAC(g/g) = \frac{\text{Sample Uptake(g)} - \frac{\text{Sample Time(s)} * \text{Sample Evap. (g/hr)}}{3600 s/hr} - \text{Blank Correct Uptake(g)}}{\text{Dry Weight of Sample(g)}}$$

Initial Effective Uptake Rate at 200 cm ("IEUR")

$$IEUR(g/g/hr) = \frac{CSAC \text{ at } 200 \text{ cm}(g/g)}{\text{Sample Time at } 200 \text{ cm}(s)}$$

Reporting

A minimum of two measurements should be taken for each sample and the uptake averaged at each height to calculate Capillary Sorption Absorbent Capacity (CSAC) for a given storage absorbent member or a distribution material.

With these data, the respective values can be calculated:

The Capillary Sorption Desorption Height at which the material has released x% of its capacity achieved at 0 cm (i.e. of CSAC 0), (CSDH x) expressed in cm;

The Capillary Sorption Absorption Height at which the material has absorbed y % of its capacity achieved at 0 cm (i.e. of CSAC 0), (CSAH y) expressed in cm;

The Capillary Sorption Absorbent Capacity at a certain height z (CSAC z) expressed in units of g {of fluid}/g {of material}; especially at the height zero (CSAC 0), and at heights of 35 cm, 40 cm, etc.

The Capillary Sorption Absorption Efficiency at a certain height z (CSAE z) expressed in %, which is the ratio of the values for CSAC 0 and CSAC z.

A further parameter relates to the amount of liquid, which is loosely bound in a materials, in particular in a distribution material. This Loosely Bound Liquid Capacity (LBLC) is determined by the difference of (1) the Capillary Sorption Desorption Capacity at 0 cm (CSDC 0), and (2) the Capillary Sorption Desorption Capacity at 100 cm (CSDC 100). Any liquid that is not released in a desorption experiment at a pressure of at least 100 cm is called Tightly Bound Liquid (TBLC). The TBLC of a material equals that CSDC100 of that material. It will also be readily understood, that the Capillary Sorption Desorption Capacity at 0 cm is equivalent to the Capillary Sorption Absorption Capacity at 0 cm.

Accordingly, yet another parameter can be defined relating to the desorption pressure (i.e. height) when 50% of this LBLC is released. This is the Capillary Sorption Desorption Release Height when 50% of said LBLC are released (CSDRH 50).

If two materials are combined (such as the first being used as acquisition/distribution material, and the second being used as liquid storage material), the CSAC value (and hence the respective CSAE value) of the second material can be determined relative to the CSDH x value of the first material.

Distribution Region Requirements

Whilst the required properties of well functioning materials or members in one region are depending on properties of the absorbent members or materials in the other region, the following characteristics have been found to provide suitable distribution members.

Fluid distribution materials in the context of the present invention are materials for applications such as in absorbent articles, which are intended to support the fluid transport mechanisms in such articles. Such articles generally have two centerlines, a longitudinal and a transverse one. The term "longitudinal" as used herein, refers to a line axis or direction in the plane of the article, that is generally aligned with (e.g. approximately parallel to) a vertical plane which bisects a standing wearer of such an article into left and right body halves. The fluid transport mechanisms may then be required to effectively use absorbent material which can be spread in the article over a larger region than the loading regions, i.e. this region of the articles where bodily discharges are disposed onto the surface of the absorbent article. Such transport can occur through driving forces such as gravity, which will not allow fluid distribution against the direction of the gravity, and hence often not satisfy requirements as set out for absorbent articles, whereby fluid needs to be transported from the loading point, where discharged fluids are discharged onto the absorbent article, to other parts of the article, which are positioned "higher", i.e. upwards against the direction of gravity.

This wicking is generally achieved by exploiting capillary forces, and can be best assessed by testing the materials in the vertical orientation, i.e. positioning these along the direction of gravity.

Equally important, however, is the amount of fluid which has to be transported. Characteristic loading for baby diapers can be more than 300 ml of urine loading, in voidings often at 75 ml per voiding, and voiding rates of up to 15 ml/sec. Hence the need for the ability to transport significant amounts becomes obvious. There is, however, a further need for low material usage both due to economical use of materials and due to comfort and fit requirements for the wearer. Hence, preferred materials allow transport of large amounts of fluids in short times through a small cross section of such material. This can generally be expressed by the "Vertical Wicking Flux" parameter such as measured by Vertical Wicking Test as described hereinafter, being defined by the cumulative amount of fluid being transported to a given height through a certain cross-section of material in a certain time, expressed in ml/cm²/sec, and by the time the fluid front penetrates up to a certain height in the material against gravity.

These parameters can be easiest determined by using the vertical wicking test, such as specified below, measuring the ability of a material to transport fluid through its internal voids (such as pores) at constancy or absence of external forces, such as gravity or centrifugal forces. Essentially, a specimen of the material is placed in a vertical position extending out of a fluid reservoir. The transport against the gravity can be monitored by measuring both the upward movement of the wetting front and the amount of fluid which is picked up by the material.

Wicking height can be easily increased by decreasing the effective pore size of the distribution material, according to the generally known Lucas-Washburn relationship for capillary systems, which often has been applied to also approximate porous systems. For a given fluid—for example urine or menstrual fluid—and a certain material exhibiting a certain surface energy, the required capillary (or pore) diameter can be approximated to allow wicking up to a certain required height. Obviously, when aiming for large wicking heights, this relation requires small capillary diameter.

However, such small capillaries are not able to handle high amounts fluid, and the cumulative flux for such fluids through such a material with small pores is significantly reduced. This is caused by the high internal friction (or low permeability) that is linked to small pores (according to the Hagen-Poisseuille relationship).

Thus, the preferred distribution material can be described by having a cumulative flux of more than 0.02 g/cm²/min at 15 cm height, preferably more than 0.04 g/cm²/min, even more preferably of more than 0.07 g/cm²/sec, and most preferably of more than 0.14 g/cm²/min.

Whilst flux is one parameter to consider suitable distribution materials, the permeability of the webs is a further important property. Preferably, the distribution materials or members have a sufficiently open structure by having a permeability at 100% saturation, k(100),of a value of more than about 1 Darcy, preferably more than about 2 Darcy, even more preferably more than 8 Darcy or even more than 100 Darcy. Even further, these materials not only exhibit good permeability values when they are saturated, but they also when they are not completely saturated, i.e. have a permeability at 50% of their saturation, k(50), which is more than about 14% of the permeability at 100% saturation, k(100), preferably more than about 18%, even more preferably more than about 25% or even more than about 35% and/or a permeability at 30% of their saturation, k(30), which is more than about 3.5% of the permeability at saturation, even more preferably more than about 5%, or even more than 10%.

Certain materials suitable for the present invention have a specific behavior of being thin when being dry (such as during manufacturing of the article), and increasing in thickness when being wetted (such as being loaded with liquid during use). Such materials have preferably an expansion factor (i.e. the caliper of a layer of material compared in its dry state and in its wet state) of at least 4, preferably of at least 5 and even more preferably of at least 10, and even more preferably of at least 15. In a further aspect it is preferred that such materials also can reduce their caliper after being wetted such as during use, when the liquid is picked up by the ultimate liquid storage medium. Thus, these materials preferably re-collapse when being drained with the same factor as the expansion factor.

Further essential properties of the materials useful for the present invention can be assessed in the "Capillary Sorption Test" as described before, relating to the ability of a material to hold or release fluid as a function of the capillary pressure acting on the fluid, such as gravitational forces.

In order to ensure, that the fluid can be readily transferred from the voids of the upper storage region to the distribution layer immediately after the gush, the fluid distribution materials useful for the present invention have the ability of absorbing 30% of their maximum capacity (i.e. the capacity at 0 cm height) at a height of at least 35 cm as measured in the capillary sorption test.

However, preferred executions of the distribution material do not hold the liquid too strongly, such that it can be released to the ultimate storage regions—either within the previously wetted region, which can the retain the liquid tightly in the smaller pore portion of the material, or in a more remote storage region, which has not been loaded with the liquid during the gush. Thus, the distribution material should exhibit a Capillary Sorption Desorption Height for 50% of its maximum capacity (i.e. the capacity at 0 cm height) of less than 150 cm.

Materials Suitable to Achieve Distribution Requirements

Fluid distribution members suitable for being used in the present invention, can comprise various materials and can be made by various processes. A suitable member can be a web comprising resilient fibers, which are formed into this web by well known processes, such as air-laying, or wetlaying and the like. A wide variety of resilient fibers can be envisaged to perform well in members according to the present invention. Apart from well know synthetic fibers such as being based on polyethyleneterephtalate, polyester, polyamine, resilient polyolefins or combinations thereof e.g. in bi-component fiber form, a particularly preferred fiber is a chemically-stiffened, twisted bulking cellulosic fiber.

Stiffened cellulose fibers can be prepared by internally crosslinking such fibers in relatively dehydrated form while or after such fibers are being or have been dried and defibrated,(i.e., "fluffed") as described in U.S. patent application Ser. No. 304,925 now U.S. Pat. No. 4,898,642. It is not, however, meant to necessarily exclude other hydrophilic, chemically stiffened, twisted, and curled fibers from this invention, such other fibers being described in (but, not limited to) the previously mentioned U.S. Pat. Nos. 3,224,926, 3,440,135, 4,035,147, and 3,932,209. Other non-chemical means of providing stiffened, twisted, and curled cellulose fibers are also contemplated as being within the scope of the present invention, such as high consistency (generally greater than about 30%) mechanical treatment (e.g., frotapulping and/or refining, etc.). Such methods are described in greater detail in U.S. Pat. Nos. 4,976,819 and 5,244,541, issued Dec. 11, 1990 and Sep. 14, 1993, respectively, to Mary L. Minton and entitled "Pulp Treatment Methods".

Other preferred webs further can comprise a second type of fibers having a relatively high surface area. Whilst also synthetic fibers such as having a very small diameter ("microfibers") or having a special surface configuration are contemplated to be suitable, a presently preferred fiber for this high surface application is the eucalyptus family of wood pulp fibers. Eucalyptus provides desirable capillary pressure characteristics in combination with the chemically stiffened, twisted, and curled fibers and will not easily pass through the forming screen, as does a significant amount of the cellulose fines described below. Particularly suitable eucalyptus fibers include those of the eucalyptus grandis species.

When resilient fibers such as the crosslinked, twisted, stiffened fibers are combined with high surface area fibers as described above, the resulting web can have significantly reduced tensile strength, particular in a wet condition. Therefore, in order to facilitate processing and provide product-specific mechanical properties, in both wet and dry states, a binding means can be integrally incorporated into or onto the web. This can be done by adding the binding means to pulp prior to web formation, by applying the binding means to a wetlaid web after deposition on a forming wire, and before drying, after drying, or a combination thereof.

Alternatively to the fibrous webs as described hereinbefore, relatively open-celled polymeric foams can be used, in particular hydrophilic, flexible polymeric foam structures of interconnected open-cells.

For such foams, the mechanical strength of the foam can be such that, upon giving up its liquid, the foam collapses under the capillary pressures involved. The collapse process reduces the effective foam capacity by a substantial factor related to the density of the foam, as is described hereinafter. The collapse, if relatively uniform throughout the structure, also reduces the amount of liquid held in place at the point of liquid insult. In this regard, the strength of the foam material is less than the capillary pressure exerted by the storage component such that the foams will collapse when the aqueous liquids are removed by the storage component of the core. Capillary pressure is controlled herein primarily by adjusting foam cell size (which relates inversely to surface area per unit volume). Strength is controlled by the combination of crosslink density and foam density, which can be expressed as crosslink density per unit volume as defined hereinafter. The type of crosslinker and other comonomers can also be influential.

Polymeric foams useful herein are those which are relatively open-celled. The cells in such substantially open-celled foam structures have intercellular openings or "windows" that are large enough to permit ready liquid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts". The strength of the webs is depending—inter alia—on the thickness, length of the struts, as well as the ratio of the two. For purposes of the present invention, a foam material is "open-celled" if at least 80% of the cells in the foam structure that are at least 1 µm in size are in fluid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants and/or salts left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207 (Dyer et al.) issued Feb. 7, 1995, which is incorporated by reference. Foams which are useful as distribution materials of the present invention are generally those which exhibit an adhesion tension value of from about 15 to about 65 dynes/cm, more preferably from about 20 to about 65 dynes/cm, as determined by capillary suction uptake of synthetic urine having a surface tension of 65±5 dynes/cm.

The skilled artesian will recognize that a wide variety of polymeric open celled foams are useful for the present invention. The following two chapters describe two generic classes of above foams which are particularly preferred for use in the present invention with the first class comprising foams that have especially high flux and the second class are foams having particularly high CSAH30. Other polymeric foams having combination of both properties might be especially useful.

i) Polymeric Distribution Foams Having a High Wicking Flux

An important aspect of these high wicking flux foams is their glass transition temperature (Tg). The Tg represents the midpoint of the transition between the glassy and rubbery states of the polymer. Foams that have a higher Tg than the temperature of use can be very strong but can also be very rigid and potentially prone to fracture. Such foams also tend to expand slowly at the lower in-use temperature, and can creep under stress or be poorly resilient when used at temperatures colder than the Tg of the polymer. The desired combination of mechanical properties, specifically strength and resilience, typically necessitates a fairly selective range of monomer types and levels to achieve these desired properties.

For high wicking flux foams useful for the present invention, the Tg should be as low as possible, so long as the foam has acceptable strength at the intended in-use temperature. Accordingly, monomers are selected as much as possible that provide corresponding homopolymers having lower Tg's.

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean transition is incomplete at in-use temperatures. Typically, if the transition is incomplete at the in-use temperature, the polymer will evidence greater rigidity and will be less resilient. Conversely, if the transition is completed at the in-use temperature, then the polymer will exhibit faster expansion and recovery from compression. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in U.S. Pat. No. 5,563,179 (Stone et al.) issued Oct. 8, 1996.)

High wicking flux polymeric foams useful for the present invention can be described by a number of parameters.

Foams useful for the present invention are able to wick aqueous liquids to a significant height against the force of gravity, e.g., at least about 15 cm. The column of liquid held within the foam exerts a significant contractile capillary pressure. At a height determined by both the strength of the foam (in compression) and the surface area per unit volume of the foam, the foam will collapse. This height is the Capillary Collapse Pressure (CCP) expressed in cm at which 50% of the volume of the foam at zero head pressure is lost. Preferred distribution foams useful for the present invention will have a CCP of at least about 15 cm, more preferably at least about 20 cm, still more preferably at least about 25 cm or even at least about 70 cm. Typically, the CCP values are within ranges with lower limits of about 15 cm, preferably of about 20 cm or more preferably of about 25 cm, and with upper limits of about 80 cm, preferably 75 cm, more preferably of about 70 cm, or even with typical upper limits of 50, 45 cm or 40 cm.

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Since the cells, and holes between the cells, in a given sample of polymeric foam will not necessarily be of approximately the same size; average cell and hole sizes, i.e., average cell and hole diameters, will often be specified.

Cell and hole sizes are parameters that can impact a number of important mechanical and performance features of the foams, including the liquid wicking properties of these foams, as well as the capillary pressure that is developed within the foam structure. A number of techniques are available for determining the average cell and hole sizes of foams. A useful technique involves a simple measurement based on the scanning electron photomicrograph of a foam sample. The high wicking flux foams useful in accordance with the present invention will preferably have a number average cell size of from about 20 $\mu$m to about 60 tm, and typically from about 30 $\mu$m to about 50 $\mu$m, and a number average hole size of from about 5 $\mu$m to about 15 $\mu$m, and typically from about 8 $\mu$m to about 12 $\mu$m.

"Capillary suction specific surface area" is a measure of the test-liquid-accessible surface area of the polymeric network accessible to the test liquid. Capillary suction specific surface area is determined both by the dimensions of the cellular units in the foam and by the density of the polymer, and is thus a way of quantifying the total amount of solid surface provided by the foam network to the extent that such a surface participates in absorbency.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the Test Methods section of U.S. Pat. No. 5,387,207 supra. Any reasonable alternative method for determining capillary suction specific surface area can also be utilized.

Distribution foams having a high wicking flux useful for the present invention will preferably have a capillary suction specific surface area of at least about 0.01 $m^2$/ml, more preferably at least about 0.03 $m^2$/ml. Typically, the capillary suction specific surface area is in the range from about 0.01 to about 0.20 $m^2$/ml, preferably from about 0.03 to about 0.10 $m^2$/ml, most preferably from about 0.04 to about 0.08 $m^2$/ml. When using materials exhibiting densities in the range of less than 0.05 g/$cm^3$, preferably less than 0.02 g/$cm^3$ and often as low as 0.005 g/$cm^3$, the corresponding CSSSA values expressed in units of $m^2$/g are at least 0.2 $m^2$/g, preferably at least 0.5 $m^2$/g, more preferably more than 0.6 $m^2$/g or even more preferably more than 6 $m^2$/g, and typically between about 0.1 $m^2$/g and 40 $m^2$/g.

"Foam density" (i.e., in grams of foam per cubic centimeter of foam volume in air) is specified herein on a dry basis. The density of the foam, like capillary suction specific surface area, can influence a number of performance and mechanical characteristics of absorbent foams. These include the absorbent capacity for aqueous liquids and the compression deflection characteristics. Foam density will vary according to the state of the foarm. Foams in the collapsed state obviously have higher density than the same foam in the fully expanded state. In general, high wicking flux foams in the collapsed state useful for the present invention have a typical dry density of between about 0.11 g/$cm^3$ and about 0.16 g/$cm^3$.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 supra is one method that can be employed for density determination. Foam density pertains to the weight per unit volume of a washed foam free of emulsifiers, fillers, surface treatments such as salts, and the like. The foams useful for the present invention will preferably have dry densities within ranges with lower limits of 8 mg/$cm^3$, preferably of 11 mg/$cm^3$ and more preferably of 13 mg/$cm^3$, and with upper limits of 77 mg/$cm^3$, preferably of 63 mg/$cm^3$, more preferably of 50 mg/$cm^3$, even more preferably of 48 mg/$cm^3$, and most preferably of 30 mg/$cm^3$.

High wicking flux foams useful for the present invention can be obtained by polymerizing a specific type of water-in-oil emulsion or HIPE having a relatively small amount of an oil phase and a relatively greater amount of a water phase. This process comprises the steps of:

A) forming a water-in-oil emulsion at a specified temperature and under specified shear mixing from:
    1) an oil phase comprising:
        a) from about 85 to about 98% by weight of a monomer component capable of forming a copolymer having a Tg of about 35° C. or lower, the monomer component comprising:
  i) from about 30 to about 80% by weight of at least one substantially water-insoluble monofunctional monomer capable of forming an atactic amorphous polymer having a Tg of about 25° C. or lower;
  ii) from about 5 to about 40% by weight of at least one substantially water-insoluble monofunctional comonomer capable of imparting toughness about equivalent to that provided by styrene;
  iii) from about 5 to about 30% by weight of a first substantially water-insoluble, polyfunctional crosslinking agent selected from divinyl benzenes, trivinylbenzenes, divinyltoluenes, divinylxylenes, divinyinaphthalenes divinylalkylbenzenes, divinylphenanthrenes, divinylbiphenyls, divinyidiphenyl-methanes, divinylbenzyls, divinylphenylethers, divinyldiphenylsulfides, divinylfurans, divinylsulfide, divinyl sulfone, and mixtures thereof; and
  iv) from 0 to about 15% by weight of a second substantially water-insoluble, polyfunctional crosslinking agent selected from polyfunctional acrylates, methacrylates, acrylamides, methacryl-amides, and mixtures thereof; and
  b) from about 2 to about 15% by weight of an emulsifier component which is soluble in the oil phase and which is suitable for forming a stable water-in-oil emulsion, the emulsion component comprising: (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ fatty alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers in a weight ratio of primary to secondary emulsifier of from about 50:1 to about 1:4; and
  2) a water phase comprising an aqueous solution containing: (i) from about 0.2 to about 20% by weight of a water-soluble electrolyte; and (ii) an effective amount of a polymerization initiator;
  3) a volume to weight ratio of water phase to oil phase in the range of from about 12:1 to about 125:1; and
B) polymerizing the monomer component in the oil phase of the water-in-oil emulsion to form a polymeric foam material; and
C) optionally dewatering the polymeric foam material.

The process allows the formation of these high wicking flux absorbent foams that are capable of distributing liquids as a result of having carefully balanced properties as described herein. These properties are achieved by careful selection of crosslinker and monomer types and levels and emulsion formation parameters, specifically the amount of shear mixing, the temperature, and the water-to-oil ratio (which translates into the final density of the dry foam).

High wicking flux polymeric foams useful for the present invention can be prepared by polymerization of certain water-in-oil emulsions having a relatively high ratio of water phase to oil phase commonly known in the art as "HIPEs". Polymeric foam materials which result from the polymerization of such emulsions are referred to hereafter as "HIPE foams". A detailed description of the general preparation of such HIPEs is given in U.S. Pat. No. 5,563,179 and U.S. Pat. No. 5,387,207, infra.

The relative amounts of the water and oil phases used to form the HIPEs are, among many other parameters, important in determining the structural, mechanical and performance properties of the resulting polymeric foams. In particular, the ratio of water to oil ("W:O ratio") in the emulsion varies inversely with ultimate foam density and can influence the cell size and capillary suction specific surface area of the foam and dimensions of the struts that form the foam. The emulsions used to prepare the HIPE foams useful for this invention will generally have a volume to weight ratio of water phase to oil phase in the range of from about 12:1 to about 125:1, and most typically from about 15:1 to about 90:1. Particularly preferred foams can be made from HIPEs having ratios of from about 20:1 to about 75:1.

The major portion of the oil phase of the HIPEs will comprise monomers, comonomers and crosslinking agents such as those enumerated in U.S. Pat. No. 5,387,207 infra. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase is an emulsifier component that permits the formation of stable HIPEs. This emulsifier component comprises a primary emulsifier and optionally a secondary emulsifier, such as those enumerated in U.S. Pat. No. 5,387,207 infra.

The oil phase used to form the HIPEs comprises from about 85 to about 98% by weight monomer component and from about 2 to about 15% by weight emulsifier component. Preferably, the oil phase will comprise from about 90 to about 98% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al.), issued Mar. 1, 1994, which is incorporated by reference. Another preferred optional component is an antioxidant such as a Hindered Amine Light Stabilizer (HALS) and Hindered Phenolic Stabilizers (HPS) or any other antioxidant compatible with the initiator system to be employed. Other optional components include plasticizers, fillers, colorants, chain transfer agents, dissolved polymers, and the like.

The discontinuous water internal phase of the HIPE is generally an aqueous solution containing one or more dissolved components such as those enumerated in U.S. Pat. No. 5,387,207 infra. One essential dissolved component of the water phase is a water-soluble electrolyte. The dissolved electrolyte minimizes the tendency of the monomers, comonomers and crosslinkers that are primarily oil soluble to also dissolve in the water phase.

This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

The HIPEs will also typically contain a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

The polymer forming the HIPE foam structure will preferably be substantially free of polar functional groups. This means the polymeric foam will be relatively hydrophobic in character. These hydrophobic foams can find utility where the absorption of hydrophobic liquids is desired. Uses of this sort include those where an oily component is mixed with water and it is desired to separate and isolate the oily component, such as in the case of marine oil spills.

When these foams are to be used as absorbents for aqueous liquids such as juice spills, milk, and the like for clean up and/or bodily liquids such as urine, they generally require further treatment to render the foam relatively more hydrophilic. Hydrophilization of the foam, if necessary, can generally be accomplished by treating the HIPE foam with a hydrophilizing surfactant in a manner described in U.S. Pat. No. 5,387,207 infra.

These hydrophilizing surfactants can be any material that enhances the water wettability of the polymeric foam surface. They are well known in the art, and can include a variety of surfactants, preferably of the nonionic type, such as those enumerated in U.S. Pat. No. 5,387,207 infra.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing surfactant is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%.

Treatment of these relatively hydrophobic foams with hydrophilizing surfactants (with or without hydratable salts) will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the internal polymerized foam surfaces will be suitably hydrophilic, and will include residual water-phase liquid containing or depositing sufficient amounts of calcium chloride, even after the polymeric foams have been dewatered to a practicable extent.

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/hydratable salt, and 4) thereafter dewatering this polymeric foam structure. The procedure is described more fully in U.S. Pat. No. 5,387,207 supra.

The polymeric foams useful herein are preferably prepared in the form of collapsed (i.e., unexpanded), polymeric foams that, upon contact with aqueous liquids, absorb such liquids and expand when the amount absorbed lowers the combined capillary pressure plus confining pressure to below the expansion pressure (described below) of the foam. These collapsed polymeric foams are usually obtained by expressing the water phase from the polymerized HIPE foam through compressive forces, and/or thermal drying and/or vacuum dewatering. After compression, and/or thermal drying/vacuum dewatering, these polymeric foams are in a collapsed, or unexpanded state.

Figure 3:
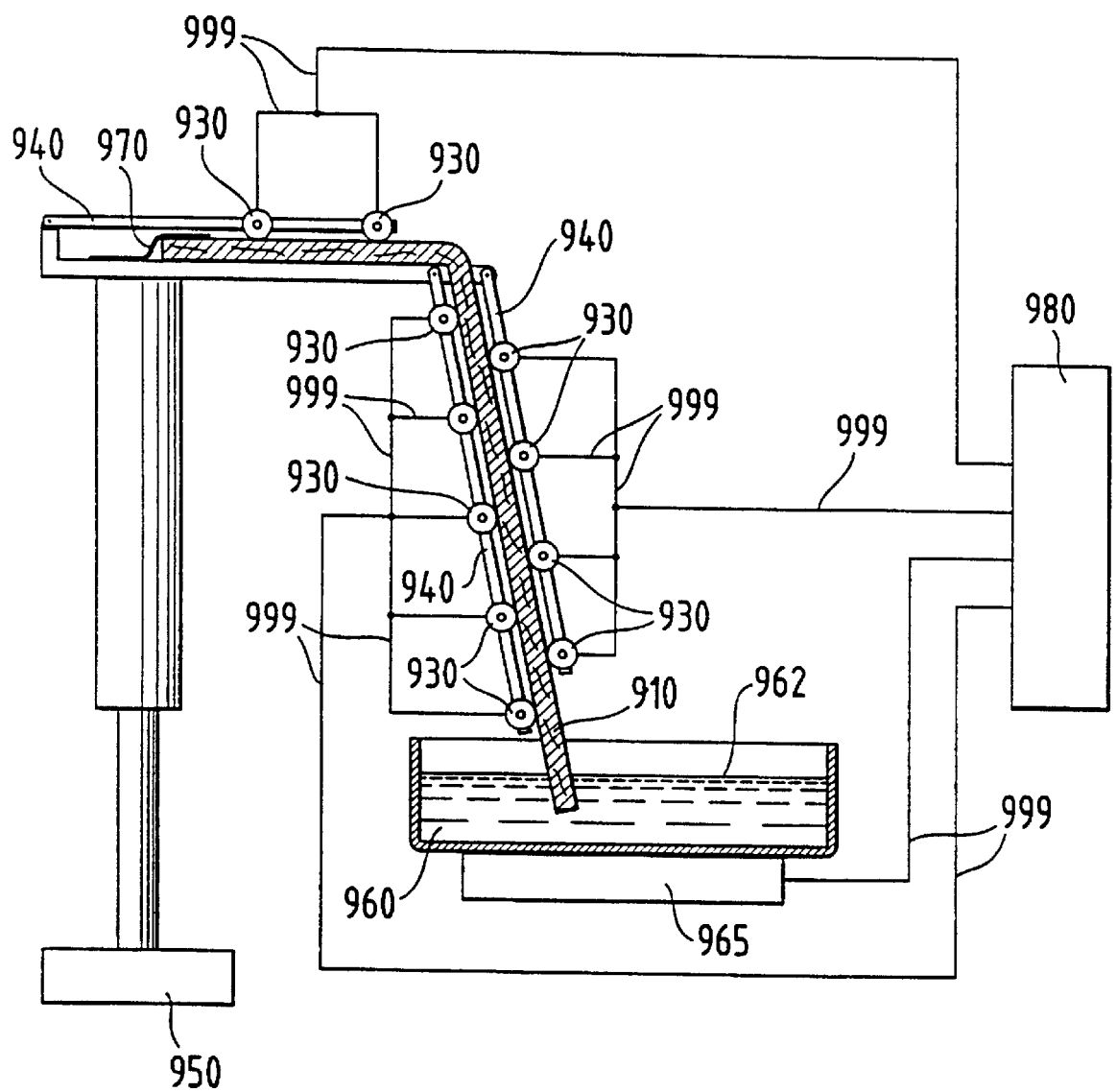
FIG. 3—Vertical Wicking flex Test stand

The cellular structure of a representative collapsed HIPE foam from which water has been expressed by compression is shown in the photomicrograph of FIGS. 3 and 4 of U.S. Pat. No. 5,650,222, discussed above. As shown in these figures, the cellular structure of the foam is distorted, especially when compared to the expanded HIPE foam structures shown in FIGS. 1 and 2 of the '222 patent. As can also be seen in FIGS. 3 and 4 of the '222 patent, the voids or pores (dark areas) in the collapsed foam structure have been flattened or elongated. (It is noted that the foams depicted in the '222 patent are in sheet form; as discussed below, while foams in sheet forms are useful herein, in a alternative embodiment, the foam will be in particulate form.) The preparation of this particular foam and related foams are described herein in Examples 2 through 4, and these very high surface area foams are described in more detail in U.S. patent application Ser. No. 09/042,429, filed Mar. 13, 1998 by T. A. DesMarais et al. titled "HIGH SUCTION POLYMERIC FOAM MATERIALS", now U.S. Pat. No. 6,083,211 and U.S. patent application Ser. No. 09/042,418, filed Mar. 13, 1998 by T. A. DesMarais et al. titled "ABSORBENT MATERIALS FOR DISTRIBUTING AQUEOUS LIQUIDS", now U.S. Pat. No. 6,013,589 the disclosure of each of which is incorporated by reference herein.

Following compression and/or thermal drying/vacuum dewatering, the collapsed polymeric foam may reexpand when wetted with aqueous liquids. Surprisingly, these polymeric foams remain in this collapsed, or unexpanded, state for significant periods of time, e.g., up to at least about 1 year. The ability of these polymeric foams to remain in this collapsed/unexpanded state is believed to be due to capillary forces, and in particular the capillary pressures developed within the foam structure. As used herein, "capillary pressures" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.]

After compression, and/or thermal drying/vacuum dewatering to a practicable extent, these polymeric foams have residual water that includes both the water of hydration associated with the hygroscopic, hydrated salt incorporated therein, as well as free water absorbed within the foam. This residual water (assisted by the hydrated salts) is believed to exert capillary pressures on the resulting collapsed foam structure. Collapsed polymeric foams of the present invention can have residual water contents of at least about 4%, typically from about 4 to about 40%, by weight of the foam when stored at ambient conditions of 72° F. (22° C.) and 50% relative humidity. Preferred collapsed polymeric foams have residual water contents of from about 5 to about 30% by weight of the foam.

ii) Polymeric Distribution Foams Having a High Capillary Sorption Absorption Height (CSAH)

A key parameter of these high CSAH foams is their glass transition temperature. The Tg represents the midpoint of the transition between the glassy and rubbery states of the polymer. Foams that have a higher Tg than the temperature of use can be very strong but will also be rigid and potentially prone to fracture. Such foams also typically take a long time to recover to the expanded state when wetted with aqueous liquids colder than the Tg of the polymer after having been stored in the collapsed state for prolonged periods. The desired combination of mechanical properties, specifically strength and resilience, typically necessitates a fairly selective range of monomer types and levels to achieve these desired properties.

For high CSAH foams useful in the present invention, the Tg should be as low as possible, so long as the foam has acceptable strength at in-use temperatures. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression when wetted with aqueous liquids. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in the Test Methods section of U.S. Pat. No. 5,650,222).

The high surface area polymeric foams useful herein may also be described in terms of their capillary suction specific surface area (hereafter referred to as "CSSSA"). In general, CSSSA is a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer, and is thus a way of quantifying the total amount of solid surface provided by the foam network to the extent that such a surface participates in absorbency. For purposes of characterizing the foams useful herein, CSSSA is measured on a sheet of the foam in question, even where the foam is in particle form when incorporated in a storage absorbent member.

The CSSSA of a foam is particularly relevant to whether the foam will provide the requisite capillary suction for use in preparing storage absorbent members of the present invention. This is because the capillary pressure developed within the foam structure is proportional to the capillary suction specific surface area. In addition, the CSSSA is relevant to whether adequate capillary pressures are developed within the foam structure to keep it in a collapsed state until wetted with aqueous liquids. Assuming other factors such as the foam density and adhesion tension are constant, this means that, as the CSSSA is increased (or decreased), the capillary pressure within the foam structure also increases (or decreases) proportionately.

For purposes of the present invention, CSSSA is determined by measuring the amount of capillary uptake of a low surface tension liquid (e.g., ethanol) which occurs within a foam sample of a known mass and dimensions. A detailed description of such a procedure for determining foam specific surface area is set forth in the Test Methods section of U.S. Pat. No. 5,387,207, which is incorporated by reference. Any reasonable alternative method for determining CSSSA can also be utilized.

The collapsed polymeric high CSAH foams of the present invention useful as absorbents are those that have a CSSSA of at least about 3 $m^2/g$. Typically, the CSSSA is in the range from about 3 to about 30 $m^2/g$, preferably from about 4 to about 17 $m^2/g$, most preferably from about 5 to about 15 $m^2/g$. Foams having such CSSSA values (with expanded state densities of from about 0.010 to about 0.033 $g/cm^3$) will generally possess an especially desirable balance of absorbent capacity, liquid-retaining and liquid-wicking or distribution characteristics for aqueous liquids such as urine. In addition, foams having such CSSSA can develop a sufficient capillary pressure to keep the foam in a collapsed, unexpanded state until wetted with such aqueous liquids.

As discussed above, for particularly preferred high CSAH collapsible polymeric foams, in their collapsed state the capillary pressures developed within the foam structure at least equal the forces exerted by the elastic recovery or modulus of the compressed polymer. In other words, the capillary pressure necessary to keep the collapsed foam relatively thin is determined by the countervailing force exerted by the compressed polymeric foam as it tries to "spring back." The elastic recovery tendency of polymeric foams can be estimated from stress-strain experiments where the expanded foam is compressed to about ⅙ (17%) of its original, expanded thickness and then held in this compressed state until a relaxed stress value is measured. Alternatively, and for the purposes of the present invention, the relaxed stress value is estimated from measurements on the polymeric foam in its collapsed state when in contact with aqueous liquids, e.g., water. This alternative relaxed stress value is hereafter referred to as the "expansion pressure" of the foam. The expansion pressure for collapsed polymeric foams of the present invention is about 50 kilopascals (kPa) or less and typically from about 7 to about 40 kPa. A detailed description of a procedure for estimating the expansion pressure of foams is set forth in the Test Methods section of U.S. Pat. No. 5,387,207.

Another important property of the high CSAH high surface area polymeric foams useful in the present invention is their free absorbent capacity. "Free absorbent capacity" (or "FAC") is the total amount of test liquid (synthetic urine) which a given foam sample will absorb into its cellular structure per unit mass of solid material in the sample. To be especially useful in the storage absorbent members of the present invention, the polymeric foams should have a free absorbent capacity of from about 30 to about 100 ml, preferably from about 30 to about 75 ml of synthetic urine per gram of dry foam material. The procedure for determining the free absorbent capacity of the foam is described hereafter in the Test Methods section of U.S. Pat. No. 5,650,222.

Upon exposure to aqueous liquids, preferred high CSAH collapsed polymeric foams absorb the liquids and expand. The polymeric foams, in their expanded state, absorb more liquid than most other foams. The "expansion factor" for these foams is at least about 4×, i.e. the thickness of the foam in its expanded state is at least about 4 times the thickness of the foam in its collapsed state. The collapsed foams preferably have an expansion factor in the range of from about 4× to about 15×, more preferably from about 5× to about 10×.

For the purposes of the present invention, the relationship between expanded and collapsed thickness for compressively dewatered foams can be empirically predicted from the following equation:

$$\text{thickness}_{expanded} = \text{thickness}_{collapsed} \times ((0.133 \times W{:}O \text{ ratio}) \pm 2)$$

where: $\text{thickness}_{expanded}$ is the thickness of the foam in its expanded state;

$\text{thickness}_{collapsed}$ is the thickness of the foam in its collapsed state;

and W:O ratio is the water-to-oil ratio of the HIPE from which the foam is made. Thus, a typical polymeric foam made from an emulsion with a water-to-oil ratio of 60:1 would have a predicted expansion factor of 8.0, i.e., an expanded thickness 8 times the collapsed thickness of the foam. The procedure for measuring the expansion factor is described hereafter in the Test Methods section of U.S. Pat. No. 5,650,222.

A relevant mechanical feature of the high CSAH high surface area polymeric foams useful in the present invention is their strength in their expanded state, as determined by resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as the high surface area portion of the absorbent members of the present invention, the high CSAH polymeric foams should be suitably resistant to deformation or compression by forces encountered in use. Foams which do not possess sufficient foam strength in terms of RTCD may provide the requisite capillary suction capacity under no-load conditions but will not provide those capacities under the compressive stress caused by the motion and activity of the user of the absorbent articles that contain the foam.

The RTCD exhibited by the polymeric foams useful in the present invention can be quantified by determining the amount of strain produced in a sample of saturated foam held under a certain confining pressure for a specified temperature and period of time. The method for carrying out this particular type of test is described hereafter in the Test Methods section of U.S. Pat. No. 5,650,222. Foams useful herein will preferably exhibit a RTCD such that a confining pressure of 5.1 kPa produces a strain of typically about 90% or less compression of the foam structure when it has been saturated to its free absorbent capacity with synthetic urine having a surface tension of 65±5 dynes/cm. Preferably the strain produced under such conditions will be in the ranges with lower limits of about 1%, preferably of about 2%, and with upper limits of about 90%, preferably about 50%, more preferably about 25%, even more preferably about 10% or even as low as about 5%.

The high surface area high CSAH polymeric foams useful herein can be also be described in terms of their vertical hang sorption height (hereafter "VHSH"). The VHSH height at X % is the height in cm where X % of the 0 cm capacity (or FAC) is retained in the foam. A typical value of importance is the VHSH at 90%, though in principle X may be any value. The most reproducible measure for VHSH is achieved at X=90%, within the experience of the inventors. It will be obvious to one skilled in the art that this single point value does not fully express the shape of the curve obtained in a plot of capacity vs. height. The single point however serves as a practical point of comparison for the foams useful herein. In this regard, the foams will typically have an equilibrium 90% VHSH of at least about 20 cm, preferably at least about 40 cm, still more preferably at least about 60 cm, still more preferably at least about 70 cm and still more preferably at least about 80 cm. Typically, preferred polymeric foams will have a 90% VHSH of from about 20 to about 90 cm, more typically from about 40 or 60 to about 90 cm, more typically from about 70 to about 90 cm, or even from about 80 to about 90 cm. The method for measuring 90% VHSH is described in detail in the Test Methods section below. As indicated, where the high surface area polymeric foam is in particulate form when combined with the other absorbent, such as an osmotic absorbent, 90% VHSH is measured on the corresponding foam in sheet form (i.e., prior to forming particulates). Where the foam is formed into particles (or beads) during the polymerization process, a similar foam can be formed into sheets for assessing the foam's 90% VHSH.

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample.

The cell size measurements given herein are based on the number average cell size of the foam in its expanded state, e.g., as shown in FIG. 1 of U.S. Pat. No. 5,650,222. The foams useful in accordance with the present invention will preferably have a number average cell size of about 80 $\mu$m or less, and typically from about 5 to about 50 $\mu$m.

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 (Dyer et al.) issued Feb. 7, 1995, supra, is one method that can be employed for density determination. In their collapsed state, polymeric foams useful in the present invention have dry basis density values (exclusive of any residual salts and or water) in the range of from about 0.1 to about 0.2 g/cm$^3$, preferably from about 0.11 to about 0.19 g/cm$^3$, and most preferably from about 0.12 to about 0.17 g/cm$^3$. In their expanded state, polymeric foams useful herein will have dry basis density values in the range of from about 0.01 to about 0.033 g/cm$^3$, preferably from about 0.013 to about 0.033 g/cm$^3$.

While high capillary suction high CSAH foams may be in sheet form when combined with other absorbent such as osmotic absorbent (e.g., hydrogel-forming absorbent polymer), in a particularly preferred embodiment, the polymeric foam will be in particle form and will be mixed with particles of hydrogel-forming polymer to provide a blend. That is, while the foam may initially be prepared in sheet form, these sheets may be processed to provide particles of foam which are then combined with the hydrogelling polymer. As discussed above, the foams useful herein, and processes for their preparation, are described in great detail in U.S. Pat. No. 5,387,207, U.S. Pat. No. 5,650,222, U.S. patent application Ser. No. 09/042,429, filed Mar. 13, 1998 by T. A., DesMarais et al. titled "HIGH SUCTION POLYMERIC FOAM MATERIALS" now U.S. Pat. No. 6,073,211 and U.S. patent application Ser. No. 09/042,418, filed Mar. 13, 1998 by T. A. DesMarais et al. titled "ABSORBENT MATERIALS FOR DISTRIBUTING AQUEOUS LIQUIDS," now U.S. Pat. No. 6,013,589. Foam particles may be prepared by first forming a sheet of foam per the teachings of these references, followed by mechanical processing the foam to provide particles (e.g., pulverizing, cutting, chopping, etc.) of the desired dimension. Alternatively, foam particles may be prepared directly from emulsion in the form of polymeric microbeads, as described in U.S. Pat. No. 5,653,922, issued Aug. 5, 1997 to Li et al., and U.S. Pat. No. 5,583,162, issued Dec. 10, 1996 to Li et al., the disclosure of each of which is incorporated by reference herein. Specific embodiments for making polymer foam/hydrogel-forming polymer blends are discussed in more detail below.

Applicants have also found that the high surface area high CSAH foams may optionally comprise a fluid so as to provide increased transfer of urine to the other absorbent or osmotic absorbent of the storage absorbent member. The pre-wetting fluid partially fills the polymeric foam and, without wishing to be held to a particular theory, increases the uptake rate of the foam. Ideally, polymeric foam comprising pre-wetting fluid(s) should be shelf stable, with sufficiently low water activity to prevent microbial growth and prevent evaporative water loss and not migrate out of the foam over time. Water can be used as a pre-wetting fluid to provide the absorption performance but may not by itself meet the other requirements.

Storage Region Member Requirements

In addition to the requirements for the lower distribution region, the storage region has to satisfy certain requirements.

First, the storage region must be able to firmly retain the liquid tightly bound, such as described by the term of ultimate storage capacity, or in terms of the Capillary Sorption Test parameter, by having a Capillary Sorption Desorption Capacity at 100 cm height of at least 10 g/g (dry basis). In order to allow readily releasing of the loosely bound fluid to the underlying distribution layer, the fluid storage region can comprise a material having a Capillary Sorption Desorption Release Height when 50% of the Loosely Bound Liquid Capacity are released (i.e. the CSDRH 50 as defined in the Capillary Sorption Test) of less than 60 cm, preferably less, such as less than 50 cm, even more preferably less than 40 cm, and most preferably less than 30 cm and even less than 20 cm.

A further important property can be measured by the storage member Saline Flow Conductivity (SFC) test. This is relevant for allowing the fluid to flow through the storage member material, particularly when the storage member has no apertures, gaps, or macro voids which could serve as channels for the fluid to by pass the material. Rather, the benefits of the present invention allows the fluid to penetrate through the bulk material of the storage member. Thus, the storage region members or materials must be permeable so as to allow liquid pass through, and this fluid permeability should be maintained from the beginning of the wetting through the end, possibly over several urination cycles. The specific design arrangement of the present invention requires, that the fluid passes through the storage region before it reaches the distribution region to be further distributed into the x, and or y-direction of the article. Henceforth, it is a key requirement for the storage region to be sufficiently permeable to such fluids in the plane of fluid transport (xy direction) in addition of having a high transplanar permeability.

Thus, preferred storage members should exhibit values of at least 25×10-7 cm$^3$sec/g, preferably more than 70×10-7 cm$^3$sec/g, even more preferably more than 100×10-7 cm$^3$seclg or even more than 200×10-7 cm$^3$sec/g, and most preferably more than about 400×10-7 cm$^3$sec/g or even more than 1000×10-7 cm$^3$sec/g.

In addition to the superabsorbent material, the storage region can comprise other materials or members, making a permeable member. It is important, that such members release the fluid readily, either to the distribution layer so as to allow distribution throughout the total absorbent article, or to the increased fluid storage capacity in the ends of the article, or to the superabsorbent of the storage region itself.

Materials to Achieve Storage Region Requirements

Hydrogel-forming Absorbent Polymers

The storage absorbent members of the present invention comprise at least one hydrogel-forming absorbent polymer (also referred to as hydrogel-forming polymer "Superabsorbent material", or "supersorber"). Hydrogel-forming polymers useful in the present invention include a variety of water-insoluble, but water-swellable polymers capable of absorbing large quantities of liquids. Such hydrogel-forming polymers are well known in the art and any of these materials are useful in the absorbent members of the present invention.

Hydrogel-forming absorbent polymer materials are also commonly referred to as "hydrocolloids," or "superabsorbent" materials and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof. As indicated above, the nature of the hydrogel-forming absorbent polymer is not critical to the members of the present invention. Nonetheless, the selection of the optimal polymeric material may enhance the performance characteristics of the present members. The disclosure that follows describes preferred properties of the absorbent polymers useful herein. These properties should not be interpreted as limitations; rather, they merely indicate the progression that has occurred in the absorbent polymer art over the past several years.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chiorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. 4,076,663.

While the hydrogel-forming absorbent polymer is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention. Alternatively, the hydrogel-forming polymer can be a mixture of two or more hydrogel forming polymers such as described in WO 96/01657.

The hydrogel-forming polymer component may also be in the form of a mixed-bed ion-exchange composition comprising a cation-exchange hydrogel-forming absorbent polymer and an anion-exchange hydrogel-forming absorbent polymer. Such polymers can have a particularly well balanced property profile of their absorbency properties, namely Performance Under Pressure values, Saline Flow Conductivity values, and Free Swell Rate. Such mixed-bed ion-exchange compositions as well as the appropriate methods to determine such parameter, are described in, e.g., U.S. patent application Ser. No. 09/003,565, filed Jan. 7, 1998 by Hird, et al. titled "ABSORBENT POLYMER COMPOSITIONS HAVING HIGH SORPTION CAPACITIES UNDER AN APPLIED PRESSURE" now abadoned; U.S. patent application Ser. No. 09/003905, filed Jan. 7, 1998 by Ashraf, et al. titled "ABSORBENT POLYMER COMPOSITIONS WITH HIGH SORPTION CAPACITY AND HIGH FLUID PERMEABILITY UNDER AN APPLIED PRESSURE"; now abadoned and U.S. patent application Ser. No. 09/003,918, filed Jan. 7, 1998 by Ashraf, et al. titled "ABSORBENT POLYMER COMPOSITIONS HAVING HIGH SORPTION CAPACITIES UNDER AN APPLIED PRESSURE AND IMPROVED INTEGRITY IN THE SWOLLEN STATE") now U.S Pat. No. 6,121,509 the disclosure of each of which is incorporated herein by reference. Materials particularly useful for the present invention exhibit high Performance Under Pressure and Saline Flow Conductivity values, and slow Free Swell Rates.

The hydrogel-forming absorbent polymers useful in the present invention can have a a size, shape and/or morphology varying over a wide range. These polymers can be in the form of particles that do not have a large ratio of greatest dimension to smallest dimension (e.g., granules, pulverulents, interparticle aggregates, interparticle crosslinked aggregates, and the like) and can be in the form of fibers, sheets, films, foams, flakes and the like. The hydrogel-forming absorbent polymers can also comprise mixtures with low levels of one or more additives, such as for example powdered silica, surfactants, glue, binders, and the like. The components in this mixture can be physically and/or chemically associated in a form such that the hydrogel-forming polymer component and the non-hydrogel-forming polymer additive are not readily physically separable.

The hydrogel-forming absorbent polymers can be essentially non-porous (i.e., no internal porosity) or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S, Series Alternate Sieve Designation) is considered to have a particle size between 500 and 710 $\mu$m; and a particle that passes through a sieve with 500 micron openings is considered to have a size less than 500 $\mu$m. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et al.), issued Oct. 29, 1991, which is incorporated by reference.

For particles of hydrogel-forming absorbent polymers useful in the present invention, the particles will generally range in size from about 1 to about 2000 $\mu$m, more preferably from about 20 to about 1000 $\mu$m. The mass median particle size will generally be from about 20 to about 1500 $\mu$m, more preferably from about 50 $\mu$m to about 1000 $\mu$m, and even more preferably from about 100 to about 800 $\mu$m.

Where relatively high concentrations (e.g. 40%, 60%, or greater, by weight) of hydrogel forming absorbent polymer are utilized in the absorbent members of the present invention, still other properties of the absorbent polymer may be relevant. In such embodiments, the materials may have one or more of the properties described by U.S. Pat. No. 5,562,646, issued Oct. 8, 1996 to Goldman et al. and U.S. Pat. No. 5,599,335, issued Feb. 4, 1997 to Goldman et al., the disclosure of each of which is incorporated by reference herein.

The basic hydrogel-forming absorbent polymer can be formed in any conventional manner. Typical and preferred processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference.

Preferred methods for forming the basic hydrogel-forming absorbent polymer are those involving aqueous solution or other solution polymerization methods. As described in the above-referenced U.S. Pat. Reissue No. 32,649, aqueous solution polymerization involves the use of an aqueous reaction mixture to carry out polymerization. The aqueous reaction mixture is then subjected to polymerization conditions which are sufficient to produce in the mixture, substantially water-insoluble, slightly network crosslinked polymer. The mass of polymer formed can then be pulverized or chopped to form individual particles.

More specifically, the aqueous solution polymerization method for producing the hydrogel-forming absorbent polymer comprises the preparation of an aqueous reaction mixture in which to carry out the polymerization. One element of such a reaction mixture is the acid group-containing monomer that will form the "backbone" of the hydrogel-forming absorbent polymer to be produced. The reaction mixture will generally comprise about 100 parts by weight of the monomer. Another component of the aqueous reaction mixture comprises a network crosslinking agent. Network crosslinking agents useful in forming the hydrogel-forming absorbent polymer according to the present invention are described in more detail in the above-referenced U.S. Reissue Pat. No. 32,649, U.S. Pat. No. 4,666,983, and U.S. Pat. No. 4,625,001. The network cross-linking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomers, including esters of the essential unsaturated acidic functional group-containing monomers or other co-monomers containing no carboxylic or sulfonic acid functionality at all.

The aqueous reaction mixture is subjected to polymerization conditions which are sufficient to produce in the mixture substantially water-insoluble, but water-swellable, hydrogel-forming absorbent slightly network crosslinked polymers. The polymerization conditions are also discussed in more detail in the three above-referenced patents. Such polymerization conditions generally involve heating (thermal activation techniques) to a polymerization temperature from about 0° to about 100° C., more preferably from about 5° to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the hydrogel-forming absorbent polymer formed in the aqueous reaction mixture are also preferably neutralized. Neutralization can be carried out in any conventional manner that results in at least about 25 mole percent, and more preferably at least about 50 mole percent, of the total monomer utilized to form the polymer being acid group-containing monomers that are neutralized with a salt-forming cation. Such salt-forming cations include, for example, alkali metals, ammonium, substituted ammonium and amines as discussed in further detail in the above-references U.S. Reissue Pat. No. 32,649.

While it is preferred that the particulate versions of hydrogel-forming absorbent polymer be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as described before is suspended in the form of tiny droplets in a matrix of a water-immiscible, inert organic solvent such as cyclohexane. The resultant particles of hydrogel-forming absorbent polymer are generally spherical in shape. Inverse suspension polymerization procedures are described in greater detail in U.S. Pat. No. 4,340,706 (Obaysashi et al.), issued Jul. 20, 1982, U.S. Pat. No. 4,506,052 (Flesher et al.), issued Mar. 19, 1985, and U.S. Pat. No. 4,735,987 (Morita et al.), issued Apr. 5, 1988, all of which are incorporated by reference.

Surface crosslinking of the initially formed polymers is a preferred process for obtaining hydrogel-forming absorbent polymers having relatively high porosity hydrogel-layer ("PHL"), performance under pressure ("PUP") capacity and saline flow conductivity ("SFC") values, which may be beneficial in the context of the present invention. Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992; all of which are incorporated by reference. See also, U.S. Pat. No. 5,562,646 (Goldman et al.), issued Oct. 8, 1996, and U.S. Pat. No. 5,599,335 (Goldman et al.), issued Feb. 4, 1997.

The hydrogel-forming absorbent polymer particles prepared according to the present invention are typically substantially dry. The term "substantially dry" is used herein to mean that the particles have a liquid content, typically water or other solution content, less than about 50%, preferably less than about 20%, more preferably less than about 10%, by weight of the particles. In general, the liquid content of the hydrogel-forming absorbent polymer particles is in the range of from about 0.01% to about 5% by weight of the particles. The individual particles can be dried by any conventional method such as by heating. Alternatively, when the particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer can then be chopped or pulverized to form substantially dry particles of the hydrogel-forming absorbent polymer.

Whilst materials as described in the above can satisfy the requirements as such (e.g. a pure hydrogel forming material, or a pure foam material), preferred members for being used as storage absorbent member comprise two or more of the materials. This allows often to utilize materials which on their own do not satisfy the criteria, but the combination does.

The principle function of such fluid storage members is to absorb the discharged body fluid either directly or from other absorbent members (e.g., fluid acquisition/distribution members), and then retain such fluid, even when subjected to pressures normally encountered as a result of the wearer's movements.

The amount of hydrogel-forming absorbent polymer contained in the absorbent member may vary significantly. Furthermore, the concentration of hydrogel may vary throughout a given member. In other words, a member may have regions of relatively higher and relatively lower hydrogel concentration.

In measuring the concentration of hydrogel-forming absorbent polymer in a given region of an absorbent member, the percent by weight of the hydrogel-forming polymer relative to the combined weight of hydrogel-forming polymer and any other components (e.g., fibers, polymeric foams, etc.) that are present in the region containing the hydrogelling polymer is used. With this in mind, the concentration of the hydrogel-forming absorbent polymers in a given region of an absorbent member of the present invention can be at least about 10%, and will preferably be at least about 40%, more preferably at least about 50%, or even at least about 60%, even more preferably at least about 70%, or even at least about 80%, possibly even up to essentially pure (100%) by total weight of the absorbent storage member.

As another example of a material that will provide integrity of the mixture, in absorbent members comprising a blend of hydrogel-forming polymer and particulate polymeric foam, the member can comprise a thermoplastic material. Upon melting, at least a portion of this thermoplastic material migrates to the intersections of the respective member components, typically due to interparticle or interfiber capillary gradients. These intersections become bond sites for the thermoplastic material. When cooled, the thermoplastic materials at these intersections solidify to form the bond sites that hold the matrix of materials together.

Optional thermoplastic materials useful herein can be in any of a variety of forms including particulates, fibers, or combinations of particulates and fibers. Thermoplastic fibers are a particularly preferred form because of their ability to form numerous bond sites. Suitable thermoplastic materials can be made from any thermoplastic polymer that can be melted at temperatures that will not extensively damage the materials that comprise absorbent member. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One preferred thermoplastic binder fiber is PLEXAFIL® polyethylene microfibers (made by DuPont) that are also available as an about 20% blend with 80% cellulosic fibers sold under the tradename KITY-HAWK® (made by Weyerhaeuser Co.) Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Connecticut. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining; the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, pdlypropylenelpolyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CEL-BOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thickness. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long, and most preferably from about 0.6 to about 1.2 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective absorbent members during preparation of the absorbent core.

Other Fluid Handling Member Components and Materials

In addition to the above described fluid distribution and fluid storage member, articles according to the present invention can comprise further fluid handling members and other components.

In particular, there can be members positioned between the topsheet and the storage region which aim at improving the acquisition functionality of the absorbent article, with regard to urine, and or to feces. Such members are well known to the person skilled in the art in the form of fibrous layers, or open pore foam regions, or and are described such as in our cases CM1096, EP Application No. 96111895.7, CM1453, PCT Application No. PCT/US97/05046, CM1640, PCT Application No. PCT/US97/20842, CM1642, PCT Application No. PCT/US97/20840, CM1643, PCT Application No. PCT/US97/20701, CM1809, EP Application No. 98110154.6, CM1879, EP Application No. 98114190.6, all of which are incorporated herein by reference.

Articles according to the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968, 312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Storage absorbent members according to the present invention can include other optional components that can be present in absorbent webs. For example, a reinforcing scrim can be positioned within the storage absorbent member, or between the respective absorbent members of the absorbent core. Such reinforcing scrims should be of such configuration as to not form interfacial barriers to liquid transfer, especially if positioned between the respective absorbent members of the absorbent core. In addition, several binders may be used to provide dry and wet integrity to the absorbent core and/or the absorbent storage member itself. In particular, hydrophilic glue fibers may be used. It is preferred that the amount of binder used is as low as possible, so as not to impair the capillary sorption properties of the absorbent member. However, the skilled artisan will recognize that there are also binders that may enhance the capillary sorption properties of the absorbent member such as fiberized hydrophilic glue with sufficiently high surface area. In this case, the high surface area hydrophilic glue may provide both the liquid handling function and the integrity function, in one material. Also, the respective absorbent member, or the entire absorbent core, can be enveloped within a liquid pervious sheet, such as a tissue paper sheet, to obviate user concern regarding loose particulate absorbent polymer, as long as the capillary continuity is not disturbed.

Other optional components that can be included are materials to control odor, contain fecal matter, etc. Also, any absorbent member comprising particulate osmotic absorbent or high surface area material, or the entire absorbent core, can be enveloped within a liquid pervious sheet, such as a tissue paper sheet, to obviate user concern regarding loose particulate absorbent polymer.

When integrity is introduced via a binder material, suitable binders are melt-blown adhesives such as those described in U.S. Pat. No. 5,560,878, issued Oct. 1, 1996 to Dragoo et al., the disclosure of which is incorporated herein by reference. Processes for combining melt-blown adhesives with the requisite hydrogel-forming polymer and high surface area material is also described in detail in the '878 patent.

Breathable Backsheet Materials

An particular aspect of the present invention is the combination of absorbent structures as described in the above with backsheet materials which are "breathable", i.e. allow passage of gases, such as air, or of vapours, such as water vapour.

The backsheet of the present invention is that portion of the absorbent article which is generally positioned away from the wearer's skin and which prevents the exudates absorbed and contained in the absorbent core from wetting other articles which contact the absorbent article, e.g. a diaper, such as bedsheets and undergarments. Thus, the backsheet should be essentially impervious to fluids (e.g., urine). In addition to being substantially fluid impervious, the backsheet also should be breathable. In particular for disposable diapers, breathability has been found to be critical to performance especially in hot and humid conditions. When an absorbent article is positioned on a wearer, the skin is occluded by the materials making up the absorbent article. This occlusion of the skin, especially in hot and humid conditions, prevents evaporation and the resulting cooling of the occluded area. The resultant perspiration raises the relative humidity of air inside of the absorbent article resulting in less comfort for the wearer and perceived negative benefits by caregivers.

It has been found that the moisture vapor transmission rate of the backsheet is important in reducing the incidence of heat rash and other skin problems associated with high heat and humidity conditions.

The moisture vapor transmission rate can be measured by the method set forth hereinafter, wherein the moisture pick up of $CaCl_2$ through a test specimen from an environment having a constant temperature (40° C.) and humidity (75% RH) for five hours is recorded. The mass vapor transmission rate (MVTR) is calculated and expressed in $g/m^2 24$ hr. using the following formula:

$$MVTR = \frac{(\text{final weight} - \text{initial weight}) \times 24.0}{\text{area of sample in meters} \times 5.0 (\text{time in chamber})}$$

Materials exhibiting a MVTR value of up to about 200 $g/m^2/24$ h can be considered to be essentially non-vapour permeable. This value should be compared to a value of up to 12 000 $g/m^2/24$ h which may be required for covering human skin without providing a significant additional resistance to the moisture transfer away from the skin, or alternatively result when operating the MVTR test without a test material.

There are numerous materials known in the art as "breathable backsheets" such as microporous films or film laminates, nonwovens, including coated non-wovens, plasma tretaed non-wovens, Monolithic films, formed films, such as having apertures with a directional fluid transmission or combinations thereof.

Examples for the so called microporous films can be provided by Mitsui Toatsu Co., Japan under the designation ESPOIR NO. Such films can be made by producing a polymer film such as made from Polythylene, further comprising filler particles, such as Calcium-Carbonate. After having formed a film wherein these filler particles are embedded into a matrix of polymeric material, the film can be mechanically treated so as to strain and stretch the polymeric materials permanently, thereby creating small cracks around the non-deforming filler particles. The cracks are sufficiently small to allow gas molecules of the gas phase to pass through, but prevent liquids from penetrating. Thus the transport mechanisms is slow flow in capillaries.

This deformation can be achieved by a number of different ways, in machine direction of the material such as by conventional stretching between two nip roll arrangements running at a differential speed, or in CD directions such as tentering fixing the edges of the material in diverging frames, or by running it through narrowly intermeshing rolls, or by any combination thereof. Each off these steps can be executed whist the material is heated (i.e. at a temperature exceeding the ambient temperature, i.e. most often at temperature of more than about 40° C.), or "cold", i.e. below said temperature.

The microporosity of such materials can be imparted as an integral process step of the film making process, it can be a separate process step, or it can be a process step which is integrated into further conversion of such materials, such as when using such films to produce absorbent articles.

Other examples are described in U.S. Pat. No. 3,156,242 issued to Crowe, Jr. on Nov. 10, 1964, teaching the use of a microporous film as a breathable backsheet; U.S. Pat. No. 3,881,489, issued to Hartwell on May 6, 1975, describes a breathable backsheet comprising in combination two layers, the first of which is a low void volume perforated thermoplastic film and the second of which is a porous high void volume hydrophobic tissue; U.S. Pat. No. 3,989,867 issued to Sisson on Nov. 2, 1976 teaches a breathable backsheet provided with tapered hollowed bosses which prevent the passage of fluids while allowing vapors to pass readily therethrough.

Other moisture vapor permeable films can comprise materials such a polyamide, polyester, poly-urethane, poly-vinyl-acetate or—alcohol, or can comprise polyether block copolymers, such as described in U.S. Pat. No. 4,493,870.

Other films can comprise a mixture of (a) a block copolyether ester, a block copolyether amide and/or a polyurethane, (b) a thermoplastic homo, co or terpolymer that is incompatible with (a), and (c) a compatibilizer. Such materials are described in PCT application WO 95/16746, published on Jun. 22, 1995 in the name of E. I. DuPont. Composite materials comprising such polymer blends are available from Clopay Corporation, Cincinnati, Ohio under the name HYTREL blend P18-3097. Suitable materials of this type are also described in greater detail in copending PCT publication WO 98/19861, filed on Nov. 6, 1996 in the name of Curro, the disclosure of which is incorporated herein by reference. Such films can be referred to as monolithic film. Such films can pick up certain amounts of water, which can be determined by ASTM-570. Once such materials have picked up a certain amount of water, their permeability for water can actually increase. Thus, such materials can be particularly useful for th present invention, with a liquid distribution layer in direct contact and in liquid communication with such materials, whereby these films are readily wetted by the liquid discharged to the article, and this is happening—due to the spreading and distribution properties of the distribution region—over a relatively large are of the absorbent article.

When using plastic film materials, it has often been found, that the plastic feel is not preferred by consumers. Henceforth, it is often desired to have an improved hand of such materials, which can be achieved—among other ways—by using fibrous materials, such as non-wovens, which have been made liquid impermeable such as by either minimizing the non-woven pore size e.g. by combining spunbonded webs with meltblown layers (SMS) or by other treatments. Further materials can be apertured films whereby these materials can further exhibit a unidirectional liquid impermeability such as described in EP-A-0.710.471.

Such materials often have high or very high permeability values, such as about 4500 g/m$^2$/24 h to 6000 g/m$^2$/24 h for non-woven webs, such that they also can be meaningfully described by the air permeability values, whereby about 1500 to 2500 l/cm$^2$/sec result for conventional SMS materials, 2000 to 2300 l/cm$^2$/sec for common carded webs and more 2500 l/cm$^2$/sec for low basis weight spunbonded webs.

Suitable materials can be obtained by combining a layer of fibrous material, such as a low basis weight non-woven, with a film layer. Such layers can be attached to the film by various methods, such as by using adhesives or by thermally attaching these together, such as described in U.S. Pat. No. 4,725,481, suggesting that films may be attached to a textile fabric by adhesive bonding or melt bonding. However, the cost of making such films and then bonding the films to fibrous textile substrates has been high relative to microporous film laminates. In addition, known moisture vapor permeable films like the films disclosed in U.S. Pat. Nos. 4,725,481 and 5,445,874 do not readily adhere to many common nonwoven substrate materials, such as polyolefin-based nonwoven materials, without the application of a separate adhesive. One notable microporous film composite is made from polytetrafluoroethylene that is adhered to a textile material with an adhesive, as disclosed in British Patent Application No. 2,024,100.

Microporous films adhesively bonded to textile substrates have been used in a variety of apparel products, including absorbent articles, as disclosed in PCT Patent Publication Nos. WO 95/16562 and WO 96/39031.

However, it has been found that these materials have not been sufficiently fluid impervious when subjected to the normal usage conditions, e.g., mechanical impact from an infant sitting down. The ability of a fluid to be forced through such materials during normal usage conditions results in current breathable products exhibiting unwanted transmission of urine waste through the backsheet. Therefore, it would be desirable to provide a backsheet for use on a disposable absorbent article such as a disposable diaper which is not only breathable, i.e., exhibits a MVRR at least about 2000 g/m$^2$/24 hr., but also exhibits substantially zero dynamic fluid transmission when subjected to normal usage conditions, such as when an infant sits down. As the core design of the present invention is designed to distribute liquid through the distribution layer as being on the garment side of the article, and hence can be in direct contact with the backsheet, this potential for fluid transmission is significantly greater, as more and less strongly bound liquid can be in contact with the backsheet. This effect is even further aggravated, when the surface tension of the liquid is reduced when contacting other, surfactant releasing materials on its path from the loading point to the backsheet, thus having a reduced surface tension. This can, however lead to increased liquid transmission though small pores or capillaries.

As used herein, "substantially zero dynamic fluid transmission" includes any measured value less than 0.75 g/m$^2$ when subjecting a material to the dynamic fluid impact test method set forth below.

The dynamic fluid impact test method set forth below is designed to mimic the energy per area that an infant imparts to a diaper backsheet when abruptly going from a standing to a sitting position. While other common infant movements and activities, (e.g., rolling on the ground), may also cause leakage by transmitting urine through the diaper backsheet, the sitting action provides a clear mechanical interaction which can be analyzed to gain a quantitative understanding of the actual impact energies involved in typical diaper usage conditions.

In addition to exhibiting a mass vapor transmission rate of at least about 2000 g/m$^2$/24 hr., suitable materials for the backsheet will also exhibit substantially zero dynamic fluid transmission when subjected to an impact energy of about 1000 joules/m$^2$. Preferably, the backsheets of the present invention while exhibiting a mass vapor transmission rate of at least about 2000 g/m$^2$/24 hr. will also exhibit substantially zero dynamic fluid transmission when subjected to impact energies of about 2000 joules/m$^2$, about 3000 joules/m$^2$, and about 4000 joules/m$^2$. Backsheets of the present invention may exhibit substantially zero dynamic fluid transmission when subjected to even higher impact energies, e.g., impact energies of at least about 5000 joules/m$^2$ or greater.

Suitable backsheet materials which exhibit substantially zero dynamic fluid transmission when subjected to an impact energy of about 1000 joules/m$^2$ and also exhibit a mass vapor transmission rate of at least about 2000 g/m$^2$/24 hr. include a single layer monolithic film capable of passing sufficient moisture vapor such as a polyester based film or may comprise two or more layers such as a polyester-based film extrusion coated onto a nonwoven web. Furthermore, the backsheet may comprise a monolithic film coated microporous material.

Whilst a number of materials are commercially available, such as from Elf Atochem under the trade designation PEBAX®), or from BF Goodrich under the trade designation ESTANE®, the following materials were subjected to the mass vapor transmission rate test and the dynamic fluid impact test described above.

Sample A—Exxon Exxair® XFB-100W available from Exxon Chemical Company of Buffalo Grove, Ill.

Sample B—DuPont Hytrel (Film blend #P18-3709 available from Clopay Corporation, Cincinnati, Ohio.

Sample C—DuPont Hytrel® Film blend #P18-3708 available from Clopay Corporation, Cincinnati, Ohio.

The results of the mass vapor transmission rate test and the dynamic fluid impact test are set forth in Table 1.

TABLE 1

Mass Vapor Transmission Rate (MVTR) and Dynamic Fluid Transmission Value (DFTV)

| Sample | MVTR in g/m$^2$/24 hr. | DFTV in g/m$^2$ at 1000 joules/m$^2$ |
| --- | --- | --- |
| A | 4600 | 2.2 |
| B | 3400 | 0.28 |
| C | 3300 | 0.40 |

As can be seen from Table 1, Samples B and C exhibited substantially zero dynamic fluid transmission when subjected to an impact energy of 1000 joules/m$^2$ and also exhibited a mass vapor transmission rate of at least about 2000 g/m$^2$/24 hr. Samples B and C would thus be suitable for use as a backsheet on a disposable diaper as they would be breathable and sufficiently fluid impervious when subjected to normal usage conditions. Sample A was sufficiently breathable, (i.e., it had mass vapor transmission rates of at least about 2000 g/m$^2$/24 hr.), however, it exhibited an unacceptable degree of dynamic fluid transmission when subjected to an impact energy of 1000 joules/m$^2$.

EXAMPLES

Distribution Materials

The following Samples 1 to 3 and S.2 to S.4 are of the polymeric foam type, and are prepared as described generally in the Examples section of U.S. Pat. No. 5,563,179, supra. Generally, this process comprises appropriate mixing of an aqueous phase containing selected salts with an oil phase containing selected monomers and emulsifiers. The aqueous phase typically contains an initiator such as potassium persulfate and inorganic salt such as calcium chloride. The oil phase typically contains a blend of monomers such as 2-ethylhexylacrylate and crosslinking monomers such as divinyl benzene (which contains ethyl styrene as an impurity) and 1,6-hexanedioldiacrylate. Adjuvants such as antioxidants, opacifying agents, pigments, dyes, fillers, and other generally unreactive chemicals, can also be added to either phase.

The separate streams of the oil phase and water phase (typically heated to between about 30° and about 90° C.) are fed to a dynamic mixing apparatus. Thorough mixing of the combined streams in the dynamic mixing apparatus is achieved by means of a pin impeller. The ratio of the aqueous phase and the oil phase, referred to as the "water-to-oil ratio", or W:O, is used to control the density of the ultimate foam produced. A detailed description of the apparatus and the procedures for establishing the initial HIPE formation is described in more detail in the Examples section of U.S. Pat. No. 5,563,179, supra.

Once the apparatus set-up is filled, agitation is begun in the dynamic mixer, with the impeller turning at a specified RPM. The flow rate of the water phase is then steadily increased to a rate of 44.1 cm$^3$/sec in a time period of about 30 sec. and the oil phase flow rate is reduced to 1.25 g/sec over a time period of about 1 min. The back pressure created by the dynamic and static mixers at this point is typically between about 3 and about 8 PSI (about 21 to about 55 kPa). The impeller speed is then adjusted to the desired RPM over a period of 120 sec. The system back pressure responds to this adjustment and remains constant thereafter.

The HIPE from the static mixer is collected in a round polypropylene tub, 17 in. (43 cm) in. diameter and 7.5 in. (10 cm) high, with a concentric insert made of Celcon plastic. The insert is 5.0 in. (12.7 cm) in diameter at its base and 4.75 in. (12 cm) in diameter at its top and is 6.75 in. (17.1 cm) high. The HIPE-containing tubs are kept in a room maintained at 65° C. for 18 hours to cure and provide a polymeric HIPE foam.

The cured HIPE foam is removed from the tubs. The foam at this point contains residual water phase (containing dissolved emulsifiers, electrolyte, initiator residues, and initiator). The foam is sliced with a sharp reciprocating saw blade into sheets of desired thickness. These sheets are then subjected to compression in a series of 2 porous nip rolls equipped with vacuum which gradually reduces the residual water phase content of the foam to about 2 times (2×) the weight of the polymerized monomers. At this point, the sheets are then resaturated with a 4% $CaCl_2$ solution at 60° C., are squeezed in a series of 3 porous nip rolls equipped with vacuum to a water phase content of about 2×. The $CaCl_2$ content of the foam is between 2 and 10%.

The HIPE foam is then dried in air for about 16 hours or thermally dried continuously. Such drying reduces the moisture content to about 4–20% by weight of polymerized material.

Sample 1

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (39% divinylbenzene and 61% ethyl styrene) (2640 g), 2-ethylhexyl acrylate (4720 g), and hexanedioldiacrylate (640 g) is added a diglycerol monooleate emulsifier (480 g), ditallow dimethyl ammonium methyl sulfate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 600 to its neighboring level with each level separated by .03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in U.S. patent application Ser. No. 08/716,510 (T. A. DesMarais), filed Sep. 17, 1996now U.S. Pat. No. 5,827,909 (herein incorporated by reference).

The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 100-812) has 12 elements with a 1 inch (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 inch (2.5 cm) pipe, 12 element mixer (McMaster-Carr Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 $cm^3$/sec water phase.

Once the apparatus set-up is filled, agitation is begun in the dynamic mixer, with the impeller turning at 850 RPM and recirculation is begun at a rate of about 30 $cm^3$/sec. The flow rate of the water phase is then steadily increased to a rate of 151.3 $cm^3$/sec over a time period of about 1 min., and the oil phase flow rate is reduced to 2.52 g/sec over a time period of about 3 min. The recirculation rate is steadily increased to about 150 $cm^3$/sec during the latter time period. The back pressure created by the dynamic zone and static mixers at this point is about 4.9 PSI (33.8 kPa), which represents the total pressure drop of the system. The Waukesha pump speed is then steadily decreased to a yield a recirculation rate of about 75 $cm^3$/sec.

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 55–65 times (55–65×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are then resaturated with a 4% $CaCl_2$ solution at 60° C., are squeezed in a series of 3 porous nip rolls equipped with vacuum to a water phase content of about 1.5–2×. The $CaCl_2$ content of the foam is between 6 and 10%.

The foam remains compressed after the final nip at a thickness of about 0.027 in. (0.069 cm). The foam is then dried in air for about 16 hours. Such drying reduces the moisture content to about 9–17% by weight of polymerized material. At this point, the foam sheets are very drapeable.

Sample 2

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (640 g), ditallow dimethyl ammonium methyl sulfate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 600 to its neighboring level with each level separated by .03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in U.S. Pat. No. 5,827,909, which is incorporated herein by reference. The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 101-212) normally has 12 elements with a 1.5 inch (3.8 cm) outside diameter, but 7 inches (17.8 cm) were removed to fit in the equipment space. A hose is mounted downstream from the static mixer to facilitate delivery of the emulsion to the device used for curing. Optionally an additional static mixer is used to provide addition back pressure to keep the hose filled. The optional static mixer can be the same as the first without modification.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cm$^3$/sec water phase.

Once the apparatus set-up is filled, agitation is begun in the dynamic mixer, with the impeller turning at 800 RPM and recirculation is begun at a rate of about 30 cm$^3$/sec. The flow rate of the water phase is then steadily increased to a rate of 151.3 cm$^3$/sec over a time period of about 1 min., and the oil phase flow rate is reduced to 2.52 g/sec over a time period of about 3 min. The recirculation rate is steadily increased to about 150 cm$^3$/sec during the latter time period. The back pressure created by the dynamic zone and static mixers at this point is about 4.2 PSI (29 kPa), which represents the total pressure drop of the system.

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 58–62 times (58–62×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% CaCl$_2$ solution at 60° C., are squeezed in a series of 3 porous nip rolls equipped with vacuum to a water phase content of about 2×. The CaCl$_2$ content of the foam is between 3 and 6%.

The foam remains compressed after the final nip at a thickness of about 0.047 in. (0.071 cm). The foam is then dried in air for about 16 hours. Such drying reduces the moisture content to about 9–17% by weight of polymerized material. At this point, the foam sheets are very drapeable.

Sample 3

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a digtycerol monooleate emulsifier (640 g), ditallow dimethyl ammonium methyl sulfate (80 g), and Tinuvin 765 (40 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 21.6 cm in length with a diameter of about 1.9 cm. The shaft holds 6 rows of pins, one level with 3 rows having 21 pins and another level with 3 rows having 21 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 1.4 cm. The pin impeller is mounted in a cylindrical sleeve which forms the dynamic mixing apparatus, and the pins have a clearance of 3 mm from the walls of the cylindrical sleeve.

A minor portion of the effluent exiting the dynamic mixing apparatus is withdrawn and enters a recirculation zone, as shown in the Figure in U.S. Pat. No. 5,827,909, which is incorporated herein by reference. The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 070-821), modified by cutting off 2.4 inches (6.1 cm) of its original length) is 14 inches (35.6 cm) long with a 0.5 inch (1.3 cm) outside diameter.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 1.89 g/sec oil phase and 7.56 $cm^3$/sec water phase.

Once the apparatus set-up is filled, agitation is begun in the dynamic mixer, with the impeller turning at 1000 RPM and recirculation is begun at a rate of about 8 $cm^3$/sec. The flow rate of the water phase is then steadily increased to a rate of 45.4 $cm^3$/sec over a time period of about 1 min., and the oil phase flow rate is reduced to 0.6 g/sec over a time period of about 3 min. The recirculation rate is steadily increased to about 45 $cm^3$/sec during the latter time period. The back pressure created by the dynamic zone and static mixers at this point is about 2.9 PSI (20 kPa), which represents the total pressure drop of the system.

The HIPE flowing from the static mixer at this point is collected in a round polypropylene tub, 17 in. (43 cm) in diameter and 7.5 in (10 cm) high, with a concentric insert made of Celcon plastic. The insert is 5 in (12.7 cm) in diameter at its base and 4.75 in (12 cm) in diameter at its top and is 6.75 in (17.1 cm) high.

The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 70–80 times (70–80x) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 3 times (3x) the weight of the polymerized material. At this point, the sheets are then resaturated with a 1.5% $CaCl_2$ solution at 60° C., are squeezed in a series of 3 porous nip rolls equipped with vacuum to a water phase content of about 2x. The $CaCl_2$ content of the foam is between 3 and 5%.

The foam remains compressed after the final nip at a thickness of about 0.031 in. (0.079 cm). The foam is then dried in air for about 16 hours. Such drying reduces the moisture content to about 9–17% by weight of polymerized material. At this point, the foam sheets are very drapeable.

Sample S.2 Preparation of High Surface Area Foam From a HIPE

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (480 g), ditallow dimethyl ammonium methyl sulfate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure of U.S. patent application Ser. No. 08/716,510, filed Sep. 17, 1996 by DesMarais now U.S. Pat. No. 5,827,909, the disclosure of which is incorporated by reference herein. The Waukesha pump in the recirculation zone returns the minor portion to the entry point of the oil and water phase flow streams to the dynamic mixing zone.

The static mixer (TAH Industries Model 100-812) has 12 elements with a 1 in. (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 in. (2.5 cm) pipe, 12 element mixer (McMaster-Carr, Aurora, Ohio, Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 $cm^3$/sec water phase.

Once the apparatus set-up is filled, agitation is begun in the dynamic mixer, with the impeller turning at 1750 RPM and recirculation is begun at a rate of about 30 $cm^3$/sec. The flow rate of the water phase is then steadily increased to a rate of 151.3 $cm^3$/sec over a time period of about 1 min., and the oil phase flow rate is reduced to 3.03 g/sec over a time period of about 3 min. The recirculation rate is steadily increased to about 150 cm³/sec during the latter time period. The back pressure created by the dynamic zone and static mixers at this point is about 19.9 PSI (137 kPa), which represents the total pressure drop of the system. The Waukesha pump (Model 30) speed is then steadily decreased to a yield a recirculation rate of about 75 cm³/sec.

The HIPE flowing from the static mixer at this point is collected in a round polyethylene tub, 40 in. (102 cm) in diameter and 12.5 in. (31.8 cm) high, with removable sides, much like a springform pan used in cooking cakes. A pipe-like polyethylene insert 12.5 in. (31.8 cm) in diameter at its base is firmly affixed to the center of the base and is 12.5 in. (31.8 cm) high. The HIPE-containing tubs are kept in a room maintained at 65° C. for 18 hours to effect polymerization and form the foam.

The cured HIPE foam is removed from the curing tubs. The foam at this point has residual water phase (containing dissolved emulsifiers, electrolyte, initiator residues, and initiator) about 48–52 times (48–52x) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6x) the weight of the polymerized material. At this point, the sheets are then resaturated with a 1.5% $CaCl_2$ solution at 60° C., are squeezed in a series of 3 porous nip rolls equipped with vacuum to a water phase content of about 4x. The $CaCl_2$ content of the foam is between 8 and 10%.

The foam remains compressed after the final nip at a thickness of about 0.021 in. (0.053 cm). The foam is then dried in air for about 16 hours. Such drying reduces the moisture content to about 9–17% by weight of polymerized material. At this point, the foam sheets are very drapeable and "thin-after-drying".

Sample S.3 Preparation of High Surface Area Foam From a HIPE

The water and oil phase streams to be used in a continuous process for forming a HIPE emulsion is prepared according to Sample S.2. Separate streams of the oil phase (25° C.) and water phase (53°–55° C.) are fed to a dynamic mixing apparatus as detailed in Sample S.2.

Once the apparatus set-up is filled, agitation is begun in the dynamic mixer, with the impeller turning at 1700 RPM and recirculation is begun at a rate of about 30 cm³/sec. The flow rate of the water phase is then steadily increased to a rate of 151.3 cm³/sec over a time period of about 1 min., and the oil phase flow rate is reduced to 3.36 g/sec over a time period of about 3 min. The recirculation rate is steadily increased to about 150 cm³/sec during the latter time period. The back pressure created by the dynamic zone and static mixers at this point is about 19.7 PSI (136 kPa), which represents the total pressure drop of the system. The Waukesha pump speed is then steadily decreased to a yield a recirculation rate of about 75 cm³/sec.

The HIPE flowing from the static mixer at this point is collected and cured into a polymeric foam as detailed in Sample S.2.

The cured HIPE foam is removed from the curing tubs. The foam at this point has residual water phase (containing dissolved emulsifiers, electrolyte, initiator residues, and initiator) about 43–47 times (43–47x) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6x) the weight of the polymerized material. At this point, the sheets are then resaturated with a 1.5% $CaCl_2$ solution at 60° C., are squeezed in a series of 3 porous nip rolls equipped with vacuum to a water phase content of about 4x. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

Sample S.4 Preparation of High Surface Area Foam From a HIPE

The water and oil phase streams to be used in a continuous process for forming a HIPE emulsion is prepared according to Sample S.2. Separate streams of the oil phase (25° C.) and water phase (53°–55° C.) are fed to a dynamic mixing apparatus as detailed in Sample S.2.

Once the apparatus set-up is filled, agitation is begun in the dynamic mixer, with the impeller turning at 1750 RPM and recirculation is begun at a rate of about 30 cm³/sec. The flow rate of the water phase is then steadily increased to a rate of 151.3 cm³/sec over a time period of about 1 min., and the oil phase flow rate is reduced to 3.78 g/sec over a time period of about 3 min. The recirculation rate is steadily increased to about 150 cm³/sec during the latter time period. The back pressure created by the dynamic zone and static mixers at this point is about 18.7 PSI (129 kPa), which represents the total pressure drop of the system. The Waukesha pump speed is then steadily decreased to a yield a recirculation rate of about 75 cm³/sec.

The HIPE flowing from the static mixer at this point is collected and cured into a polymeric foam as detailed in Sample S.2.

The cured HIPE foam is removed from the curing tubs. The foam at this point has residual water phase (containing dissolved emulsifiers, electrolyte, initiator residues, and initiator) about 38–42 times (38–42x) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6x) the weight of the polymerized material. At this point, the sheets are then resaturated with a 1.5% $CaCl_2$ solution at 60° C., are squeezed in a series of 3 porous nip rolls equipped with vacuum to a water phase content of about 4x. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

Test Methods

General Conditions and Synthetic Urine

Unless otherwise noted, all tests are carried out at about 22+/−2° C. and at 35+/−15% relative humidity. The synthetic urine used in the test methods is commonly known as Jayco SynUrine and is available from Jayco Pharmaceuticals Company of Camp Hill, Pa. The formula for the synthetic urine is: 2.0 g/l of KCl; 2.0 g/l of $Na_2SO^4$; 0.85 g/l of $(NH_4)H_2PO4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Vertical Wicking Flux Test

The purpose of the Vertical Wicking Flux (VWF) test is to characterize the ability of an absorbent material (distribution material or acquisition/distribution material) to wick liquid vertically. Any material that has enough dry and wet integrity to be hung vertically can be tested. If a material has not sufficient integrity, an additional mechanical support layer can be added on either one or both surfaces of the material, such as low basis weight scrim or net, which does not or only negligibly impact on any fluid handling property.

In essence, this test is run by hanging 20 cm of a strip of the sample (in total at least 27.5 cm long) vertically in a reservoir of the test liquid, whereby the remaining 7.5 cm of the sample is placed horizontally on a plastic surface. Electrical conductivity sensors, are used to determine the time it takes to reach specific heights. Uptake vs. time data is obtained from the loss in weight of the liquid in the reservoir. At the end of the experiment, the sample is cut into sections to determine the longitudinal saturation profile. Thereby, the VWF test gives the following information:

Uptake (expressed in grams, or grams per cross-sectional area of the sample, or grams per weight of sample) vs. time Height of liquid front vs. time Flux through the sample (cumulative or incremental) vs. time Saturation profile along the length of the strip at the end of the experiment The following equipment is utilized to execute the test (refer to FIG. 3):

Motorized slide stand 950 (such as supplied by Concord-Renn Co., Cincinnati, Ohio, US) adjusted to obtain proper height of 20 cm from fluid reservoir 960 to horizontal laydown of sample 910. The motorized slide 950 ensures that the sample 910 is in contact with the liquid all the time by using a zero point sensor that maintains the apparatus at a position that is relative to the fluid level 962 in the reservoir 960. The slide stand 950 is further equipped with conductivity sensitive moisture detection rollers 930. A total of 9 rollers 930 are spaced individually at 2, 3.5, 5, 7.5, 10, 12.5, 15, 17.5, and 20 cm height above the level of the reservoir 962 (with the center of the rolls defining this measure). Two further sensors 930 are positioned in the horizontal part of the slide, so as to contact the sample 910 a running length of 22.5 cm and 27.5 cm from the liquid level. Although the exact width of the rollers 930 is insignificant, about ½" width has been found suitable, as well as a diameter of ⅜" (about 9.5 mm). It must be ensured, that the center of the roller 930 coincides with those heights. The rollers at 2, 5, 10, 15, and 20 cm are mounted to an arm 940 in a ladder-like fashion, and the rollers at 3.5, 7.5, 12.5, and 17.5 cm are mounted on another arm 940 in the same ladder-like fashion. During the testing, these two arms 940 are positioned on the opposite surfaces of the testing material 910, thus also allowing testing of materials of different calipers. During testing, the arms 940 are arrange parallel, angled about 5° to the vertical The circular reservoir 960 can be glass bowl of high enough capacity that the fluid level does not drop significantly during the testing such as Pyrex #3140 bowl of dimensions 150 mm diameter by 75 mm height. The reservoir 960 is covered to reduce evaporation by a lid having a slit of about (1"×2" or about 2.5 by 5 cm). The reservoir 960 is placed on a balance 965, such as Mettler PR 1203, Sartorius LC 1200S.

In order to ensure the required constant temperature and relative humidity conditions of 88° F. (31.1° C.) and 85% RH—unless otherwise desired and defined, the total measurement equipment can be placed inside as Environmental chamber—such as Electro-Tech Systems, Model 518.

A personal computer system 980 is used to record—as a function of time—the weight change of the scale 965, the signal of the rollers 930 when these are reached by the liquid front and the height of the motorized slide stand 950. Whilst various programs can be used to achieve this, a suitable program has been developed by Signalysis, Inc., 431 Ohio Pike, Cincinnati, Ohio, US (see below for more details).

In order to determine the weight of the sample sections, a pair of scissors, a ruler, and an analytical balance such as Mettler PG503 are required.

The synthetic urine used herein is the same as describe in the above.

Experimental Procedure

The test sample 910 is pre-conditioned overnight under standard conditions (72° F./22.2° C. and 50% RH), and the environmental chamber to is set to 88° F./31.1° C. and 85% RH and equilibrated for approximately 45 min.

A 5.0 cm×27.5 cm sample piece 910 is cut such as by a cutting die of those dimensions, and eleven 2.5 cm segments are marked by placing fine dots on the edges of the sample. The sample 910 is then pre-weighed, and its caliper is measured at about 0.09 psi (620 Pa) pressure by means of a standard caliper gauge.

The sample 910 is placed in between the rollers 930 such that the bottom of the sample is about 1 mm below the zero point on the VWF apparatus, without dipping in the liquid reservoir at this point. The top end of the sample 910 is fixed to the plastic plate such as by using a conventional adhesive tape 970.

The environmental chamber is closed, and equilibrated to the set temperature and RH, again for approximately 20 minutes.

The computerized unit 980 is initialized by input of the pertinent data into the program, e.g. sample name, desired test duration, sample length, width, caliper, temperature, RH). The test is started by immersing the sample via lowering the motorized slide into the test liquid and i) uptake vs. time and ii) times to reach specified heights are recorded continuously. The screen can display an uptake vs. time plot, while the experiment is in progress. At the end of the experiment, the sample 910 is automatically raised from the reservoir 960, and the saturation profile is determined, whilst ensuring that the sample is in the same vertical position that it was in during the experiment. This is necessary to ensure that there is no redistribution of liquid inside the sample while being cut into sections. The sample is removed from the test stand held vertically while 2.5 cm strips are cut and placed in pre-weighed dishes. The strips have to be cut from the bottom up.

Then, the horizontal portion of the sample is also cut into 2.5 cm sections, each placed in pre-weighed plastic dishes. Then, the wet weight of the sections is immediately determined to minimize evaporation losses. Then, the sections are dried in the oven at 150° F. overnight and re-weighed to determine the dry weights.

Calculations

Uptake

The uptake can be in the following units

Q: gm

Q*: gm/cm2 of initial dry cross-sectional area

Q': gm/gm of initial total sample weight

Qc': evaporation corrected uptake in gm/cm2

The evaporation loss from a partially covered reservoir (88° F./31.1° C. and 85% RH) has to be monitored (e.g. about 0.009 g/min).

In addition to this, the evaporation loss of liquid from the wetted part of the sample has to be considered for long lasting experiments (e.g. more than about two hours).

The "Evaporation corrected Uptake" (in g/min) can be calculated by subtracting the cumulative evaporation loss (i.e. the reservoir evaporation (in g/min) multiplied with the time (in min)) from the weight of the fluid in the reservoir (in g), and dividing it by the sample width and caliper (both in cm).

When data is taken at n distinct times for I=1, ..., n the following quantities are calculated:

Cumulative Flux, Fi (g/cm²/min)

$$F_i = Q_i^* / t_i$$

where $Q_j^*$ is the uptake (g/cm²)
and $t_i$ is the time (min)

Incremental Flux, $\Delta F_i$ (g/cm²/min)

$$\Delta F_i = (Q_i^* - Q_{i-1}^*)/(t_i - t_{i-1})$$

Saturation Profile Along the Length of the Sample

Liquid loading in each section (g/g)=$(W_{wet} - W_{dry})/W_{dry}$ where $W_{wet}$=weight of the wet section (g)
and $W_{dry}$=weight of the dry section The following describes the Computer Programming Information in more detail: The Wicking Flux program is used to acquire fluid uptake rate data versus time for experiments run to quantify the absorbent characteristics of diaper materials. The program works by reading serial data from a balance equipped with an RS-232 output. The internal clock of the PC is used to track time. The program is written for an IBM PC or compatible with DOS 3.0 (or late.) system.

Whenever an actual experiment is run, the data from the experiment (uptake values and time) and the values for all the input fields (except the sampling table) is written to a file in the current DOS directory This file can be opened by Excel on an IBM station for further data analysis and presentation.

A typical test protocol is described below:

Input fields
Material description
Material identification
Sample #1

| Operator: | Fluid Type: Jayco synthetic urine | Test Duration: |
|---|---|---|
| Width: 5.0000 cm | | 60 minutes |
| Temperature: | Length: 27.5 cm | Weight: 1.9000 g |
| 88.0000° F. | Relative Humidity: 85.0000% | |

| Output Time (min) | Weight (g) | Uptake (g/sq-cm) | Uptake (g/g) | Height (cm) |
|---|---|---|---|---|
| 0 | 0.424011 | 0.77093 | 0.223164 | 2 |
| 0.04485 | 0.924011 | 1.68002 | 0.486322 | 3.5 |
| 0.0778167 | 1.22 | 2.21818 | 0.642106 | 5 |
| 0.247167 | 2.017 | 3.66727 | 1.06158 | 7.5 |
| 0.552 | 2.86401 | 5.2073 | 1.50738 | 10 |
| 1.12688 | 3.79501 | 6.90002 | 1.99738 | 12.5 |
| 1.87295 | 4.5 | 8.18182 | 2.36842 | 15 |
| 3.32845 | 5.409 | 9.83454 | 2.84684 | 17.5 |
| 5.53095 | 6.25302 | 11.3691 | 3.29106 | 20 |

Reporting

At least 2 measurements should be made on each sample, recording the various out-put parameter as a function of time. Of course, the individual parameter can be correlated to each other, and also plotted accordingly.

For the purpose of describing materials suitable for being used within the present description, the cumulative flux at 15 cm height has been found to be particularly useful.

Saline Flow Conductivity (SFC)

This test determines the Saline Flow Conductivity (SFC) of the absorbent material, which either can be a pure material (such as a superabsorbent or hydrogel forming polymer material) or a mixture (such as of such hydrogel forming polymer material with a fibrous material such as airfelt). The material or member is swollen in Jayco synthetic urine under a confining pressure. The objective of this test is to assess the ability of absorbent member to acquire and distribute body fluids when being exposed to usage mechanical pressures. Darcy's law and steady-state flow methods are used for determining saline flow conductivity. (See, for example, "Absorbency," ed. by P. K. Chatterjee, Elsevier, 1985, Pages 42–43 and "Chemical Engineering Vol. II, Third Edition, J. M. Coulson and J. F. Richardson, Pergamon Press, 1978, Pages 125–127.)

The member is preswollen in Jayco synthetic urine for a time period of 60 minutes and then its flow conductivity measured under a mechanical confining pressure of 0.3 psi (about 2 kPa). Flow conductivity is measured using a 0.118 M NaCl solution. For members comprising a hydrogel-forming absorbent polymer whose uptake of Jayco synthetic urine versus time has substantially leveled off, this concentration of NaCl has been found to maintain the swelling of the hydrogel layer substantially constant during the measurement. For some absorbent members comprising hydrogel-forming absorbent polymers, small changes in thickness can occur as a result of polymer swelling, polymer deswelling, and/or changes in hydrogel-layer porosity. A constant hydrostatic pressure of 4920 dyne/cm2 (5 cm of 0.118M NaCl) is used for the measurement.

Flow rate is determined by measuring the quantity of solution flowing through ail the absorbent member as a function of time. Flow rate can vary over the duration of the measurement. Reasons for flow-rate variation include changes in the thickness of the absorbent member such as can occur in the presence of hydrogel layer, creation of flow channels, and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure. For systems where the flow rate is substantially constant, a absorbent member permeability coefficient can be calculated from the saline flow conductivity and the viscosity of ythe NaCl solution.

A suitable apparatus 610 for this test is shown in FIG. 4A. This apparatus includes a constant hydrostatic head reservoir indicated generally as 612 that sits on a laboratory jack indicated generally as 614. Reservoir 612 has lid 616 with a stoppered vent indicated by 618 so that additional fluid can be added to reservoir 612. An open-ended tube 620 is inserted through lid 616 to allow air to enter reservoir 612 for the purpose of delivering fluid at a constant hydrostatic pressure. The bottom end of tube 620 is positioned so as to maintain fluid in cylinder 634 at a height of 5.0 cm above the bottom of hydrogel layer 668 (see FIG. 4B).

Reservoir 612 is provided with a generally L-shaped delivery tube 622 having an inlet 622 a that is below the surface of the fluid in the reservoir. The delivery of fluid by tube 622 is controlled by stopcock 626. Tube 622 delivers fluid from reservoir 612 to a piston/cylinder assembly generally indicated as 628. Beneath assembly 628 is a support screen (not shown) and a collection reservoir 630 that sits on a laboratory balance 632.

Referring to FIG. 4A, assembly 628 basically consists of a cylinder 634, a piston generally indicated as 636 and a cover 637 provided with holes for piston 636 and delivery tube 622. As shown in FIG. 4A, the outlet 622b of tube 622 is positioned below the bottom end of tube 620 and thus will also be below the surface of the fluid (not shown) in cylinder 634. As shown in FIG. 4A, piston 636 consists of a generally cylindrical LEXANshaft 638 having a concentric cylindrical hole 640 bored down the longitudinal axis of the shaft. Both ends of shaft 638 are machined to provide ends 642 and 646. A weight indicated as 648 rests on end 642 and has a cylindrical hole 648a bored through the center thereof.

Inserted on the other end 646 is a generally circular Teflon piston head 650 having an annular recess 652 in the bottom thereof. Piston head 650 is sized so as to slidably move inside cylinder 634. As particularly shown in FIG. 4C, piston head 650 is provided with four concentric rings of twenty-four cylindrical holes each indicated generally as 654, 656, 658, and 660. As can be seen in FIG. 4C, concentric rings 654 to 660 fit within the area defined by recess 652. The holes in each of these concentric rings are bored from the top to bottom of piston head 650. The holes in each ring are spaced by approximately 15 degrees and offset by approximately 7.5 degrees from the holes in adjacent rings. The holes in each ring have a progressively smaller diameter going inwardly from ring 654 (0.204 inch (0.518 cm) diameter) to ring 660 (0.111 inch (0.282 cm) diameter). Piston head 650 also has cylindrical hole 662 bored in the center thereof to receive end 646 of shaft 638.

As shown in FIG. 4B, a fritted circular glass disc 664 fits within recess 652. Attached to bottom end of cylinder 634 is a No. 400 mesh stainless steel cloth screen 666 that is biaxially stretched to tautness prior to attachment. The sample of hydrogel-forming absorbent polymer indicated as 668 is supported on screen 666.

Cylinder 634 is bored from a transparent LEXANrod or equivalent and has an inner diameter of 6.00 cm (area=28.27 cm2), a wall thickness of approximately 0.5 cm, and a height of approximately 6.0 cm. Piston head 650 is machined from a solid Teflon rod. It has a height of 0.625 inches (1.588 cm) and a diameter that is slightly less than the inner diameter of cylinder 634, so that it fits within the cylinder with minimum wall clearances, but still slides freely. Recess 652 is approximately 56 mm in diameter by 4 mm deep. Hole 662 in the center of the piston head 650 has a threaded 0.625 inch (1.588 cm) opening (18 threads/inch) for end 646 of shaft 638. Fritted disc 664 is chosen for high permeability (e.g., Chemglass Cat No. CG-201-40, 60 mm diameter; X-Coarse Porosity) and is ground so that it fits snugly within recess 652 of piston head 650, with the bottom of the disc being flush with the bottom of the piston head. Shaft 638 is machined from a LEXANrod and has an outer diameter of 0.875 inches (2.177 cm) and an inner diameter of 0.250 inches (0.635 cm). End 646 is approximately 0.5 inches (1.27 cm) long and is threaded to match hole 662 in piston head 650. End 642 is approximately an inch long and 0.623 inches (1.582 cm) in diameter, forming an annular shoulder to support the stainless steel weight 648. Fluid passing through the hole 640 in shaft 638 can directly access the frilted disc 664. The annular stainless steel weight 648 has an inner diameter of 0.625 inches (1.588 cm), so that it slips onto end 642 of shaft 638 and rests on the annular shoulder formed therein. The combined weight of fritted glass disc 664, piston 636 and weight 648 equals 596 g, which corresponds to a pressure of 0.3 psi (2.1 KPa) for an area of 28.27 cm2. Cover 637 is machined from LEXANor its equivalent and is dimensioned to cover the top of cylinder 634. It has an 0.877 inch (2.228 cm) opening in the center thereof for shaft 638 of piston 636 and a second opening near the edge thereof for delivery tube 622.

The cylinder 634 rests on a 16 mesh rigid stainless steel support screen (not shown) or equivalent. This support screen is sufficiently permeable so as to not impede fluid flow into the collection reservoir 630. The support screen is generally used to support cylinder 634 when the flow rate of saline solution through assembly 628 is greater than about 0.02 g/sec. For flow rates less than about 0.02 g/sec, it is preferable that there be a continuous fluid path between cylinder 634 and the collection reservoir. This can be accomplished by replacing the support screen, collection reservoir 630, and analytical balance 632 with analytical balance 716, reservoir 712, fritted funnel 718, and the respective connecting tubes and valves of apparatus 710, and positioning cylinder 634 on the frilted disc in fritted funnel 718.

The synthetic urine used in this method is the same as define in the general part.

The 0.118 M NaCl solution is prepared by dissolving 6.896 g NaCl (Baker Analyzed Reagent or equivalent) to 1.0 liters with distilled water.

An analytical balance 632 accurate to 0.01 g (e.g., Mettler PM4000 or equivalent) is typically used to measure the quantity of fluid flowing through the hydrogel layer 668 when the flow rate is about 0.02 g/sec or greater. A more accurate balance (e.g., Mettler AE200 or equivalent) can be needed for less permeable hydrogel layers having lower flow rates. The balance is preferably interfaced to a computer for monitoring fluid quantity versus time.

The thickness of the absorbent member 668 in cylinder 634 is measured to an accuracy of about 0.1 mm. Any method having the requisite accuracy can be used, as long as the weights are not removed and the absorbent member is not additionally compressed or disturbed during the measurement. Using a caliper gauge (e.g., Manostat 15-100-500 or equivalent) to measure the vertical distance between the bottom of the stainless steel weight 648 and the top of cover 637, relative to this distance with no absorbent member 668 in cylinder 634 is acceptable. Also acceptable is the use of a depth gauge (e.g., Ono Sokki EG-225 or equivalent) to measure the position of piston 636 or stainless steel weight 648 relative to any fixed surface, compared to its position with no absorbent member in cylinder 634.

The SFC measurement is performed at ambient temperature (i.e., 20°–25° C.) and is carried out as follows:

The test sample can be obtained by punching out a 6.0 cm diameter circular-shaped structure from an absorbent member. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component of an absorbent article, the test sample is prepared by combining all the materials that constitute the member such that the combination is representative of the member in question. The test sample is a 5.4 cm diameter circle and is obtained by cutting with an arch punch.

If the test is run with a particulate material, such as superabsorbent granules, 0.9 gm aliquot thereof (corresponding to a basis weight of 0.032 gm/cm2) is added to cylinder 634 and distributed evenly on screen 666. For most absorbent members, moisture content is typically less than 5%. For these, the quantity of absorbent members to be added can be determined on a wet-weight (as is) basis. For absorbent members having a moisture content greater than about 5%, the added weight should be corrected for moisture. Care is taken to prevent absorbent members from adhering to the cylinder walls. Piston 636 (minus weight 648) with disc 664 positioned in recess 652 of piston head 650 is inserted into cylinder 634 and positioned on top of the dry absorbent member 668. If necessary, piston 636 can be turned gently to more-uniformly distribute the absorbent member on screen 666. Cylinder 634 is then covered with cover 637 and weight 648 is then positioned on end 642 of shaft 638.

If the test sample has sufficient integrity to be treated as a web, it can be prepared by punching out a 6 cm diameter circular-shaped structure, such as by an arc punch. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component of an absorbent article, the test sample is prepared by combining all the materials that constitute the member such that the combination is representative of the member in question. The sample is the preweighed to determine its dry weight and added to cylinder 634. The above procedure will then be applied accordingly.

A fritted disc (coarse or extra coarse) having a diameter greater than that of cylinder 634 is positioned in a wide/shallow flat-bottomed container that is filled to the top of the fritted disc with Jayco synthetic urine. The piston/cylinder assembly 628 is then positioned on top of this fritted glass disc. Fluid from the container passes through the fritted disc and is absorbed by absorbent member 668. After a time period of 60 minutes, the thickness of the absorbent members is determined. Care is taken that the absorbent members does not lose fluid or take in air during this procedure.

The piston/cylinder assembly 628 is then transferred to apparatus 610. The support screen (not shown) and any gap between it and the piston/cylinder assembly 628 is presaturated with saline solution. If the fritted funnel 718 of the PUP apparatus 710 is used to support cylinder 634, the surface of the fritted funnel should be minimally elevated relative to the height of the fluid in the collection reservoir, with valves between the fritted funnel and the collection reservoir being in the open position. (The fritted funnel elevation should be sufficient such that fluid passing through the hydrogel layer does not accumulate in the funnel.)

The SFC measurement is initiated by adding NaCl solution through hole 640 in shaft 638 in order to expel air from piston head 650 and then turning stopcock 626 to an open position so that delivery tube 622 delivers fluid to cylinder 634 to a height of 5.0 cm above the bottom of absorbent member 668. Although the measurement is considered to have been initiated (to) at the time NaCl solution is first added, the time at which a stable hydrostatic pressure, corresponding to 5.0 cm of saline solution, and a stable flow rate is attained (ts) is noted. (The time ts should typically be about one minute or less.) The quantity of fluid passing through absorbent member 668 versus time is determined gravimetrically for a time period of 10 minutes. After the elapsed time, piston/cylinder assembly 628 is removed and the thickness of absorbent member 668 is measured. Generally the change in thickness of the absorbent member is less than about 10%.

In general, flow rate need not be constant. The time-dependent flow rate through the system, Fs(t) is determined, in units of g/sec, by dividing the incremental weight of fluid passing through the system (in grams) by incremental time (in seconds). Only data collected for times between ts and ts+10 minutes is used for flow rate calculations. Flow rate results between ts and ts+10 minutes is used to calculate a value for Fs(t=0), the initial flow rate through the absorbent member. Fs(t=0) is calculated by extrapolating the results of a least-squares fit of Fs(t) versus time to t=ts.

For a layer having a very high permeability (e.g., a flow rate greater than ~2 g/sec), it may not be practical to collect fluid for the full 10 minute time period. For flow rates greater than ~2 g/sec, the time of collection can be shortened in proportion to the flow rate.

For some absorbent members comprising hydrogel-forming absorbent polymers having extremely low permeability, absorption of fluid by the hydrogel competes with transport of fluid through the absorbent member and either there is no flow of fluid through the absorbent member and into the reservoir or, possibly, there is a net absorption of fluid out of the PUP reservoir. For these extremely low permeability absorbent member, it is optional to extend the time for Jayco SynUrine absorption to longer periods (e.g., 16 hours).

In a separate measurement, the flow rate through apparatus 610 and the piston/cylinder assembly 628 (Fa) is measured as described above, except that no absorbent member is present. If Fa is much greater than the flow rate through the system when the absorbent member is present, Fs, then no correction for the flow resistance of the SFC apparatus and the piston/cylinder assembly is necessary. In this limit, Fg=Fs, where Fg is the contribution of the absorbent member to the flow rate of the system. However if this requirement is not satisfied, then the following correction is used to calculate the value of Fg from the values of Fs and Fa:

$$Fg=(Fa \times Fs)/(Fa-Fs)$$

The Saline Flow Conductivity (K) of the absorbent member is calculated using the following equation:

$$K=\{Fg(t=0) \times L0\}/\{\rho \times A \Delta P\},$$

where Fg(t=0) is the flow rate in g/sec determined from regression analysis of the flow rate results and any correction due to assembly/apparatus flow resistance, L0 is the initial thickness of the absorbent member in cm, $\rho$ is the density of the NaCl solution in gm/cm3. A is the area of the absorbent member in cm2, $\Delta P$ is the hydrostatic pressure in dyne/cm2, and the saline flow conductivity, K, is in units of cm3 sec/gm.

The average of three determinations should be reported.

For absorbent member where the flow rate is substantially constant, a permeability coefficient (k) can be calculated from the saline flow conductivity using the following equation:

$$k = \mu \cdot K,$$

where $\mu$ is the viscosity of the NaCl solution in g/s/cm and the permeability coefficient, k is in units of cm2.

The following is an example of how SFC is calculated for a pure hydrogel forming polymer layer:

The measured value of Fa is 412 g/min=6.87 g/sec. For a single determination on the particulate hydrogel-forming polymer sample 3–5 (Example 3), the extrapolated value for Fs(t=0) is 33.9 g/min=0.565 g/sec, with a very-low ratio of slope:intercept of 9×10−5 sec−1. Correcting for apparatus resistance:

$$Fg=(6.87\times0.565), (6.87-0.565)=0.616 \text{ g/sec}$$

Given a 0.118 M saline density of 1.003 g/cm3 (CRC Handbook of Chemistry and Physics, 61st Edition) a hydrogel-layer thickness of 1.134 cm, a hydrogel layer area of 28.27 cm2, and a hydrostatic pressure of 4920 dyne/cm2.

$$K=(0.616\times1.134)/(1.003\times28.27\times4920)\times10-6 \text{ cm3 sec/gm}=5.0\times10-6 \text{ cm3 sec/gm}$$

Considering the substantially constant flow rate and given a 0.118 M saline viscosity of 0.01015 poise (CRC Handbook of Chemistry and Physics, 61st Edition):

$$=K=(5.0\times10-6)\times0.01015\times10-6 \text{ cm2}=5.1\times10-8 \text{ cm2}$$

Liquid Permeability Test

Simplified Liquid Permeability Test

This Simplified Permeability Test provides a measure for permeability for two special conditions: Either the permeability can be measured for a wide range of porous materials (such as non-wovens made of synthetic fibers, or cellulosic structures) at 100% saturation, or for materials, which reach different degrees of saturation with a proportional change in caliper without being filled with air (respectively the outside vapor phase), such as the collapsible polymeric foams, for which the permeability at varying degrees of saturation can readily be measured at various thickness.

In particular for polymeric foam materials, it has been found useful to operate the test at an elevated temperature of 31° C., so as to better simulate in-use conditions for absorbent articles.

In principle, this tests is based on Darcy's law, according to which the volumetric flow rate of a liquid through any porous medium is proportional to the pressure gradient, with the proportionality constant related to permeability.

$$Q/A=(k\eta/)*(\Delta P/L)$$

where:

Q=Volumetric Flow Rate [cm$^3$/s];
A=Cross Sectional Area [cm$^2$];
k=Permeability (cm$^2$) (with 1 Darcy corresponding to $9.869*10^{-13}$ m$^2$);
η=Viscosity (Poise) [Pa*s];
ΔP/L=Pressure Gradient [Pa/m];
L=caliper of sample [cm].

Hence, permeability can be calculated—for a fixed or given sample cross-sectional area and test liquid viscosity—by measurement of pressure drop and the volumetric flow rate through the sample:

$$k=(Q/A)*(L/\Delta P)*\eta$$

The test can be executed in two modifications, the first referring to the transplanar permeability (i.e. the direction of flow is essentially along the thickness dimension of the material), the second being the in-plane permeability (i.e. the direction of flow being in the x-y-direction of the material).

Figure 5:
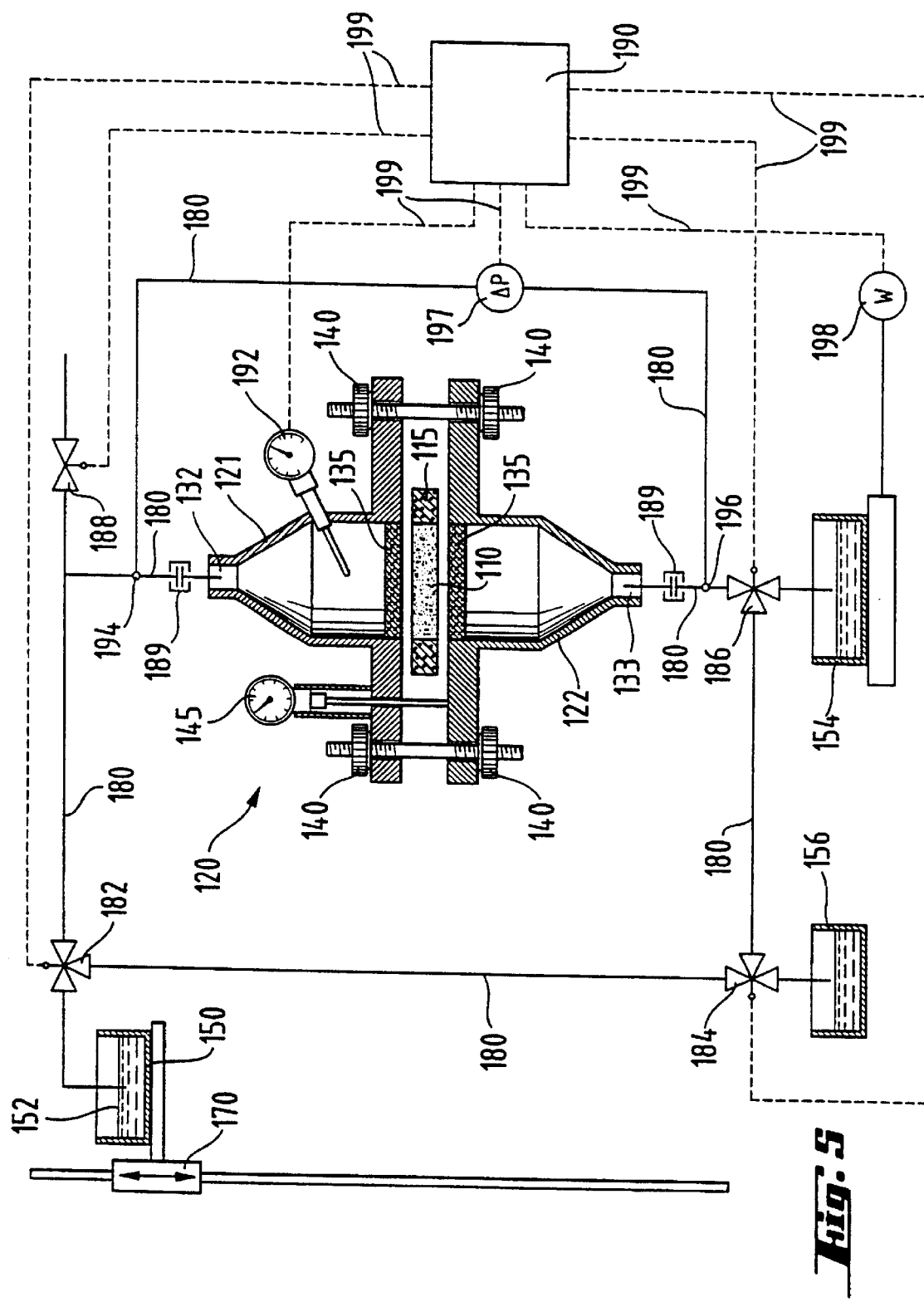
FIG. 5—Simplified Transplanar Permeability Test stand

The test set-up for the simplified, transplanar permeability test can be seen in FIG. 5 which is a schematic diagram of the overall equipment and—as an insert diagram—a partly exploded cross-sectional, not to scale view of the sample cell. The test set-up comprises a generally circular or cylindrical sample cell 120, having an upper 121 and lower 122 part. The distance of these parts can be measured and hence adjusted by means of each three circumferentially arranged caliper gauges 145 and adjustment screws 140. Further, the equipment comprises several fluid reservoirs 150, 154, 156 including a height adjustment 170 for the inlet reservoir 150 as well as tubings 180, quick release fittings 189 for connecting the sample cell with the rest of the equipment, further valves 182, 184, 186, 188. The differential pressure transducer 197 is connected via tubing 180 to the upper pressure detection point 194 and to the lower pressure detection point 196. A Computer device 190 for control of valves is further connected via connections 199 to differential pressure transducer 197, temperature probe 192, and weight scale load cell 198.

The circular sample 110 having a diameter of 1 in (about 2.54 cm) is placed in between two porous screens 135 inside the sample cell 120, which is made of two 1 in (2.54 cm) inner diameter cylindrical pieces 121, 122 attached via the inlet connection 132 to the inlet reservoir 150 and via the outlet connection 133 to the outlet reservoir 154 by flexible tubing 180, such as tygon tubing. Closed cell foam gaskets 115 provide leakage protection around the sides of the sample. The test sample 110 is compressed to the caliper corresponding to the desired wet compression, which is set to 0.2 psi (about 1.4 kPa) unless otherwise mentioned. Liquid is allowed to flow through the sample 110 to achieve steady state flow. Once steady state flow through the sample 110 has been established, volumetric flow rate and pressure drop are recorded as a function of time using a load cell 198 and the differential pressure transducer 197. The experiment can be performed at any pressure head up to 80 cm water (about 7.8 kPa), which can be adjusted by the height adjusting device 170. From these measurements, the flow rate at different pressures for the sample can be determined.

The equipment is commercially available as a Permeameter such as supplied by Porous Materials, Inc, Ithaca, N.Y., US under the designation PMI Liquid Permeameter, such as further described in respective user manual of 2/97. This equipment includes two Stainless Steel Frits as porous screens 135, also specified in said brochure. The equipment consists of the sample cell 120, inlet reservoir 150, outlet reservoir 154, and waste reservoir 156 and respective filling and emptying valves and connections, an electronic scale, and a computerized monitoring and valve control unit 190.

The gasket material 115 is a Closed Cell Neoprene Sponge SNC-1 (Soft), such as supplied by Netherland Rubber Company, Cincinnati, Ohio., US. A set of materials with varying thickness in steps of 1/16" (about 0.159 cm) should be available to cover the range from 1/16"–½" (about 0.159 cm to about 1.27 cm) thickness.

Further a pressurized air supply is required, of at least 60 psi (414 KPa), to operate the respective valves.

Test fluid is deionized water. The test is then executed by the following steps:
1) Preparation of the Test Sample(s):

In a preparatory test, it is determined, if one or more layers of the test sample are required, wherein the test as outlined below is run at the lowest and highest pressure. The number of layers is then adjusted so as to maintain the flow rate during the test between 0.5 cm$^3$/second at the lowest pressure drop and 15 cm$^3$/second at the highest pressure drop. The flow rate for the sample should be less than the flow rate for the blank at the same pressure drop. If the sample flow rate exceeds that of the blank for a given pressure drop, more layers should be added to decrease the flow rate.

Sample size: Samples are cut to 1" (about 2.54 cm) diameter, by using an arch punch, such as supplied by McMaster-Carr Supply Company, Cleveland, Ohio., US. If samples have too little internal strength or integrity to maintain their structure during the required manipulation, a conventional low basis weight support means can be added, such as a PET scrim or net.

Thus, at least two samples (made of the required number of layers each, if necessary) are precut. Then, one of these is saturated in deionized water at the temperature the experiment is to be performed (70° F., 31° C.) unless otherwise noted).

The caliper of the wet sample is measured (if necessary after a stabilization time of 30 seconds) under the desired compression pressure for which the experiment will be run by using a conventional caliper gauge (such as supplied by AMES, Waltham, Mass., US) having a pressure foot diameter of 1⅛" (about 2.86 cm), exerting a pressure of 0.2 psi (about 1.4 kPa) on the sample (110), unless otherwise desired.

An appropriate combination of gasket materials is chosen, such that the total thickness of the gasketing foam 115 is between 150 and 200% of the thickness of the wet sample (note that a combination of varying thickness of gasket material may be needed to achieve the overall desired thickness). The gasket material 115 is cut to a circular size of 3 in (about 7.5 cm diameter), and a 1 inch (2.54 cm) hole is cut into the center by using the arch punch.

In case, that the sample dimensions change upon wetting, the sample should be cut such that the required diameter is taken in the wet stage. This can also be assessed in this preparatory test, with monitoring of the respective dimensions. If these change such that either a gap is formed, or the sample forms wrinkles which would prevent it from smoothly contacting the porous screens or frits, the cut diameter should be adjusted accordingly.

The test sample 110 is placed inside the hole in the gasket foam 115, and the composite is placed on top of the bottom half of the sample cell, ensuring that the sample is in flat, smooth contact with the screen 135, and no gaps are formed at the sides.

The top of the test cell 121 is laid flat on the lab bench (or another horizontal plane) and all three caliper gauges 145 mounted thereon are zeroed.

The top of the test cell 121 is then placed onto the bottom part 122 such that the gasket material 115 with the test sample 110 lays in between the two parts. The top and bottom part are then tightened by the fixation screws 140, such that the three caliper gauges are adjusted to the same value as measured for the wet sample under the respective pressure in the above.

2) To prepare the experiment, the program on the computerized unit 190 is started and sample identification, respective pressure etc. are entered.

3) The test will be run on one sample 110 for several pressure cycles, with the first pressure being the lowest pressure. The results of the individual pressure runs are put on different result files by the computerized unit 190. Data are taken from each of these files for the calculations as described below. (A different sample should be used for any subsequent runs of the material.)

4) The inlet liquid reservoir 150 is set to the required height and the test is started on the computerized unit 190.

5) Then, the sample cell 120 is positioned into the permeameter unit with Quick Disconnect fittings 189.

6) The sample cell 120 is filled by opening the vent valve 188 and the bottom fill valves 184, 186. During this step, care must be taken to remove air bubbles from the system, which can be achieved by turning the sample cell vertically, forcing air bubbles—if present—to exit the permeameter through the drain.

Once the sample cell is filled up to the tygon tubing attached to the top of the chamber 121, air bubbles are removed from this tubing into the waste reservoir 156.

7) After having carefully removed air bubbles, the bottom fill valves 184, 186 are closed, and the top fill 182 valve is opened, so as to fill the upper part, also carefully removing all air bubbles.

8) The fluid reservoir is filled with test fluid to the fill line 152.

Then the flow is started through the sample by initiating the computerized unit 190.

After the temperature in the sample chamber has reached the required value, the experiment is ready to begin.

Upon starting the experiment via the computerized unit 190, the liquid outlet flow is automatically diverted from the waste reservoir 156 to the outlet reservoir 154, and pressure drop, and temperature are monitored as a function of time for several minutes.

Once the program has ended, the computerized unit provides the recorded data (in numeric and/or graphical form).

If desired, the same test sample can be used to measure the permeability at varying pressure heads, with thereby increasing the pressure from run to run. The equipment should be cleaned every two weeks, and calibrated at least once per week, especially the frits, the load cell, the thermocouple and the pressure transducer, thereby following the instructions of the equipment supplier.

The differential pressure is recorded via the differential pressure transducer connected to the pressure probes measurement points 194, 196 in the top and bottom part of the sample cell. Since there may be other flow resistances within the chamber adding to the pressure that is recorded, each experiment must be corrected by a blank run. A blank run should be done at 10, 20, 30, 40, 50, 60, 70, 80 cm requested pressure, each day. The permeameter will output a Mean Test Pressure for each experiment and also an average flow rate.

For each pressure that the sample has been tested at, the flow rate is recorded as Blank Corrected Pressure by the computerized unit 190, which is further correcting the Mean Test Pressure (Actual Pressure) at each height recorded pressure differentials to result in the Corrected Pressure. This Corrected Pressure is the DP that should be used in the permeability equation below.

Permeability can then be calculated at each requested pressure and all permeabilities should be averaged to determine the k for the material being tested.

Three measurements should be taken for each sample at each head and the results averaged and the standard deviation calculated. However, the same sample should be used, permeability measured at each head, and then a new sample should be used to do the second and third replicates.

Figure 6A:
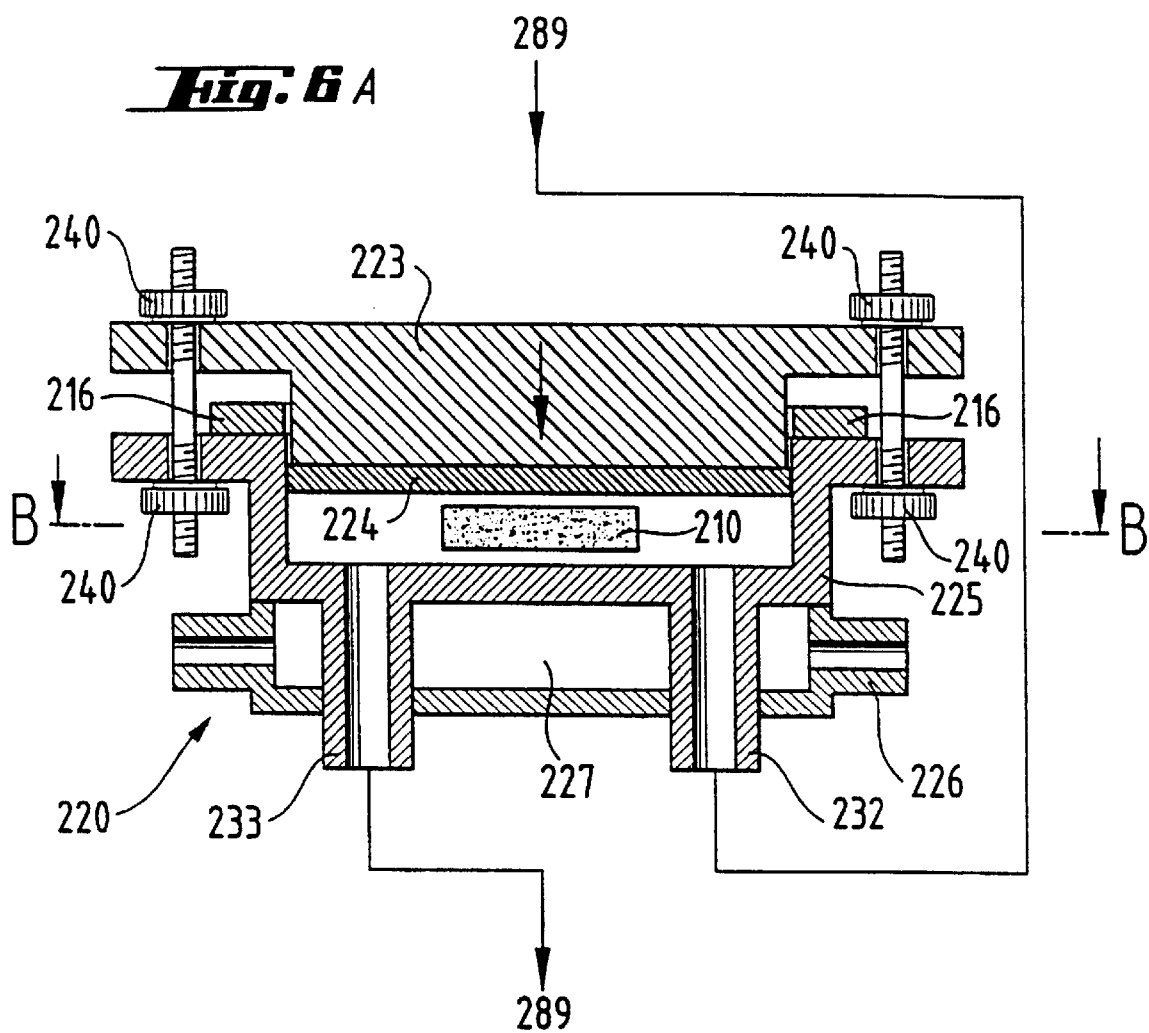
FIG. 6A—Simplified In-plane Permeability Test stand sample cell
Figure 6B:
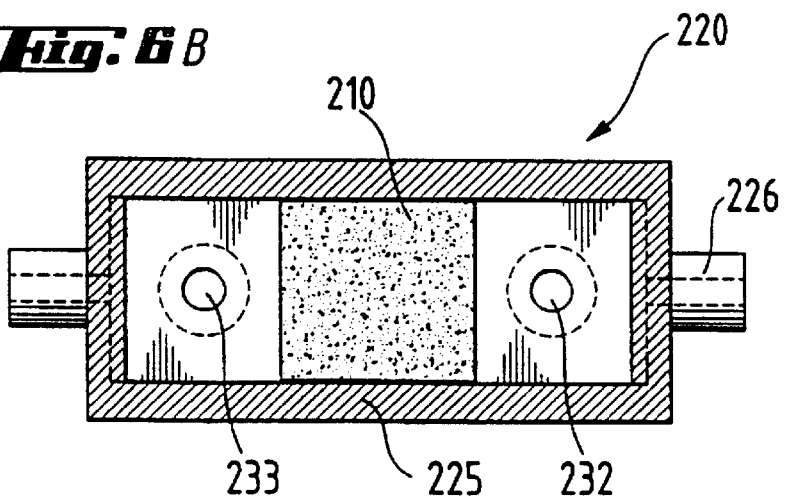
FIG. 6B—Cross-sectional view of FIG. 6A along line B—B

The measuring of the in-plane permeability under the same conditions as the above described transplanar permeability, can be achieved by modifying the above equipment such as schematically depicted in FIGS. 6A and 6B showing the partly exploded, not to scale view of the sample cell only. Equivalent elements are denoted equivalently, such that the sample cell of FIG. 6 is denoted 210, correlating to the numeral 110 of FIG. 5, and so on. Thus, the transplanar simplified sample cell 120 of FIG. 5 is replaced by the in-plane simplified sample cell 220, which is designed so that liquid can flow only in one direction (either machine direction or cross direction depending on how the sample is placed in the cell). Care should be taken to minimize channeling of liquid along the walls (wall effects), since this can erroneously give high permeability reading. The test procedure is then executed quite analogous to the transplanar simplified test.

The sample cell 220 is designed to be positioned into the equipment essentially as described for the sample cell 120 in the above transplanar test, except that the filling tube is directed to the inlet connection 232 the bottom of the cell 220. FIG. 6A shows a partly exploded view of the sample cell, and FIG. 6B a cross-sectional view through the sample level.

The test cell 220 is made up of two pieces: a bottom piece 225 which is like a rectangular box with flanges, and a top piece 223 that fits inside the bottom piece 225 and has flanges as well. The test sample is cut to the size of 2"in×2" in (about 5.1 cm by 5.1 cm) and is placed into the bottom piece. The top piece 223 of the sample chamber is then placed into the bottom piece 225 and sits on the test sample 210. An incompressible neoprene rubber seal 224 is attached to the upper piece 223 to provide tight sealing. The test liquid flows from the inlet reservoir to the sample space via Tygon tubing and the inlet connection 232 further through the outlet connection 233 to the outlet reservoir. As in this test execution the temperature control of the fluid passing through the sample cell can be insufficient due to lower flow rates, the sample is kept at the desired test temperature by the heating device 226, whereby thermostated water is pumped through the heating chamber 227. The gap in the test cell is set at the caliper corresponding to the desired wet compression, normally 0.2 psi(about 1.4 kPa). Shims 216 ranging in size from 0.1 mm to 20.0 mm are used to set the correct caliper, optionally using combinations of several shims.

At the start of the experiment, the test cell 220 is rotated 90° (sample is vertical) and the test liquid allowed to enter slowly from the bottom. This is necessary to ensure that all the air is driven out from the sample and the inletloutlet connections 232/233. Next, the test cell 220 is rotated back to its original position so as to make the sample 210 horizontal. The subsequent procedure is the same as that described earlier for transplanar permeability, i.e. the inlet reservoir is placed at the desired height, the flow is allowed to equilibrate, and flow rate and pressure drop are measured. Permeability is calculated using Darcy's law. This procedure is repeated for higher pressures as well.

For samples that have very low permeability, it may be necessary to increase the driving pressure, such as by extending the height or by applying additional air pressure on the reservoir in order to get a measurable flow rate. In plane permeability can be measured independently in the machine and cross directions, depending on how the sample is placed in the test cell.

General Liquid Permeability Test

Figure 7:
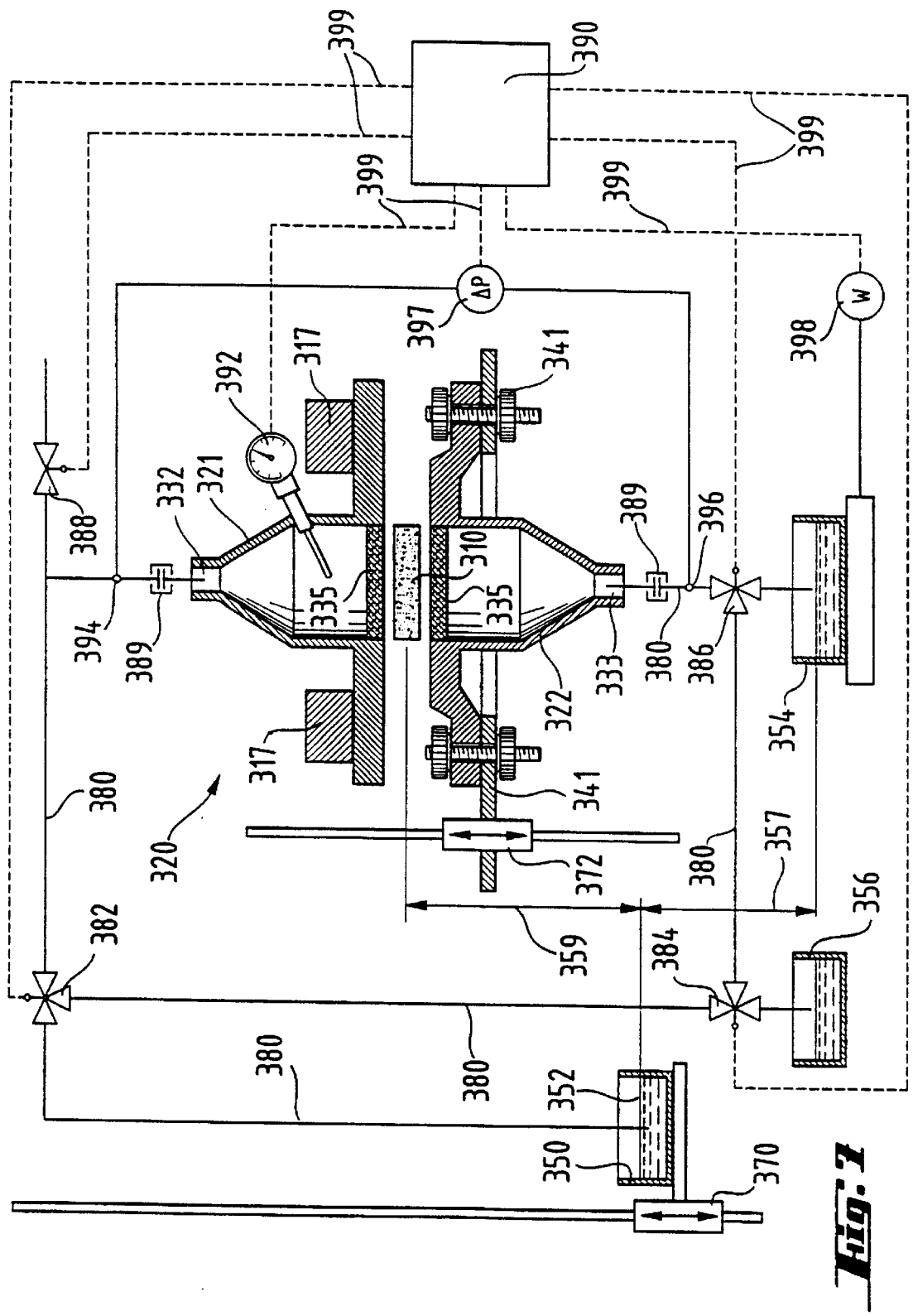
FIG. 7—General Transplanar Permeability Test stand
Figure 8A:
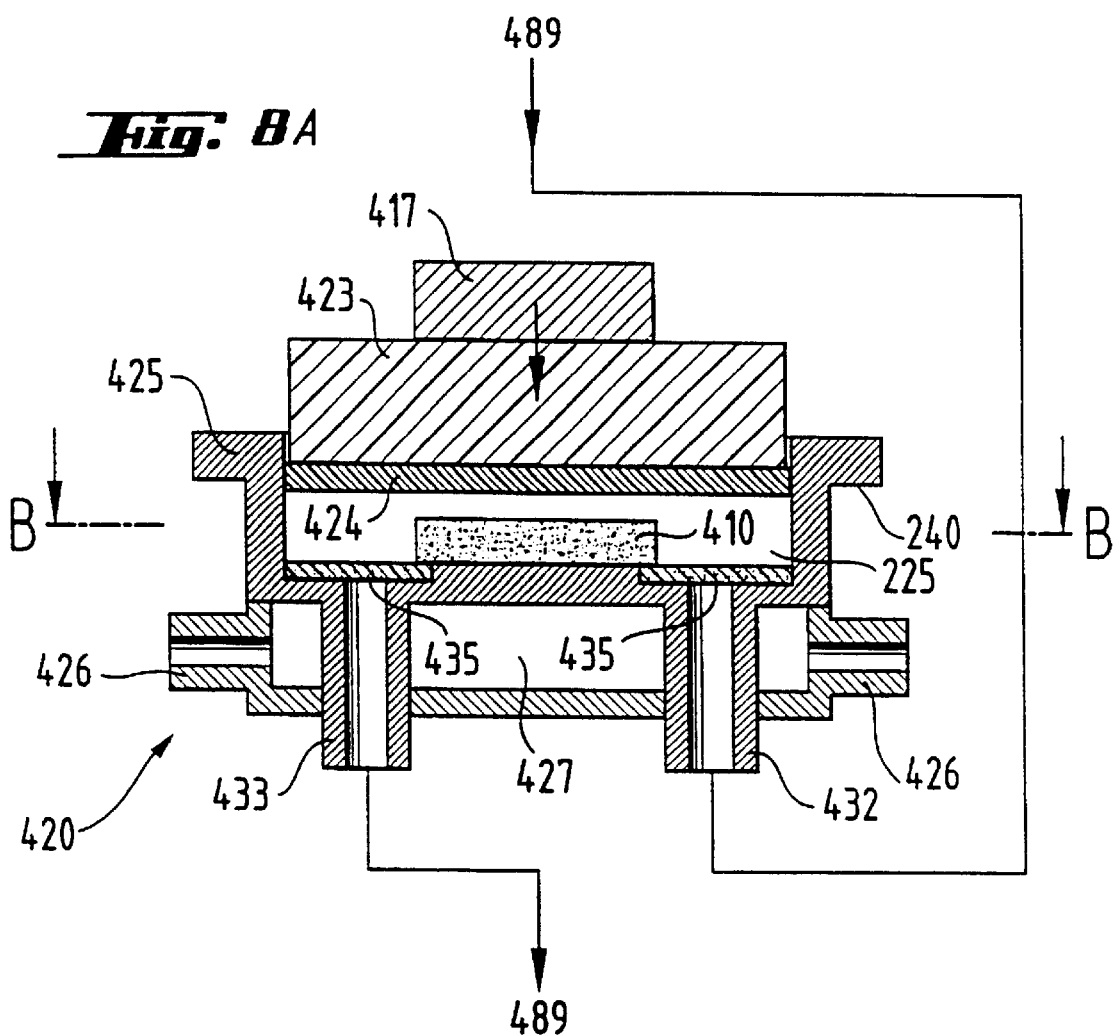
FIG. 8A—General In-plane Permeability Test stand sample cell
Figure 8B:
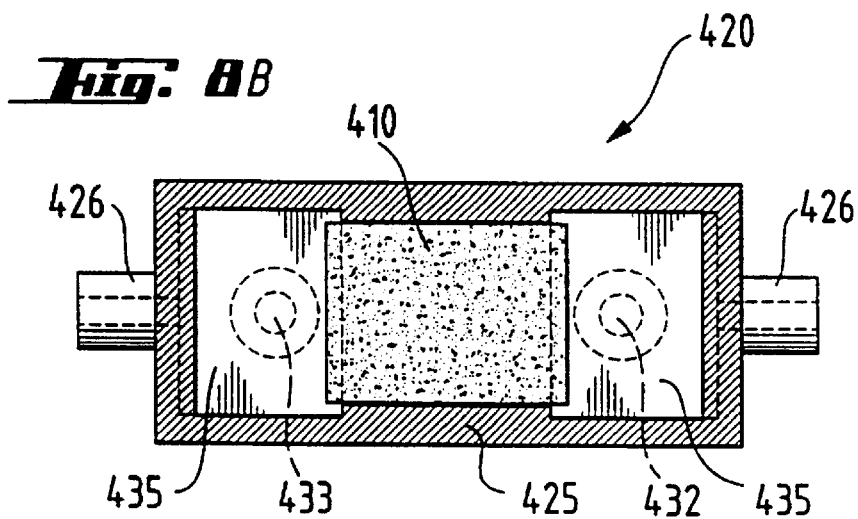
FIG. 8B—Cross-sectional view of FIG. 8A along line B—B

The generalized permeability test can measure permeability as a function of saturation for any porous material. The principle of the tests is similar to the one for the Simplified Test, with the essential difference being that the sample is loaded with a defined amount of air in addition to the liquid loading, resulting in a fixed degree of saturation. This is achieved by the test arrangement as schematically depicted in FIG. 7 showing the principles as well as the specifics for the General Transplanar Permeability, and in FIG. 8, showing the differences for the General In-plane Permeability. Unreferenced numerals correspond to the respective numerals of FIG. 5 (e.g., waste reservoir 356 corresponds to waste reservoir 156 etc.).

Therein, also the sample cell 320/420 is mounted with fixation (341, not shown FIG. 8) on a height adjustment device 372, in addition to the inlet reservoir 350 being height adjustable by a means 370. This inlet reservoir defines a first height difference 357 relative to the outlet reservoir 354, which relates to the differential pressure $\Delta p$ (which denotes the pressure differential for calculating the permeability). This inlet reservoir 350 defines a second height difference 359 relative to the sample height which relates to the differential pressure $\Delta p(c)$, which denotes the pressure differential linked to the saturation in the sample, whereby higher capillary suction typically correlates to lower saturation.

The experiment is started at low $\Delta PC$ (close to zero cm of water) at which the sample will be at 100% saturation. Liquid flows through the sample due to the applied pressure drop $\Delta p(c)$ (inlet reservoir height—outlet reservoir height). At steady state, the uptake of liquid in the outlet reservoir is measured as a function of time. Permeability can be calculated from the pressure drop and the volumetric flow rate data using Darcy's law. The exact degree of saturation can be obtained from the weight of the wet sample after the test compared to the dry sample before the test.

In order to measure the permeability at saturation below 100%, a new test sample is first brought to 100% saturation as described in the paragraph above. Next, the sample is moved to a higher height (10 cm for example) and is allowed to equilibrate at that height. During this time, liquid continuously flows from the inlet to the outlet reservoir. The saturation in the sample will decrease with time. When steady state is reached, i.e. when the uptake versus time plot is linear, the flow rate, pressure drop and saturation are measured as described above. This procedure is repeated for several sample heights using new samples.

It may be necessary to increase the pressure drop between the inlet and outlet reservoirs as the saturation decreases in order to get a measurable flow rate. This is because, for most porous materials, permeability decreases steeply with decreasing saturation. It is necessary to ensure that the pressure drop between the inlet and outlet reservoirs is much smaller than the capillary suction.

It is necessary to use wide liquid reservoirs 352, 354 in order to ensure that the liquid level does not change significantly while waiting for steady state to be reached.

This test gives permeability versus saturation for the desorption cycle, that is the sample has higher saturation to start with. Whilst of course permeability data can be generated for the absorption cycle, these should not be used in present evaluations, as some hysteresis effects might occur.

The sample cell 320 for the general transplanar permeability test differs from sample cell 120 of the simplified transplanar permeability test essentially in that it comprises two frits 335 arranged on top and underneath the sample 310. For the frits 335 it is necessary to ensure that most of the resistance to flow is offered by the sample and the frit resistance is negligible. A fine pored, thin membrane over a coarse frit allows measurements up to high heights without offering significant resistance to flow. The frits should be selected so as to have a sufficiently high bubble point pressure corresponding to more than about 200 cm water height, but at the same time providing low flow resistance. This can well be achieved by selecting sufficiently thin membranes of the require bubble point pressure overlying a more open support structure.

For the general permeability tests, care must be taken, that the air is allowed to contact the sample via the side surfaces, so as to allow varying degrees of saturation depending on the $\Delta p(c)$. Thus, the sample cell design is essentially identical to the test cell of the simplified transplanar test, except, that the foam gasketing material is removed, and the arrangement to adjust the gap between the top and the bottom parts replaced by a constant pressure generating device, such as a weight 317 to maintain (together with the weight of the top piece 321) the sample under the desired pressure, of 0.2 psi (about 1.4 kPa) unless otherwise desired.

For the general in-plane permeability test the sample cell 420 is shown in FIG. 8, which is a design being derived from the simplified in-plane test and the principles as described in the above. Thus, the fluid in entering the sample cell 420 via the fluid inlet 432 and outlet 433, which are connected to the membranes 435, such as frits of the type as described above (for frits 335). The test sample 410 is positioned with its ends overlaying the two frits, but not with the center part of 2 in by 2 in (about 5.1 cm by 5.1 cm) whereby wrinkles and gaps between the sample and the membranes have to be avoided. The test sample 410 is placed between the upper and lower part of the sample cell 420, with the weight 417 being used to adjust the pressure under which the experiment is run (0.2 psi (about 1.4 kPa) unless otherwise desired and denoted). Also, the sample is kept a constant temperature via the heating device 426, e.g. by pumping constant temperature water through the heating chamber 427.

Also for this set up, the possibility of air entering into the sample via the side surfaces is essential to allow the varying degrees of saturation.

Liquid Viscosity

The liquid viscosity is an important input parameter for the above determination, and should be taken for the respective fluid for the respective temperature, either from well known tables, or equations, or measured via well established measurement procedures.

Surface Tension Test method

The surface tension measurement is well known to the man skilled in the art, such as with a Tensiometer K10T from Krüss GmbH, Hamburg, Germany using the DuNouy ring method as described in the equipment instructions. After cleaning the glassware with iso-propanol and de-ionized water, it is dried at 105° C. The Platinum ring is heated over a Bunsen-burner until red heat. A first reference measurement is taken to check the accuracy of the tensiometer as well as the originally high surface tension of the test liquid.

The test solution is prepared by adding 3 g of test material to 100 ml of test liquid in an appropriately sized beaker so as to fully saturate the test material in an excess of test liquid. After about 1 minute, the material is squeezed and released by means of tweezers while being submerged in the test liquid to enhance the wash out, and after another minute this is repeated again. The test material is removed from the beaker by means of the tweezers, with absorbed liquid carefully being squeezed back into the beaker. The liquid in the filtered through a suitable filter paper (such as filter paper #597 from Schleicher & Schüll, Germany, and the surface tension of the filtrate is determined.

Design Capacities and Teabag Test

Teabag Centrifuge Capacity Test (TCC test)

Whilst the TCC test has been developed specifically for superabsorbent materials, it can readily be applied to other absorbent materials.

The Teabag Centrifuge Capacity test measures the Teabay Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately.

After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilized at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

$$TCC=[(\text{sample teabag weight after centrifuging})-(\text{blank teabag weight after centrifuging})-(\text{dry absorbent material weight})] \div (\text{dry absorbent material weight}).$$

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. EDepending on the size of the unit area (preferably 2 cm by 2 cm) the defines how much averaging is taking place naturally, the smaller the size, the less averaging will occur.

Ultimate Storage Capacity

In order to determine or evaluate the Ultimate Design Storage Capacity of an. absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers (SAP) can be used for such SAP materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

Compression Under Load Determination

An important mechanical feature of the absorbent polymeric foams useful in the present invention, whether collapsible or non-collapsible, is their strength in their expanded state, as determined by its resistance to compression deflection (RTCD). The RTCD exhibited by the foams is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams useful herein can be quantified by determining the amount of strain produced in a sample of saturated foam held under a certain confining pressure for a specified temperature and period of time. The method for carrying out this particular type of test is described in the TEST METHODS section of PCT publication WO 96/21680. Foams useful as absorbents are those which exhibit a RTCD such that a confining pressure of 5.1 kPa (0.74 psi) produces a strain of preferably less than 75% typically about 50% or less compression of the foam structure when it has been saturated to its free absorbent capacity with synthetic urine having a surface tension of 65±5 dynes/cm. Preferably the strain produced under such conditions will be in the range from about 2 to about 25%, more preferably from about 2 to about 15%, most preferably from about 2 to about 10%.

Vertical Hang Sorption Height (VHSH)

The Vertical Hang Sorption Height ("VHSH") test is effected by selecting a strip of foam of suitable length (typically at least 60 cm) with a width of typically about 1 cm. The strip is hung in a chamber thermostatted to 31° C. using clips to suspend the strip. The bottom of the strip is immersed in the test fluid, also at 31° C. The test fluid is preferably synthetic urine as described in U.S. Pat. No. 5,599,335 (Goldman et al.) issued Feb. 4, 1997, the disclosure of which is incorporated by reference herein. Over time, the test fluid will wick up the strip and reach an equilibrium point where no further wicking occurs. The test fluid may be dyed to facilitate determination of the equilibrium point. Care must be taken to prevent evaporation from the sample, e.g. by encasing it within a glass tube wherein the glass does not touch the sample, and keeping the sample tube suitably capped. The time required to reach equilibrium may vary for the materials of this invention, and range from about 24 to 96 hrs, or more. When no perceptible change in the height of the wicking fluid is observed over a 1 hour period, equilibrium is assumed to have been achieved.

The test strip is removed from the test chamber with care to avoid expressing the fluid held therein. The strip is cut into 2.5 cm sections in length and each section is weighed. For convenience, the initial sections below about 50% of the fully expanded height may be cut into sections that are 2 inches (5.1 cm) in length. These weights are divided by the oven dry weight of the foam to compute the capacity (g/g) at the various heights of the foam. A graph such as is depicted in FIG. 5 can be developed by charting the capacities vs. the heights at which the sections were taken. The VHSH height at X % is the height in cm where X% of the 0 cm capacity (or FAC) is retained in the foam. A typical value of importance is the VHSH at 90%. In principle, X may be any value. The most reproducible measure for VHSH is achieved at X=90% within the experience of the inventors. It will be obvious to one skilled in the art that this single point value does not fully express the shape of the curve obtained in a plot of capacity vs. height. The single point however serves as a practical point of comparison for the foams of the present invention.

Free Swell Rate Method

This method determines the speed of superabsorbent materials, especially polymeric hydrogelling materials, such as cross-linked poly-acrylates to swell in synthetic urine of the Jayco type,as detailed in the General Section for test methods. The measurement principle is to allow superabsorbent material to absorb a known amount of fluid, and the time take to absorb the fluid is measured. The result is then expressed in gram of absorbed fluid per gram of material per second.

Test samples can be tested at their "as is" moisture, however, it is preferred to have these equilibrated under laboratory conditions for two days in a dessicator, using drierite (calcium sulfate or silica gel) or equivalent.

About 1 g (+/−0.1 g) of the test specimen are weighed to an accuracy of +/−0.0001 g into a 25 ml beaker, which has 32 to 34 mm diameter, and 50 mm height. The material is evenly spread over the bottom. 20 ml of synthetic urine are weighed to an accuracy of +/−0.01 g in a 50 ml beaker, and are then poured carefully but quickly into the beaker containing the test material. A timer is started immediately upon the liquid contacting the material. The beaker is not moved, or agitated during swelling.

The timer is stopped, and the time recorded to the nearest second (or more accurately if appropriate), when the last part of undisturbed fluid is reached by the swelling particles. In order to increase the reproducibility of the determination of the end point, the liquid surface can be illuminated by a small lamp without heating the surface by that lamp. The beaker is re-weighed to monitor the actually picked up liquid.

The result is calculated by dividing the amount of actually picked up liquid by the time required for this pick up, and is expressed in "g/g/sec". The method should be repeated as required to ensure reproducibility.

If the test material has an increased moisture content, this can be incorporated into the result by dividing the grams of fluid by grams of dry absorbent material per second, or it can be considered by carefully drying the material under mild conditions like vacuum, and then measuring according to the above procedure. In all cases, results should be reported accordingly, in the absence of any specification, the test is run with an undried material of less than 10% moisture content, and reported "as is".

Moisture Vapor Transmission Rate (MVTR)

Briefly summarizing this method, a known amount of desiccant ($CaCl_2$) is put into a flanged "cup" like container. The sample material is placed on the top of the container and held securely by a retaining ring and gasket. The assembly is then weighed and recorded as the initial weight. The assembly is placed in a constant temperature (40° C.) and humidity (75% RH) (CT/CH) chamber for five (5) hours. The assembly is then removed from the chamber, sealed to prevent further moisture intake, and allowed to equilibrate for at least 30 minutes at the temperature of the room where the balance is located. The amount of moisture absorbed by the $CaCl_2$ is determined gravimetrically and used to estimate the moisture vapor transmission rate (MVTR) of the sample by weighing the assembly and recording the final weight. The moisture vapor transmission rate (MVTR) is calculated and expressed in $g/m^2/24$ hr. using the formula below. A reference sample, of established permeability, is used as a positive control for each batch of samples. Samples are assayed in triplicate. The reported MVTR is the average of the triplicate analyses, rounded to the nearest 100. The significance of differences in MVTR values found for different samples can be estimated based on the standard deviation of the triplicate assays for each sample.

Suitable Analytical Balances for performing the measurements include a Mettler AE240 or equivalent (300 g capacity) or a Sartorius 2254S0002 or equivalent (1000 g capacity). A suitable sample holding assembly comprises a cup and retaining ring machined from Delrino (such as that available from McMaster-Carr Catalog #8572K34) with a gasket made of GC Septum Material (Alltech catalog #6528). The dessicant comprises $CaCl_2$ for U-tubes, available from Wako Pure Chemical Industries, Ltd., Richmond, Va. Product #030-00525. The plastic food wrap comprises Saran Wrap, available from Dow Chemical Company, or equivalent.

The $CaCl_2$ can be used directly from a sealed bottle as long as the size of the lumps is such that they do not pass through a No. 10 sieve. Usually the top two-thirds of the bottle does not have to be sieved. However, the bottom third contains fines that should be removed by sieving. The $CaCl_2$ can be used from a closed container without drying. It can be dried at 200° C. for 4 hours if required.

Exxon Exxaire microporous material, Catalog #XBF-100W, is used as the Reference Standard Material. Triplicate samples should be prepared and analyzed along with each set of test samples as described below.

Representative samples should be obtained from the materials to be tested. Ideally, these samples should be taken from different areas of the material so as to represent any variations present. Three samples of each material are needed for this analysis.

Samples should be cut into rectangular pieces approximately 1.5"×2.5" (3.8 cm*6.35 cm). If the samples are not uniform, the area for which breathability is to be evaluated is marked and recorded, and so is the side that is to be exposed to high humidity. For samples used in diapers and catamenials, this is usually the side that contacts the skin.

To begin a test session, (1) 15.0±0.02 grams of $CaCl_2$ are weighed and placed in the MVTR cup. The $CaCl_2$ should be level and about 1 cm from the top of the cup, such as by light tapping in the bench top. Then (2) the sample is placed, with the high humidity side up (if required), over the opening in the top of the cup. It needs to be ensured, that the sample overlaps the opening so that a good seal will be obtained. Next, (3) the gasket material and the retaining ring are placed on the top of the cup, whilst keeping the screw holes aligned, and whilst checking that the sample has not moved. Further, the screws are tightened to securely fasten the retaining ring and to seal the sample to the top of the cup. Care should be taken to not overtighten the screws as this leads to distortion of some samples. If distortion of the sample occurs, the screws need to be loosened and tightened again. Then (4), the MVTR cup assembled in step 3, is weighed as the initial weight.

After weighing of the assembly, (5) the sample is placed in the CT/CH chamber for 5.0 hours (to the nearest minute). When the time has elapsed, (6) the sample is removed from the CT/CH chamber, and tightly covered with plastic wrap secured by a rubber band. The time of sample removal is recorded to within the nearest minute. After allowing the samples to equilibrate for at least 30 minutes at the temperature of the room where the balance is located, (7) the Saran wrap is removed, and the cup re-weighed to be recorded as the final weight.

The MVTR is then calculated in units of $g\ H_2O/24\ hr/m^2$ using the formula:

$$MVTR = \frac{(\text{final weight} - \text{initial weight}) \times 24.0}{\text{area of sample in meters} \times 5.0(\text{time in chamber})}$$

where: 24.0 is used to convert the data to the 24 hour basis;
the area of sample is equal to the open area of the mouth of the cup; and
5.0 is the duration of the test in hours The average MVTR is calculated for each set of triplicate samples and the reference standard, and is rounded 100. If the MVTR for the reference standard is in the range of 4000 to 4600, it is in the acceptable quality control range and the results for that day can be reported. The rounded value for the sample can then be reported. Steps 1 through 7 are repeated for the triplicate analyses of each sample and the reference standard. Typically, multiple samples are processed in parallel.

Figure 9:
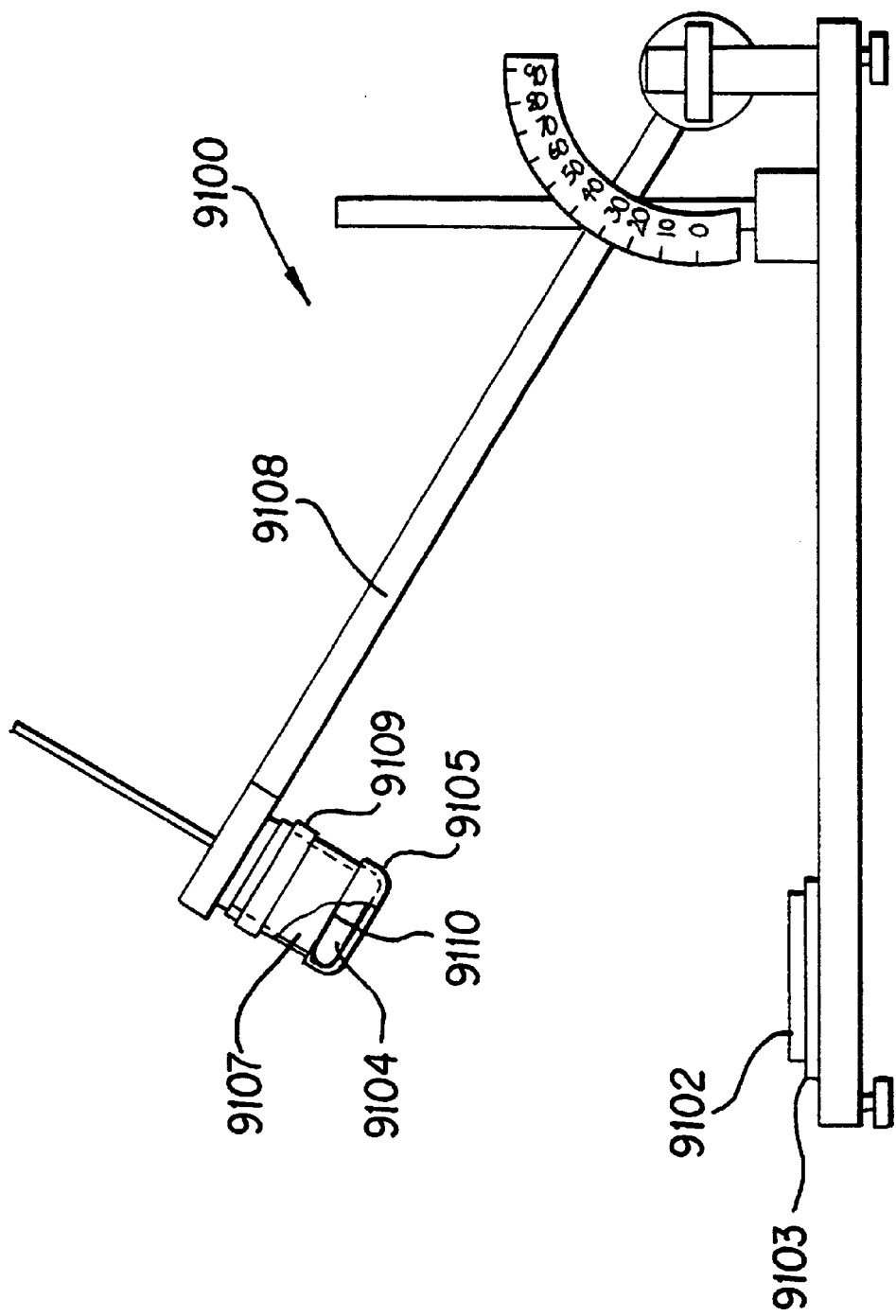
FIG. 9—Dynamic fluid Transmission Test stand

Dynamic Fluid Transmission is measured with the apparatus 9100 shown in FIG. 9. According to this test, an absorption material 9102 weighed to the nearest 0.0001 gram is placed directly on top of the energy absorbing impact pad 9103. The absorption material 9102 may comprise a No. 2 filter paper available from Whatman Laboratory Division, Distributed by VWR Scientific of Cleveland, Ohio. The absorption material should be able to absorb and retain simulated urine which passes through the sheet material being tested. The energy absorbing impact pad 9103 is a carbon black filled cross linked rubber foam. The 12.7 cm by 12.7 cm (5 inch by 5 inch) square impact pad has a density of 0.1132 g/cm$^3$ and a thickness of 0.79 cm (0.3125 inches). The impact pad 9103 has a Durometer Value of A/30/15 according to ASTM 2240-91. A circular absorbent core material 9104 measuring 0.0635 meters (2.5 inches) in diameter is weighed. The absorbent core material may comprise individualized, crosslinked wood pulp cellulosic fibers as described in U.S. Pat. No. 5,137,537 issued to Herron et al. on Aug. 11, 1992.

Other absorbent materials that can be used include airfelt, tissue, cellulose wadding, as long as these exhibit the required absorbent capacity of at least 10 g/g. if the materials have a capacity below 10 g/g then they should be wetted to at least 80% of their saturation capacity. Also, the absorbent materials should be essentially free of "superabsorbent materials" which might bind the liquid too tightly and thus affect the results.

The absorbent core material should be able to hold a sufficient amount of simulated urine, e.g., at least about ten times its dry weight. The absorbent core has a basis weight of about 228 g/m$^2$. The absorbent core material is then is loaded with simulated urine to about ten (10) times its dry weight. The simulated urine is an aqueous composition, maintained at 37° C., and comprised of the following components dissolved in distilled water: 2.0 g/L KCl; 2.0 g/L Na$_2$SO$_4$; 0.85 g/L (NH$_4$)H$_2$PO$_4$; 0.15 g/L (NH$_4$)$_2$H$_2$PO$_4$; 0.19 g/L CaCl$_2$; and 0.23 g/L MgCl$_2$. The test liquid exhibits a surface energy value of 60 mN/m A section of the backsheet material 9105 to be tested is placed face down with the outside surface on a clean and dry tabletop. The loaded core material 9104 is placed directly in the center of the backsheet material 9105. The backsheet/core arrangement is then secured to the impact portion 9107 of the impact arm 9108 with a rubber band 9109. The backsheet/core arrangement is positioned such that the core 9104 is adjacent the bottom surface 9110 of the impact portion 9107. The impact arm 9108 is raised to a desired impact angle to provide the desired impact energy. The impact arm 9108 is dropped and the impact arm 9108 is then allowed to rest on the sample for about 10 seconds after impact. The arm is then raised and the filter paper 9102 is removed and placed on a digital scale. The mass of the wet filter paper is then recorded at the three minute mark. The dynamic fluid transmission value (DFTV) is calculated and expressed in g/m$^2$ using the following formula:

$$DFTV = \frac{\text{(mass of the wet filter paper(grams)} - \text{mass of the dry filter paper(grams))}}{\text{impact area(m}^2\text{)}}$$

The impact area, expressed in m$^2$, is the area of the bottom surface 9110 of the impact portion 9107. The impact area is 0.00317 m$^2$. The absorbent core material 9104 should have an area slightly larger than that of the impact area of the surface 9110.

What is claimed is:

1. Absorbent Article, having a fluid receiving surface oriented towards the wearer during use, and a garment oriented surface opposite said fluid receiving surface, a crotch region and one or more waist regions, said crotch region having a crotch width, said article comprising an absorbent core having an ultimate fluid storage region, and a fluid distribution region positioned between said ultimate storage region and said garment oriented surface, and in fluid communication with said ultimate fluid storage region, characterized in that said distribution region comprises fluid distribution material having a Capillary Sorption Absorption Height at 30% of its maximum capacity (CSAH 30 of at least 25 cm, and in that said ultimate fluid storage region comprises ultimate fluid storage material which has a Capillary Sorption Desorption Capacity at 100 cm (CSDC 100); and which further has a Capillary Sorption Desorption Capacity at 0 cm (CSDC 0) higher than said CSDC 100, thereby having a Loosely Bound Liquid Capacity (LBLC) as the difference between (CSDC 0 and CSDC 100); and having a Capillary Sorption Desorption Release Height when 50% of said LBLC are released (CSDRH 50) which is less than said Capillary Sorption Absorption height at 30% of its maximum capacity (CSAH 30) of the distribution material.

2. An absorbent article according to claim 1, further comprising a backsheet oriented away from the wearer during use, wherein said backsheet exhibits a Moisture Vapor Transmission rate of at least 2,500 g/m2/day (according to the method as described herein), and said backsheet exhibiting a moisture impact value of less than about 35 g/m2 at an impact of 2,400 J/m2 and when tested with a liquid having a surface tension of 33+/−1 mN/m.

3. An absorbent article according to claim 2, wherein said backsheet comprises more than one regions differing in the MVTR values.

4. An absorbent article according to claim 3, wherein said backsheet comprises a layer of fibrous material.

5. Absorbent article according to claim 1, wherein said storage region has a SFC value of more than 25×10−7 cm$^3$ sec/g.

6. Absorbent article according to claim 1, wherein said storage region has an in-plane permeability value of at least 10 Darcy.

7. Absorbent article according to claim 1, wherein said fluid distribution material has a CSAH 30 of at least 40 cm.

8. Absorbent article according to claim 1, wherein in the crotch region said fluid distribution material has a permeability value at 50% saturation (k(50)), which is at least 15% of the permeability value at 100% saturation (k(100)).

9. Absorbent article according to claim 8, wherein said fluid distribution material has a permeability value at 50% saturation (k(50), which is at least 25% of the permeability value at 100% saturation (k(100)).

10. Absorbent article according to claim 8, wherein in the crotch region said fluid distribution material has a permeability value at 50% saturation (k(50), which is at least 35% of the permeability value at 100% saturation (k(100)).

11. Absorbent article according to claim 1, wherein said fluid distribution material has a permeability at 100% saturation (k100) of at least 1 Darcy.

12. Absorbent article according to claim 1, wherein said fluid distribution material has an expansion factor of at least 4.

13. Absorbent article according to claim 1, wherein said distribution material has a Cumulative Flux value at 15 cm in the Vertical Wicking test of at least 0.02 g/cm$^2$/min.

14. An absorbent article according to claim 1, wherein said distribution region comprises foam material.

15. An absorbent article according to claim 14, wherein said foam material is a polymeric foam material.

16. An absorbent article according to claim 15, wherein said polymeric foam material is derived from high internal phase water-in-oil emulsions.

17. An absorbent article according to claim 16, wherein said polymeric foam material has a compression under a load of 5.1 kPa (0.74 psi) of less than 75%.

18. An absorbent article according to claim 17, wherein said distribution region foam material has non-uniform properties along the lateral or longitudinal axis of the article.

19. An absorbent article according to claim 18, wherein said non-uniform properties are selected from the group consisting of pore size, hydrophilicity, resiliency (compression under load), CSDC, CSAC at corresponding heights.

20. An absorbent article according to claim 1, wherein the distribution region comprise fibrous material.

21. An absorbent article according to any of claim 20, wherein said distribution region comprises a material which has been mechanically treated after formation.

22. An absorbent article according to claim 1, wherein said distribution region comprises at least a single layer material.

23. An absorbent article according to claim 22, wherein said distribution region has at least one of the group consisting of an essentially homogeneous composition and an essentially homogeneous density.

24. An absorbent article according to claim 22, wherein said distribution region is of essentially uniform basis weight.

25. An absorbent article according to claim 22, wherein said distribution region is of non-uniform basis weight.

26. An absorbent article according to claim 1, wherein said storage region comprises fibrous or foam material.

27. An absorbent article according to claim 1, wherein said storage region comprises superabsorbent material.

28. An absorbent article according to claim 27, wherein said ultimate fluid storage region comprises from about 50% to about 100% by weight superabsorbent material.

29. An absorbent article according to claim 28, wherein said ultimate fluid storage region comprises from about 80% to about 100% by weight superabsorbent material.

30. An absorbent article according to claim 27, wherein said ultimate fluid storage region comprises bonding means for said superabsorbent material wherin said bonding means is selected form the group consisnting of melt-blown adhesive and chemical crosslinker type.

31. An absorbent article according to claim 27, wherein said storage region comprises superabsorbent material having a SFC of at least 50×10−7 $cm^3sec/g$.

32. An absorbent article according to claim 27, wherein said ultimate fluid storage region comprises superabsorbent material of the mixed-bed ion exchange type.

33. An absorbent article according to claim 1, wherein said storage region is essentially homogeneous in composition.

34. An absorbent article according to claim 1, wherein said storage region is a layered structure having at least one layer.

35. An absorbent article according to claim 1, wherein said storage region is essentially free of void, apertures, or gaps having an individual void, aperture or gap volume of more than 10 $mm^3$.

36. Absorbent article according to claim 1, whereby the crotch region has a lower ultimate fluid storage capability than one or more waist region(s) together.

37. An absorbent article according to claim 1, wherein said crotch region has a sectional ultimate fluid storage sectional capacity of less than 41% of the total core ultimate fluid storage capacity.

38. An absorbent article according to claim 37, wherein the crotch width of the absorbent core is not greater than 7.5 cm (3 inch).

39. An absorbent article according to claim 37, wherein the crotch width of the absorbent core is between 3.8 cm (1.5 inch) and 6.4 cm (2.5 inch).

40. An absorbent article according to claim 1, further' characterized in that the length of the crotch region is half of the length of the total absorbent core.

41. An absorbent article according to claim 1, further characterized in that it comprises a ultimate liquid storage material providing at least 60% of the total ultimate storage capacity of the absorbent core.

42. Absorbent article according to claim 1 wherein the average basis weight of the ultimate storage material is less than 450 $g/m^2$.

43. An absorbent article according to claim 1, wherein said ultimate fluid storage region comprises at least two subregions spatially apart from each other and in fluid connection via said fluid distribution region.

44. An absorbent article according to claim 43, wherein at least of said ultimate fluid storage regions is positioned longitudinally forward from the loading point of said article, and at least one of said sub-regions is positioned longitudinally rearward from said loading point.

45. An absorbent article according to claim 1, wherein at least on fluid distribution region and one ultimate fluid storage region form subregions of a fluid distribution/storage region.

46. An absorbent article according to claim 45, wherein said fluid distribution sub-region and said ultimate fluid storage sub-region are connected by a transition region.

47. An absorbent article according to claim 45, wherein said properties of the transition region are selected from the group consisting of pore size, porosity, hydrophilicity, compressibility.

48. An absorbent article according to claim 1, further comprising a backsheet oriented away from the wearer during use, wherein said backsheet is of the breathable type by having Moisture Vapor Transmission Rate of at least 200 $g/m^2/d$.

49. An absorbent article according to claim 48, wherein said backsheet comprises one or more materials selected from the group consisting of 1) microporous films or film laminates, 2) Nonwovens, including coated non-wovens and plasma treated non-wovens, 3) Monolithic films, 4) laminates, 5)formed films and combinations thereof.

50. An absorbent article according to claim 49, wherein said backsheet comprises a polymeric material having a water absorption of at least 5% per ASTM method D570.

51. An absorbent article according to any of claim 50, wherein said backsheet is in direct contact with said liquid distribution layer.

52. Absorbent article according to claim 1, wherein said storage region material has a CSDC 100 value of more than 10 g/g.

53. Absorbent article according to claim 1, wherein said ultimate fluid storage region material has a CSDRH 50 value of less than 40 cm.

54. Absorbent Article, having a fluid receiving surface oriented towards the wearer during use, and a garment oriented surface opposite said fluid receiving surface, said article comprising an ultimate fluid storage region, and a fluid distribution region positioned between said ultimate storage region and said garment oriented surface, and in fluid communication with said ultimate fluid storage region, characterized in that said ultimate fluid storage region comprises ultimate fluid storage material which has a Capillary Sorption Desorption Capacity at 100 cm (CSDC 100) of at least 10 g/g; which further has a Capillary Sorption Desorption Capacity at 0 cm (CSDC 0) higher than said CSDC 100, thereby having a Loosely Bound Liquid Capacity (LBLC) as the difference between (CSDC 0 and CSDC 100); and having a Capillary Sorption Desorption Release Height when 50% of said LBLC are released (CSDRH 50) of less than 60 cm; and said distribution region comprises fluid distribution material having a Capillary Sorption Absorption Height at 30% of its maximum capacity (CSAH 30) of at least 35 cm.

* * * * *

UNITED STATES PATENT AND TRADEMARK OFFICE
CERTIFICATE OF CORRECTION

PATENT NO. : 6,664,439 B1
DATED : December 16, 2003
INVENTOR(S) : Silke Arndt et al.

It is certified that error appears in the above-identified patent and that said Letters Patent is hereby corrected as shown below:

Title page,
Item [57], ABSTRACT,
Line 15, delete "Disuibution" and insert -- Distribution --.

Column 4,
Line 45, delete "200 g/m$^2$/24 hrs," and insert -- 200 g/m$^2$/24hrs, --.
Line 60, delete "flex" and insert -- Flex --.

Column 7,
Line 40, delete "and ,the" and insert -- and the --.

Column 27,
Line 61, delete "60 tm," and insert -- 60 $\mu$m, --.

Column 28,
Line 37, delete "foarm." and insert -- foam. --.

Column 29,
Line 17, delete "divinyinaphthalenes" and insert -- divinylnaphthalenes --.
Line 19, delete "divinyidiphenyl-methanes," and insert -- divinyldiphenyl-methanes, --.

Column 38,
Line 15, delete "pre-wefting" and insert -- pre-wetting --.

Column 40,
Line 6, delete "α-chiorosorbic acid," and insert -- α-chlorosorbic acid, --.

Column 41,
Line 6, delete "now abadoned;" and insert -- now abandoned; --.
Line 11, delete "now abadoned" and insert -- now abandoned --.

Column 42,
Line 51, delete "cross-linking" and insert -- crosslinking --.

Column 45,
Lines 28-29, delete "KITYHAWK®" and insert -- KITTYHAWK® --.
Line 62, delete "retaining;" and insert -- retaining --.

Column 46,
Line 1, delete "pdlypropylenelpolyester," and insert -- polypropylene/polyester, --.

UNITED STATES PATENT AND TRADEMARK OFFICE
CERTIFICATE OF CORRECTION

PATENT NO.    : 6,664,439 B1
DATED         : December 16, 2003
INVENTOR(S)   : Silke Arndt et al.

It is certified that error appears in the above-identified patent and that said Letters Patent is hereby corrected as shown below:

Column 48,
Line 49, delete "$g/m^2 124$ hr." and insert -- $g/m^2/24$ hr. --.
Lines 57 and 59, delete "$g/m^2/24$ h" and insert -- $g/m^2/24h$ --.
Line 67, delete "tretaed" and insert -- treated --.

Column 49,
Line 48, delete "a" and insert -- as --.

Column 50,
Line 7, delete "are" and insert -- area --.
Line 22, delete "4500 $g/m^2/24$ h to 6000 $g/m^2/24$ h" and insert
-- 4500 $g/m^2/24h$ to 6000 $g/m^2/24h$ --.
Line 62, delete "MVRR" and insert -- MVTR --.

Column 51,
Line 57, delete "PEBAX®)," and insert -- PEBAX®, --.
Line 64, delete "Hytrel (Film" and insert -- Hytrel® Film --.

Column 52,
Line 9, delete "MVTR in $g/m^2/24$ hr." and insert -- MVTR in $g/m^2/24$hr. --.

Column 53,
Line 56, delete "600" and insert -- 60° --.
Line 66, delete "1996now" and insert -- 1996 now --.

Column 55,
Line 28, delete "600" and insert -- 60° --.

Column 58,
Line 12, delete "(480 g)," and insert -- (640 g), --.

Column 61,
Lines 4-5, delete "0.85 g/1 of $(NH_4)H_2PO4$;" and insert -- 0.85 g/l of $(NH_4)H_2PO_4$; --.
Line 5, delete "ad" and insert -- and --.

Column 62,
Line 7, delete "as" and insert -- an --.
Lines 62 and 64, delete "gm/cm2" and insert -- $gm/cm^2$ --.

UNITED STATES PATENT AND TRADEMARK OFFICE
CERTIFICATE OF CORRECTION

PATENT NO.      : 6,664,439 B1
DATED           : December 16, 2003
INVENTOR(S)     : Silke Arndt et al.

It is certified that error appears in the above-identified patent and that said Letters Patent is hereby corrected as shown below:

<u>Column 63,</u>
Lines 33-34, delete "DOS 3.0 (or late.) system." and insert -- DOS 3.0 (or later.) system. --.

<u>Column 64,</u>
Line 40, delete "through ail the" and insert -- through the --.
Line 56, delete "ythe" and insert -- the --.

<u>Column 65,</u>
Line 2, delete "622 a" and insert -- 622$\alpha$ --.
Lines 45-46, delete "(area=28.27 cm2)," and insert -- (area=28.27 cm$^2$), --.

<u>Column 66,</u>
Line 1, delete "frifted" and insert -- fritted --.
Lines 6-7, delete "28.27 cm2." and insert -- 28.27 cm$^2$. --.
Line 25, delete "frilted" and insert -- fritted --.

<u>Column 68,</u>
Line 61, delete "gm/cm3." and insert -- gm/cm$^3$. --.
Line 62, delete "cm2," and insert -- cm$^2$, --.
Line 63, delete "dyne/cm2," and insert -- dyne/cm$^2$, --.
Line 64, delete "cm3 sec/gm." and insert -- cm$^3$ sec/gm. --.

<u>Column 69,</u>
Line 7, delete "cm2." and insert -- cm$^2$. --.
Line 18, delete "1.003 g/cm3" and insert -- 1.003 g/cm$^3$ --.
Line 21, delete "28.27 cm2," and insert -- 28.27 cm$^2$, --.
Line 21, delete "4920 dyne/cm2." and insert -- 4920 dyne/cm$^2$. --.
Lines 23 and 24, delete "10-6 cm3 sec/gm" and insert -- 10-6 cm$^3$ sec/gm --.
Line 29, delete "10-6 cm2=5.1x10-8 cm2" and insert -- 10-6 cm$^2$=5.1x10-8 cm$^2$ --.
Line 54, delete "$Q/A=(k\eta/)*(\Delta P/L)$" and insert -- $Q/A=(k/\eta)*(\Delta P/L)$ --.

<u>Column 73,</u>
Line 52, delete "inletloutlet" and insert -- inlet/outlet --.

<u>Column 76,</u>
Line 17, delete "Teabay" and insert -- Teabag --.

<u>Column 77,</u>
Line 4, delete "EDepending" and insert -- Depending --.
Line 12, delete "an." and insert -- an --.

UNITED STATES PATENT AND TRADEMARK OFFICE
CERTIFICATE OF CORRECTION

PATENT NO. : 6,664,439 B1
DATED : December 16, 2003
INVENTOR(S) : Silke Arndt et al.

It is certified that error appears in the above-identified patent and that said Letters Patent is hereby corrected as shown below:

Column 79,
Line 60, delete "Delrino" and insert -- Delrin® --.

Column 81,
Line 37, delete "KCl;" and insert -- KCl; --.

Column 82,
Line 29, delete "2,500 g/m2/day" and insert -- 2,500 g/m$^2$/day --.
Line 32, delete "35 g/m2" and insert -- 35 g/m$^2$ --.
Line 32, delete "2,400 J/m2" and insert -- 2,400 J/m$^2$ --.

Column 83,
Line 46, delete "wherin" and insert -- wherein --.
Line 47, delete "form" and insert -- from --.
Line 47, delete "consisnting" and insert -- consisting --.

Column 84,
Line 11, delete "further'" and insert -- further --.

Signed and Sealed this

Fourteenth Day of March, 2006

JON W. DUDAS
*Director of the United States Patent and Trademark Office*